(12) United States Patent
Niu et al.

(10) Patent No.: US 12,060,559 B2
(45) Date of Patent: Aug. 13, 2024

(54) COMPOSITIONS AND METHODS INVOLVING NON-NATURAL APTAMER LIBRARIES

(71) Applicants: CZ Biohub SF LLC, San Francisco, CA (US); The Board of Trustees of the Leland Stanford Junior University, Stanford, CA (US)

(72) Inventors: Jia Niu, Stanford, CA (US); Chelsea Lyons Gordon, Stanford, CA (US); Hyongsok Tom Soh, San Francisco, CA (US)

(73) Assignees: CZ Biohub SF, LLC, San Francisco, CA (US); The Board of Trustees of the Leland Stanford Junior University, Stanford, CA (US)

( * ) Notice: Subject to any disclaimer, the term of this patent is extended or adjusted under 35 U.S.C. 154(b) by 833 days.

(21) Appl. No.: 15/734,522

(22) PCT Filed: Jun. 19, 2019

(86) PCT No.: PCT/US2019/035378
§ 371 (c)(1),
(2) Date: Dec. 2, 2020

(87) PCT Pub. No.: WO2019/236571
PCT Pub. Date: Dec. 12, 2019

(65) Prior Publication Data
US 2021/0332360 A1    Oct. 28, 2021

Related U.S. Application Data

(60) Provisional application No. 62/680,441, filed on Jun. 4, 2018.

(51) Int. Cl.
C40B 40/06    (2006.01)
C12N 15/115    (2010.01)
(Continued)

(52) U.S. Cl.
CPC .......... *C12N 15/115* (2013.01); *C12Q 1/6811* (2013.01); *C12Q 1/686* (2013.01); *C12N 2310/16* (2013.01); *C12N 2320/13* (2013.01)

(58) Field of Classification Search
None
See application file for complete search history.

(56) References Cited

U.S. PATENT DOCUMENTS

2006/0121489 A1    6/2006    Gorenstein et al.
2008/0020939 A1    1/2008    Stanton et al.
(Continued)

FOREIGN PATENT DOCUMENTS

WO    2008073856 A2    6/2008
WO    2014082083 A1    5/2014
WO    2015049356 A1    4/2015

OTHER PUBLICATIONS

Bentley et al., "Accurate Whole Human Genome Sequencing Using Reversible Terminator Chemistry", Nature, vol. 456, No. 07517, Nov. 6, 2008, pp. 53-59.
(Continued)

*Primary Examiner* — Christian C Boesen
(74) *Attorney, Agent, or Firm* — Kilpatrick Townsend & Stockton LLP

(57) ABSTRACT

The disclosure is directed to methods and compositions for screening a library of aptamers for aptamers having a binding affinity to a target molecule. Specifically, non-natural nucleotides can be introduced onto aptamers immobilized on the surface of beads. The non-natural nucleotides can then be subsequently chemically modified to include additional binding agents. For example, copper-catalyzed azide-alkyne cycloaddition (CuAAC) reactions can be used to introduce a wide range of binding agents onto non-natural nucleotides on beads.

20 Claims, 26 Drawing Sheets
Specification includes a Sequence Listing.

(51) Int. Cl.
*C12Q 1/6811* (2018.01)
*C12Q 1/686* (2018.01)

(56) References Cited

U.S. PATENT DOCUMENTS

2011/0263459 A1   10/2011   Borer et al.
2013/0281324 A1   10/2013   Gouliaev et al.
2017/0268056 A1   9/2017    Vigneault et al.

OTHER PUBLICATIONS

PCT/US2019/035345, "International Search Report and Written Opinion", Oct. 28, 2019, 14 pages.
Tolle, "Click-SELEX-A Versatile Approach Towards Nucleobase-Modified Aptamers", Available Online at: http://hss.ulb.uni-bonn.de/2016/4492/4492.pdf, 2016, 149pages.
Wang et al., "Multi-Parameter Particle Display (MPPD): A Quantitative Screening Method for Discovery of Highly Specific Aptamers", Angewandte Chemie International Edition, vol. 56, No. 3, Jan. 16, 2017, pp. 744-747.
Wang et al., "Particle Display: A Quantitative Screening Method for Generating High-Affinity Aptamers", Angewandte Chemie International Edition, 2014, pp. 4896-4901, 126.
International Search Report and Written Opinion, Application No. PCT/US2019/035378, Mailed on Nov. 13, 2019, 9 pages.

Template used for generating non-natural aptamer-displayed particle: T1
5'- ATC CAG AGT GAC GCA GCA CGG AAC GTC TTT GTA ACT TGA AAT ACC GTG GTA GGT TGG CTA GGT TGG ACA CGG TGG CTT AGT -3' (SEQ ID NO:1)

Sequenced PCR product (sense strand) of the reverse transcription:
5'- ATC CAG AGT GAC GCA GCA CGG AAC GTC TTT GTA ACT TGA AAT ACC GTG GTA GGT TGG CTA GGT TGG ACA CGG TGG CTT AGT -3' (SEQ ID NO:2)

FIGS. 12C

```
3-1m:       GATCCCAGTCCGAAGTAATCGAAGCAACACGCACGACAGGAGAGCAAGAGGCAGAAGAACAAGAGCAAACGGCAAAAGG (SEQ ID NO:3)
A22_23:     GATCCCAGTCCGAAGTAATCGAAGCAACACGCACGACAGGAGAGCAAGAGGCAGAAGAACAAGAGCAAACGGCAAAAGG (SEQ ID NO:4)
A27_29:     GATCCCAGTCCGAAGTAATCGAAGCAACACGCACGACAGGAGAGCAAGAGGCAGAAGAACAAGAGCAAACGGCAAAAGG (SEQ ID NO:5)
A37_40:     GATCCCAGTCCGAAGTAATCGAAGCAACACGCACGACAGGAGAGCAAGAGGCAGAAGAACAAGAGCAAACGGCAAAAGG (SEQ ID NO:6)
A45_46:     GATCCCAGTCCGAAGTAATCGAAGCAACACGCACGACAGGAGAGCAAGAGGCAGAAGAACAAGAGCAAACGGCAAAAGG (SEQ ID NO:7)
A50:        GATCCCAGTCCGAAGTAATCGAAGCAACACGCACGACAGGAGAGCAAGAGGCAGAAGAACAAGAGCAAACGGCAAAAGG (SEQ ID NO:8)
A45_46_22:  GATCCCAGTCCGAAGTAATCGAAGCAACACGCACGACAGGAGAGCAAGAGGCAGAAGAACAAGAGCAAACGGCAAAAGG (SEQ ID NO:9)
A45_46_23:  GATCCCAGTCCGAAGTAATCGAAGCAACACGCACGACAGGAGAGCAAGAGGCAGAAGAACAAGAGCAAACGGCAAAAGG (SEQ ID NO:10)
A45_46_27:  GATCCCAGTCCGAAGTAATCGAAGCAACACGCACGACAGGAGAGCAAGAGGCAGAAGAACAAGAGCAAACGGCAAAAGG (SEQ ID NO:11)
A45_46_29:  GATCCCAGTCCGAAGTAATCGAAGCAACACGCACGACAGGAGAGCAAGAGGCAGAAGAACAAGAGCAAACGGCAAAAGG (SEQ ID NO:12)
A45_46_37:  GATCCCAGTCCGAAGTAATCGAAGCAACACGCACGACAGGAGAGCAAGAGGCAGAAGAACAAGAGCAAACGGCAAAAGG (SEQ ID NO:13)
A45_46_40:  GATCCCAGTCCGAAGTAATCGAAGCAACACGCACGACAGGAGAGCAAGAGGCAGAAGAACAAGAGCAAACGGCAAAAGG (SEQ ID NO:14)
```

COMPOSITIONS AND METHODS INVOLVING NON-NATURAL APTAMER LIBRARIES

REFERENCE TO RELATED APPLICATIONS

This application is a 371 application and claims the benefit of PCT Application No. PCT/US2019/035378, filed Jun. 4, 2019, which claims benefit of U.S. Provisional Patent Application No. 62/680,441, filed Jun. 4, 2018, which applications are incorporated herein by reference in their entirety.

STATEMENT AS TO RIGHTS TO INVENTIONS MADE UNDER FEDERALLY SPONSORED RESEARCH AND DEVELOPMENT

This invention was made with Government support under contract N66001-14-2-4055, awarded by the Defense Advanced Research Projects Agency. The Government has certain rights in the invention.

REFERENCE TO A SEQUENCE LISTING

The Sequence Listing written in file 103182-1138392-000810WO_SL.txt created on Nov. 17, 2019, 14 KB, machine format IBM-PC, MS-Windows operating system, is hereby incorporated by reference in its entirety for all purposes.

BACKGROUND OF THE DISCLOSURE

Interactions between glycans and carbohydrate-binding proteins mediate many biological processes, including cell-cell interaction, cellular signaling, entry of pathogens into host cells, and discrimination between "self" and "nonself" by immune cells (Boukerb et al., 2014; Gabius et al., 2011; Macauley et al., 2014; Solís et al., 2015). Accordingly, there is considerable interest in developing synthetic affinity reagents that can potentially modulate these interactions for both research and clinical applications. It is critical that such reagents bind strongly and specifically to the target protein but not to other, related carbohydrate-binding proteins. Unfortunately, this has proven extremely challenging. For example, many lectins—one of the most prominent classes of carbohydrate-binding proteins—are structurally homologous (Gabius et al., 2011). As a result, the majority of current lectin affinity reagents exhibit only modest or poor specificity (Arnaud et al., 2013; Jin et al., 2009; Sears and Wong, 1999; Yang et al., 2011). This greatly reduces their utility as research tools, and creates an unacceptable risk of off-target effects in potential therapeutic applications (Ernst and Magnani, 2009).

Synthetic "glycomimetic" reagents that display key elements of a glycan's protein-binding agent represent a promising solution to this problem. To this end, several groups have adopted rational design-based approaches—for example, achieving synergistic binding by coupling glycomimetic affinity reagents to secondary binding motifs that recognize peripheral groups surrounding the carbohydrate binding site on the target protein (Cecioni et al., 2015; Egger et al., 2013; Kelm et al., 2013; Prescher et al., 2014; Shelke et al., 2010; Zeng et al., 2011). Although some of these rationally designed reagents exhibit high affinity for their target, this approach requires detailed structural information about the carbohydrate binding site, and such high-resolution structural data are only available for a subset of lectins (Committee on Assessing the Importance and Impact of Glycomic and Glycoscience—National Research Council, 2012).

As an alternative, others have pursued strategies based on the directed evolution of large combinatorial molecular libraries (Bittker et al., 2002). This approach also offers considerably higher throughput relative to rational design strategies, which entail a laborious process of synthesis, testing, and optimization. For example, Krauss and coworkers have used library-based selection approaches with both nucleic acid- and polypeptide-based glycan scaffolds to select affinity reagents for 2G12, a protein that binds glycans associated with the HIV envelope protein gp120 (Horiya et al., 2014; Macpherson et al., 2011; Temme et al., 2014). Some of these affinity reagents exhibited impressive affinities for 2G12, but their specificities were not established. Derda and coworkers combined directed evolution and fragment-based approaches to discover a class of mannose-modified short peptides that exhibit modest (micromolar) affinity and specificity for the lectin concanavalin A (ConA), but these reagents also bound other lectins belonging to the same family (Ng et al., 2015). As such, there is currently no reliable, generalizable strategy for efficiently generating glycomimetic affinity reagents that exhibit excellent affinity and specificity for a given carbohydrate-binding protein.

BRIEF SUMMARY OF THE DISCLOSURE

In one aspect, the disclosure features a plurality of beads linked to aptamers comprising at least one non-natural nucleotide, wherein sequences of aptamers linked to different beads are different and wherein beads in the plurality are linked to multiple copies of only one aptamer, wherein the base of the non-natural nucleotide is covalently bonded to a binding agent.

In some embodiments, the non-natural nucleotide is covalently bonded to the binding agent via a triazole moiety. In some embodiments, the non-natural nucleotide is C8-alkyne-dUTP.

The aptamers linked to the beads may comprise at least first and a second non-natural nucleotides that are structurally-different. In some embodiments, the first non-natural nucleotide is linked to the binding agent and the second non-natural nucleotide is not linked to a binding agent. In particular embodiments, the second non-natural nucleotide comprises an aldehyde.

In some embodiments, the first non-natural nucleotide is linked to the binding agent and the second non-natural nucleotide is linked to a second binding agent. The binding agent may be an amino acid (e.g., a natural or non-natural amino acid), a sugar (e.g., a monosaccharide or a polysaccharide), a peptide (e.g., a synthetic peptide such as a peptide comprising one or more non-natural amino acids), or a protein (e.g., a synthetic protein such as a protein comprising one or more non-natural amino acids). In particular embodiments, the sugar may be a mannose. In some embodiments, the binding agent is an azide-modified tyrosine or an azide-modified tryptophan. In other embodiments, the binding agent is an azide-modified boronic acid.

The plurality of beads may comprise at least 100 beads (e.g., at least 500, 1,000, 5,000, 10,000, 50,000, or 100,000 beads) each linked to a different aptamer having a different sequence.

In another aspect, the disclosure features a method of making the plurality of beads linked to aptamers as described herein. The method comprises providing a plurality of aqueous droplets wherein a majority of the droplets comprise only one bead linked to a forward primer and only one aptamer template polynucleotide, wherein the droplets in the majority each comprise an aptamer template polynucleotide having a different sequence; performing amplification within the droplets, wherein the droplets contain nucleotide triphosphates (NTPs) and a non-natural nucleotide triphosphate having a nucleotide base linked to a functional group, wherein the forward primer hybridizes to the aptamer template polynucleotide and is extended by a polymerase using the aptamer template polynucleotide as a template to generate an extension product linked to the bead and comprising an aptamer sequence and wherein the non-natural nucleotide is incorporated into the aptamer sequence, thereby forming a plurality of beads linked to aptamers comprising at least one non-natural nucleotide; and reacting the functional group with a reactive species comprising a binding agent such that the non-natural nucleotide is covalently bonded to the binding agent. In some embodiments, the droplets in the method of making the plurality of beads linked to aptamers contain deoxynucleotide triphosphates (dNTPs) and a non-natural deoxynucleotide triphosphate having a nucleotide base linked to a functional group. In such cases, once the forward primer hybridizes to the aptamer template polynucleotide, the forward primer is extended by a DNA polymerase using the aptamer template polynucleotide as a template to generate an extension product linked to the bead and comprising an aptamer sequence.

In some embodiments of the method, the functional group is an alkyne or an azide.

The droplets in the method may contain at least a first and a second non-natural nucleotide triphosphate that are structurally-different and the first and the second non-natural nucleotide are incorporated into the aptamer sequence. In some embodiments, the first non-natural nucleotide comprises an alkyne or an azide functional group and the second non-natural nucleotide comprises an aldehyde.

In some embodiments, the method further comprises combining contents of the droplets after the performing of the amplification and before the reacting.

The non-natural nucleotide in the method may be C8-alkyne-dUTP.

In some embodiments, a first non-natural nucleotide comprises an alkyne and the reactive species comprises an azide and during the reacting the azide undergoes Cu-catalyzed azide-alkyne cycloaddition (CuAAC) with the alkyne in the non-natural nucleotide to form a covalent bond.

In some embodiments of the method, the binding agent comprises a sugar (e.g., a mannose).

In another aspect, the disclosure features a method of identifying an aptamer that binds a target molecule. The method comprises contacting the plurality of beads described herein to the target molecule; enriching the plurality of beads for beads that bind the target molecule; and determining the sequence of aptamers that bind the target molecule. In some embodiments, the target molecule is a peptide, a protein, a small molecule (e.g., less than 1500 daltons), a mixture of cellular membrane fragments, or a microorganism. In some embodiments, the target molecule is labeled.

In some embodiments, the contacting in the method further comprises contacting the plurality of beads with a labeled non-target molecule and the enriching comprises enriching for beads that do not bind the labeled non-target molecule, in which labels of the target molecule and the non-target molecule are different.

Definitions

The terms "label" and "detectable label" may be used interchangeably herein to refer to a molecule capable of detection, including, but not limited to, radioactive isotopes, fluorescers, chemiluminescers, chromophores, enzymes, enzyme substrates, enzyme cofactors, enzyme inhibitors, chromophores, dyes, metal ions, metal sols, ligands (e.g., biotin, avidin, strepavidin or haptens) and the like. Exemplary detectable moieties suitable for use as detectable labels include affinity tags and fluorescent proteins As used herein the term "aptamer" or "aptamer sequence" refers to a nucleic acid having a specific binding affinity for a target, e.g., a target molecule, wherein such target is other than a polynucleotide that binds to the aptamer or aptamer sequence through a mechanism which predominantly depends on Watson/Crick base pairing.

The terms "nucleic acid", "nucleic acid sequence", "nucleic acid molecule" and "polynucleotide" may be used interchangeably herein and refer to a polymeric form of nucleotides of any length, either deoxyribonucleotides or ribonucleotides, or analogs thereof, and may include naturally occurring nucleotides and/or modified nucleotides. Polynucleotides may have any three-dimensional structure, and may perform any function, known or unknown. Non-limiting examples of polynucleotides include a gene, a gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, control regions, isolated RNA of any sequence, nucleic acid probes, and primers. The nucleic acid molecule may be linear or circular.

As used herein, the term "oligonucleotide" can refer to a polynucleotide chain, typically less than 200 residues long, most typically between 15 and 100 nucleotides long, but also intended to encompass longer polynucleotide chains. Oligonucleotides can be single- or double-stranded.

"Non-natural nucleotide" refers to a nucleotide that is different from the natural nucleotides of adenosine, thymidine, guanosine, cytosine, and uracil. Non-natural nucleotides will generally include a sugar molecule (e.g., a five-carbon sugar such as ribose or deoxyribose), a nitrogenous base, and a phosphate group (when a free nucleotide as a triphosphate or when incorporated into a nucleic acid a monophosphate).

"Complementary", as used herein, can refer to complementarity to all or only to a portion of a sequence. The number of nucleotides in the hybridizable sequence of a specific oligonucleotide can be such that stringency conditions used to hybridize the oligonucleotide primer can prevent excessive random non-specific hybridization. The number of nucleotides in the hybridizing portion of the oligonucleotide primer can be at least as great as the defined sequence on the target polynucleotide that the oligonucleotide hybridizes to, namely, at least 5, at least 6, at least 7, at least 8, at least 9, at least 10, at least 11, at least 12, at least 13, at least 14, at least 15, at least about 20, or from about 6 to about 10 or 6 to about 12, or 12 to about 200 nucleotides, or about 10 to about 50 nucleotides.

BRIEF DESCRIPTION OF THE DRAWINGS

FIG. 1A: After conjugating the initial DNA library to forward primer-coated magnetic beads (step 1), emulsion PCR (step 2) was performed to produce monoclonal aptamer particles in which dT and dC are substituted with non-natural pyrimidine nucleotides 1 and 2, respectively. The emulsions (step 3) were then broken and a click chemistry approach (step 4) was used to conjugate carbohydrate azides (3) to the alkyne group on 1. These are converted to single-stranded aptamers (step 5) containing carbohydrate-modified deoxyuridine (4), and then combined with both target and non-target lectins, each labeled with a distinct fluorophore (step 6). FACS screening allows the exclusive isolation of those molecules that exhibit strong and specific binding to the target but not the non-target lectin (step 7). The selected non-natural aptamers are then converted back to natural DNA via a "reverse transcription"-like PCR reaction (step 8) and subjected either to sequencing analysis (step 9) or further screening. FIG. 1B: Structures of non-natural pyrimidine nucleotides and carbohydrate azides, and illustration of the non-natural aptamer synthesis process.

FIG. 3A: Structures of azido-sugars screened for click conjugation to alkyne-bearing 21-nt DNA oligonucleotide with three consecutive Is, Si. FIGS. 3B-3F: HPLC analysis of click conjugation under different conditions with different substrates. Click chemistry conditions are as follows: FIG. 3B: conjugation of 3 0.4 mM CuSO4+2 mM THPTA+4 mM sodium ascorbate; FIG. 3C: conjugation of 3 with 0.4 mM CuSO4+0.4 mM TBTA+0.8 mM TCEP; FIG. 3D: conjugation of 3 with 0.4 mM CuBr+0.4 mM TBTA; FIG. 3E: conjugation of 1-Man with 0.4 mM CuBr+ 0.4 mM TBTA; FIG. 3F: conjugation of 6-Gal with 0.4 mM CuBr+0.4 mM TBTA. DP: desired product. SM: starting material. +1 sugar and +2 sugar: products with one or two carbohydrate substrates conjugated. Only click conjugation of substrates 3 and AeGla (results not shown) with 0.4 mM CuBr+0.4 mM TBTA gave quantitative yield of the desired product without major byproducts.

FIG. 4A: The click chemistry reaction efficiently modified M1, the PCR product generated from the T1 template (after removing the antisense strand), which contains numerous 1 and 2 nucleotides. Gel lanes represent the template before (lane 1) and after strand separation either immediately after PCR (lane 2) or after subsequent click conjugation with 3 (lane 3). FIG. 4B: ESI-MS characterization of M1 (expected: 31901.2 Da, observed: 31899.4 Da).

FIG. 7A: Polymerase screen for the reverse transcription step. Lane 1: DNA ladder; lane 2: Taq polymerase, without template; lane 3: Taq polymerase, using canonical DNA template T1; lane 4: Taq polymerase, using non-natural aptamer particles as template; lane 5: KOD-XL, using non-natural aptamer particles as template; lane 6: Pwo, using non-natural aptamer particles as template; lane 7: Deep Vent, using non-natural aptamer particles as template. The arrow indicates the full-length product. FIG. 7B: Confirmation of successful reverse transcription using Taq DNA polymerase. Lane 1: PCR without template; lane 2: PCR using natural DNA, T1, as the template; lane 3: PCR using non-natural aptamer (M1) displayed on beads as template.

FIG. 9A: Binding curves of 3-1 and 3-1m to Con A and PSA based on particle-based fluorescent measurements. FIG. 9B: Binding activity for various 3-1 derivatives in the presence of 10 nM Con A. Fluorescence intensities were normalized first to particle coating, then to the relative signal of 3-1. FIG. 9C: The strong specificity of 3-1m remains clearly apparent on a larger array of 40 lectins. White open circles show the position of each lectin spot. Each lectin is spotted in duplicate. The short names of the lectins are written under the spots; pos and neg denote positive and negative controls, respectively. FIG. 9D: Quantitation of binding of 3-1m to the array at lectin concentrations ranging from 40 pM to 400 nM. Data are normalized to the fluorescence intensity of the positive control. The signals of the VVA spot were subtracted from the intensity at 0 nM due to the false positive response of this lectin. Positive and negative control array data were not included in the plot. The slightly lower fluorescence signal at the highest concentration was attributed to the self-quenching effect of the fluorophores at high local concentrations on the array surface.

FIG. 10A: 3-1. Expected mass: 30352.6; observed mass: 30348.7. FIG. 10B: 3-1m. Expected mass: 30040.5; observed mass: 30039.5. FIG. 10C: D1. Expected mass: 29766.2; observed mass: 29764.4.

FIGS. 12A-12C: Structure-activity relationship of 3-1m. FIG. 12A: Folding structure of 3-1m predicted by mFold. Note that modified nucleotide 4 has been substituted with dT in the simulation. The circled nucleotide positions were mutated to dA individually or in pairs, and the binding of the mutant non-natural aptamers was characterized in a particle-based fluorescent assay. FIG. 12B: The relative fluorescence signals of the mutant sequences, which are shown in FIG. 12C. The error bars were derived from three experimental replicates. The fluorescence signals were first normalized to particle coating, and then to the relative signal of 3-1m.

FIG. 15A: FACS plots of non-natural aptamer-displaying particles from the starting library and Rounds 1-3, where [Con A]=1 nM and [PSA]=250 nM. Percentages represent the subpopulation of particles in each quadrant. Quadrant IV (outlined in red) represents aptamers with high Con A and low PSA affinity, which were collected in each round. FIG. 15B: High-throughput sequencing shows several highly-enriched clusters of closely related sequences in the Round 3 pool. Each circle represents one enriched sequence, with colors indicating related clusters. The dotted line depicts our threshold for the most highly-enriched sequences (>100-fold). Aptamer 3-1 (red arrow) was selected for further characterization.

FIG. 17A: FACS plots depict binding of non-natural aptamer-displaying particles from the starting library and Round 3 of Click-PD. Percentages represent the subpopulation of particles in each quadrant. Quadrant IV (outlined in red) represents selected particles with high target specificity. FIG. 17B: Binding curves of D1 to fluorescently-labeled human and mouse DC-SIGN and human MBL based on particle-based fluorescent measurements.

FIG. 19A: Various concentrations of 3-1m were incubated with a human erythrocyte suspension containing 150 nM ConA, a concentration known to induce complete hemagglutination. The deposition of erythrocytes onto the bottom of the wells indicates inhibition of ConA activity. The positive control well contains only human erythrocytes, with no ConA. FIG. 19B: Inhibition of hemagglutination, as measured by increased absorbance at 655 nm. It was observed that 3-1m inhibited 150 nM ConA with an IC50 of 95.0 nM. The error bar was derived from four replicates. FIGS. 19C-19E: 40× microscopic images of normal human erythrocytes (FIG. 19C) and human erythrocytes incubated with 0.65 μM ConA (FIG. 19D) or 0.65 μM ConA with 0.8 μM 3-1m (FIG. 19E). Scale bars=40 μm.

DETAILED DESCRIPTION OF THE DISCLOSURE

I. Introduction

Figure 1A:
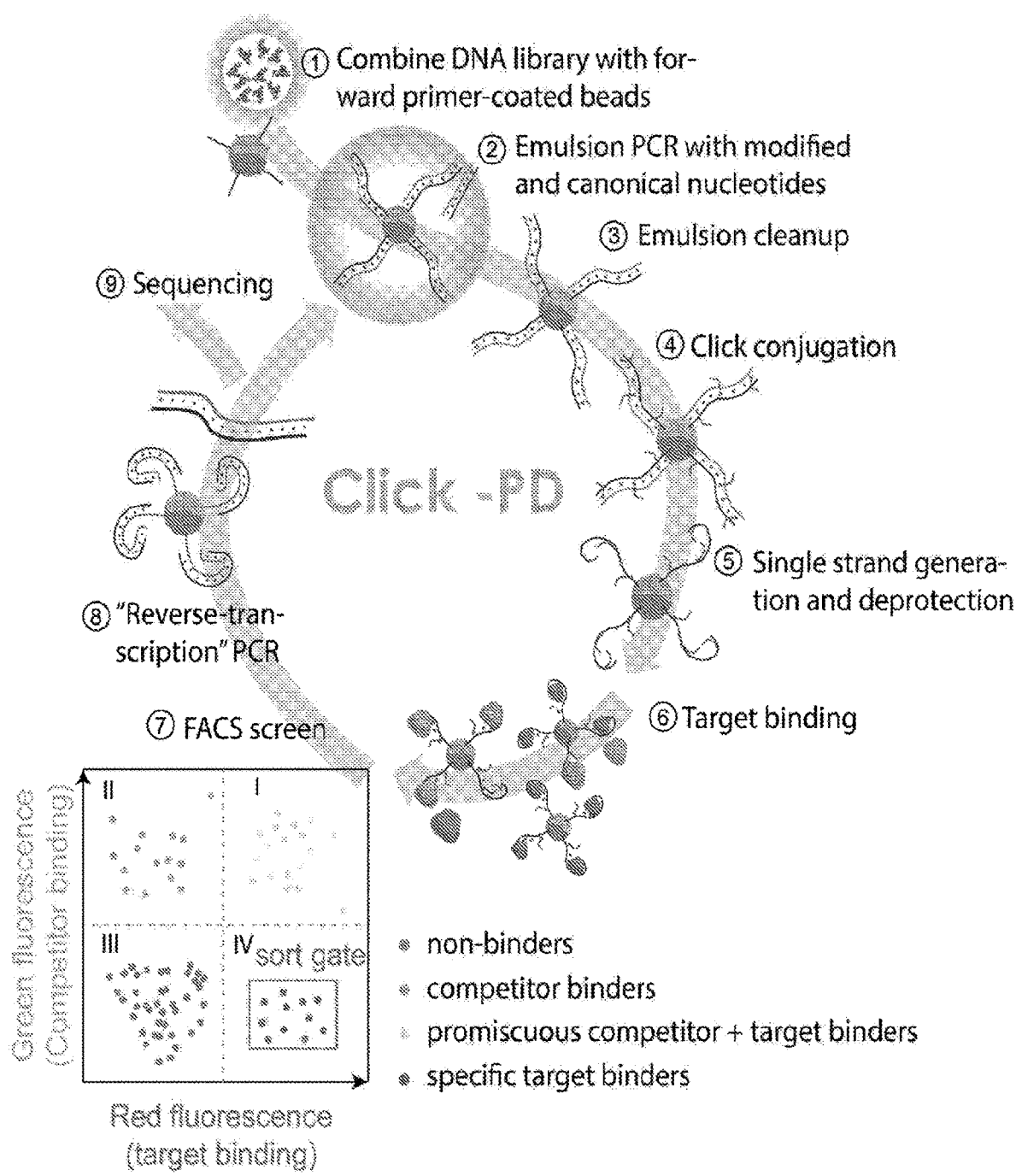
FIGS. 1A and 1B: Click-PD strategy for the synthesis and screening of lectin-specific non-natural aptamers.

The inventors have discovered how to efficiently chemically modify aptamer libraries to generate greater diversity and improved aptamer binding. Specifically, it has been discovered that non-natural nucleotides can be introduced onto beads and then subsequently chemically modified to include additional binding agents. For example, copper-catalyzed azide-alkyne cycloaddition (CuAAC) reactions can be used to introduce a wide range of binding agents onto non-natural nucleotides on beads. A resulting library of beads, each having multiple copies of a unique modified aptamer sequence, can be screened for aptamers that bind to the target.

II. Introduction of Non-Natural Nucleotides

In some embodiments, methods and compositions described herein comprise non-natural aptamers in which each non-natural aptamer contains at least one non-natural nucleotide. Non-natural nucleotides may be introduced into aptamers for example by a polymerase. The plurality of beads linked to aptamers comprising at least one non-natural nucleotide may be made in a plurality of aqueous droplets wherein a majority of the droplets comprise only one bead linked to a forward primer and only one aptamer template polynucleotide. The droplets in the majority may each comprise an aptamer template polynucleotide having a different sequence. Polynucleotide amplification may be performed within the droplets, which may contain nucleotide triphosphates (NTPs) and a non-natural nucleotide triphosphate having a nucleotide base linked to a functional group. The forward primer linked to the bead may hybridize to the aptamer template polynucleotide and may be extended by a polymerase using the aptamer template polynucleotide as a template to generate an extension product linked to the bead and comprising an aptamer sequence, in which the non-natural nucleotide is incorporated into the aptamer sequence, thus, forming a plurality of beads linked to aptamers comprising at least one non-natural nucleotide (see, e.g., US Patent Publication No. 2016/0130575).

Polymerases

Non-natural nucleotides may be introduced into aptamers using a polymerase. Polymerases may tolerate minor modifications in certain nucleotides. In some embodiments, polymerases may also be engineered to enable processing of modified or non-natural nucleotides. Polymerases may be used for nucleic acid amplification and/or sequencing applications, including real-time applications, e.g., in the context of amplification or sequencing that include incorporation of non-natural nucleotides into DNA or RNA by the polymerase.

In some instances, the methods and compositions described herein include polymerases that incorporate non-natural nucleotides into a growing template copy, e.g., during aptamer amplification. In some embodiments, the polymerase can be modified such that the active site of the polymerase is modified to reduce steric entry inhibition of the non-natural nucleotide into the active site. In some embodiments, the polymerase may be modified to improve charge-charge or hydrophobic interactions between the non-natural nucleotide and the polymerase. In some embodiments, polymerases can be modified to accommodate one or more non-natural features of the non-natural nucleotides. Polymerases can be modified using methods pertaining to protein engineering. For example, molecular modeling can be carried out based on crystal structures to identify the locations of the polymerases where mutations can be made to modify a target activity. A variety of polymerases may be used in a method or composition set forth herein including, for example, protein-based enzymes isolated from biological systems and functional variants thereof. Reference to a particular polymerase (e.g., KOD-XL polymerase (see, e.g., Nishioka et al., *J. Biotechnol.* 88:141, 2001)) will be understood to include functional variants thereof unless indicated otherwise. In some embodiments, a polymerase is a wild-type polymerase. In some embodiments, a polymerase is a modified, or mutant, polymerase. In some embodiments, a modified polymerase has a modified nucleotide binding site. In some embodiments, a modified polymerase has a specificity for a non-natural nucleotide (e.g., a non-natural nucleotide containing a modified base) that is at least about 10%, 20%, 30%, 40%, 50%, 60%, 70%, 80%, 90%, 95%, 97%, 98%, 99%, 99.5%, or 99.99% the specificity of the wild-type polymerase toward the natural nucleotide.

Nucleic acid polymerases generally useful in the methods described herein include DNA polymerases, RNA polymerases, reverse transcriptases, and mutant or altered forms thereof. DNA polymerases and their properties are described in detail in, among other places, *DNA Replication 2nd edition*, Kornberg and Baker, W. H. Freeman, New York, N.Y. (1991). Examples of DNA polymerases useful in the disclosure include, but are not limited to, *Pyrococcus furiosus* (Pfu) DNA polymerase, *Pyrococcus woesei* (Pwo) DNA polymerase, *Thermus thermophilus* (Tth) DNA polymerase, *Bacillus stearothermophilus* DNA polymerase, *Thermococcus litoralis* (Tli) DNA polymerase, 9° Nm™ DNA polymerase, Thermo Sequenase® (Amersham Pharmacia Biotech UK), Therminator™ (New England Biolabs), *Thermotoga maritima* (Tma) DNA polymerase, *Thermus aquaticus* (Taq) DNA polymerase, *Pyrococcus kodakaraensis* KOD DNA polymerase, JDF-3 DNA polymerase (from *Thermococcus* sp. JDF-3), *Pyrococcus* GB-D (PGB-D) DNA polymerase, UlTma DNA polymerase (from thermophile *Thermotoga maritima*), Tgo DNA polymerase (from *Thermococcus gorgonarius*), *E. coli* DNA polymerase I, T7 DNA polymerase, and archaeal DP1I/DP2 DNA polymerase II. Further, particular examples of thermophilic DNA polymerases include, but are not limited to, ThermoSequenase®, 9° Nm™, Therminator™, Taq, Tne, Tma, Pfu, Tfl, Tth, Tli, Stoffel fragment, Vent™ and Deep Vent™ DNA polymerase, KOD DNA polymerase, Tgo, JDF-3, and mutants, variants and derivatives thereof. Further examples of polymerases include, but are not limited to 9° N DNA Polymerase, Taq DNA polymerase, Phusion® DNA polymerase, Pfu DNA polymerase, RB69 DNA polymerase, KOD DNA polymerase, and VentR® DNA polymerase.

In some embodiments, the polymerase may be Φ29, B103, GA-1, PZA, Φ15, BS32, M2Y, Nf, G1, Cp-1, PRD1, PZE, SF5, Cp-5, Cp-7, PR4, PR5, PR722, L17, ThermoSequenase®, 9° Nm™, Therminator™ DNA polymerase, Tne, Tma, Tfl, Tth, Tli, Stoffel fragment, Vent™ and Deep Vent™ DNA polymerase, KOD DNA polymerase (Sawai, H., et al. 2002. *Bioconjugate Chem.* 13, 309. Sawai, H., et al. 2001. *Chem. Commun.* 24, 2604), Tgo, JDF-3, Pfu, Taq, T7 DNA polymerase, T7 RNA polymerase, PGB-D, UlTma DNA polymerase, *E. coli* DNA polymerase I, *E. coli* DNA polymerase III, archaeal DP1I/DP2 DNA polymerase II, 9° N DNA Polymerase, Taq DNA polymerase, Phusion® DNA polymerase, Pfu DNA polymerase, SP6 RNA polymerase, RB69 DNA polymerase, Avian Myeloblastosis Virus (AMV) reverse transcriptase, Moloney Murine Leukemia Virus (MMLV) reverse transcriptase, SuperScript® II reverse transcriptase, or SuperScript® III reverse transcriptase. Unnatural nucleoside triphosphates can be introduced for example, as described in Malyshev et al., *Nature* 509 (2014): 385-388.

Polymerases from native sources or variants thereof may be screened using an assay that detects incorporation of a non-natural nucleotide having a particular structure. In one example, polymerases can be screened for the ability to incorporate a non-natural nucleotide. Polymerases used herein that can have the ability to incorporate a non-natural nucleotide of a particular structure can also be produced using a directed evolution approach. A nucleic acid synthesis assay can be used to screen for polymerase variants having specificity for a non-natural nucleotide. In some embodiments, such an assay is an in vitro assay, e.g., using a recombinant polymerase variant. Such directed evolution techniques can be used to screen variants of any suitable polymerase for activity toward any of the non-natural nucleotides set forth herein. A polymerase may be used that displays a modified property for the non-natural nucleotide as compared to the wild-type polymerase. For example, the modified property may be, e.g., $K_m$, $k_{cat}$, $V_{max}$, polymerase processivity in the presence of a non-natural nucleotide, average template read-length by the polymerase in the presence of a non-natural nucleotide, specificity of the polymerase for a non-natural nucleotide, rate of binding of a non-natural nucleotide, or any combination thereof. In some embodiments, a polymerase described herein in its wild-type form may be able to incorporate a non-natural nucleotide into an aptamer. In other embodiments, a polymerase described herein may be engineered to incorporate a non-natural nucleotide into an aptamer.

Non-Natural Nucleotides

A non-natural nucleotide may contain a modification to either the base, sugar, or phosphate moiety compared to a naturally occurring nucleotide. A modification may be a chemical modification. Modifications may be, for example, of the 3'OH or 5'OH group of the backbone, of the sugar component, or of the nucleotide base. In some embodiments, the nucleotide is a unnatural nucleoside triphosphate.

In some embodiments, one or more of the 4 naturally-occurring nucleotides (A, G, C, T/U) are replaced with a non-natural nucleotide. In some embodiments, two, three, or all four naturally-occurring nucleotides can be replaced by different non-natural nucleotides.

In some embodiments, a non-natural nucleotide may contain modifications to the nucleotide base. A modified base is a base other than the naturally occurring adenine, guanine, cytosine, thymine, or uracil. Examples of modified bases include, but are not limited to, C8-alkyne-uracil, uracil-5-yl, hypoxanthin-9-yl (I), 2-aminoadenin-9-yl, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Examples of non-natural nucleotides include, but are not limited to, 5-substituted pyrimidines, 6-azapyrimidines and N-2 substituted purines, N-6 substituted purines, O-6 substituted purines, 2-aminopropyladenine, 5-propynyluracil, 5-propynylcytosine, 5-methylcytosine, fluorinated nucleic acids, 5-substituted pyrimidines, 6-azapyrimidines and N-2, N-6 and O-6 substituted purines, including 2-aminopropyladenine, 5-propynyluracil and 5-propynylcytosine, 5-methylcytosine (5-me-C), 5-hydroxymethyl cytosine, xanthine, hypoxanthine, 2-aminoadenine, 6-methyl other alkyl derivatives of adenine and guanine, 2-propyl and other alkyl derivatives of adenine and guanine, 2-thiouracil, 2-thiothymine and 2-thiocytosine, 5-halouracil, 5-halocytosine, 5-propynyl cytosine, other alkynyl derivatives of pyrimidine nucleic acids, 6-azo uracil, 6-azo cytosine, 6-azo thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl, other 5-substituted uracils and cytosines, 7-methylguanine, 7-methyl adenine, 2-F-adenine, 2-amino-adenine, 8-azaguanine, 8-azaadenine, 7-deazaguanine, 7-deazaadenine, 3-deazaguanine, 3-deazaadenine, tricyclic pyrimidines, phenoxazine cytidine ([5,4-b][1,4]benzoxazin-2(3H)-one), phenothiazine cytidine (1H-pyrimido[5,4-b][1,4]benzothiazin-2(3H)-one), phenoxazine cytidine (e.g., 9-(2-aminoethoxy)-H-pyrimido[5,4-b][1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one), 7-deaza-adenine, 7-deazaguanosine, 2-aminopyridine, 2-pyridone, azacytosine, 5-bromocytosine, bromouracil, 5-chlorocytosine, chlorinated cytosine, cyclocytosine, cytosine arabinoside, 5-fluorocytosine, fluoropyrimidine, fluorouracil, 5,6-dihydrocytosine, 5-iodocytosine, hydroxyurea, iodouracil, 5-nitrocytosine, 5-bromouracil, 5-chlorouracil, 5-fluorouracil, 5-iodouracil, 2-amino-adenine, 6-thio-guanine, 2-thio-thymine, 4-thio-thymine, 5-propynyl-uracil, 4-thio-uracil, N4-ethylcytosine, 7-deazaguanine, 7-deaza-8-azaguanine, 5-hydroxycytosine, 2'-deoxyuridine, and 2-amino-2'-deoxyadenosine. Examples of other synthetic nucleotides may be found in, e.g., Malyshev *Nature.* 509(7500):385, 2014.

Figure 1B:
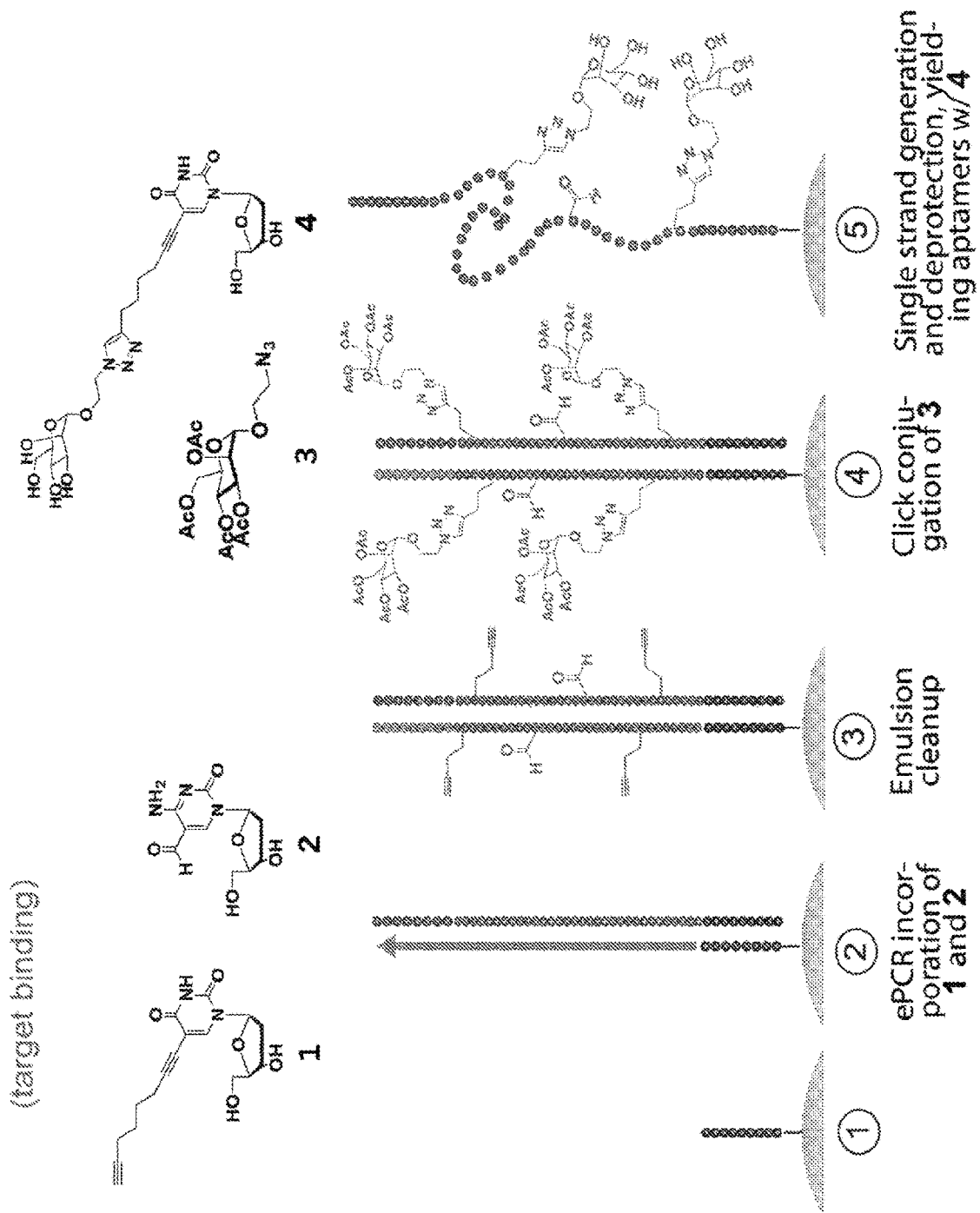

In embodiments of the methods and compositions described herein, a non-natural nucleotide comprising a functional group may be incorporated into an aptamer by a polymerase. The ability of a polymerase to incorporate a non-natural nucleotide containing a functional group into an aptamer can in some embodiments enable further modification of the aptamer by a variety of molecules as long as the molecule contains a compatible functional group (also termed herein as a "reactive species") that can react with the functional group in the non-natural nucleotide. Examples of non-natural nucleotides containing a functional group include, but are not limited to, alkyne-modified uridine (1) and aldehyde-modified cytosine (2) as shown in FIG. 1B, those described in WO2015021432, and those described in Silverman, *Chem Commun (Camb).* 30:3467-85, 2008.

Functional Groups

In some embodiments, a non-natural nucleotide may have a functional group. The non-natural nucleotide having the functional group may further be modified by reacting with it a binding agent having a compatible functional group. The functional group in the non-natural nucleotide and the compatible functional group in the binding agent react with each other to form a covalent bond, thus, conjugating the binding agent to the non-natural aptamer. Functional groups are specific, chemical reactive moieties within molecules that are responsible for certain chemical reactions, i.e., often chemical reactions with other compatible functional groups. The same functional group may have one or multiple compatible functional groups that it can react with. Compatible functional groups may react with each other to form new bonds and chemical entities. In some embodiments, compatible functional groups may react with each other to form a covalent bond (i.e., covalent conjugation), which may be used to link to molecules together. In some embodiments, a non-natural nucleotide containing a functional group may be used to conjugate an amino acid, a small molecule (e.g., a sugar molecule), a peptide (e.g., a synthetic peptide), a protein (e.g., a synthetic protein), or a non-biological moiety to the aptamer.

As described herein, a binding agent and a non-natural aptamer may be covalently conjugated to each other by reacting their respective functional groups in a covalent conjugation reaction. Compatible functional groups that may react with each other to form a covalent bond are well-known in the art. Examples of compatible functional groups include, but are not limited to, e.g., terminal alkyne and azide, maleimide and cysteine, amine and activated carboxylic acid, thiol and maleimide, activated sulfonic acid and amine, isocyanate and amine, azide and alkyne, and alkene and tetrazine.

For example, if one of the functional groups is an amino group, examples of functional groups capable of reacting with amino groups include, e.g., alkylating and acylating agents. Representative alkylating agents include: (i) an α-haloacetyl group, e.g., XCH2CO— (where X=Br, Cl, or I); (ii) a N-maleimide group, which may react with amino groups either through a Michael type reaction or through acylation by addition to the ring carbonyl group; (iii) an aryl halide, e.g., a nitrohaloaromatic group; (iv) an alkyl halide; (v) an aldehyde or ketone capable of Schiff's base formation with amino groups; (vi) an epoxide, e.g., an epichlorohydrin and a bisoxirane, which may react with amino, sulfhydryl, or phenolic hydroxyl groups; (vii) a chlorine-containing of s-triazine, which is reactive towards nucleophiles such as amino, sufhydryl, and hydroxyl groups; (viii) an aziridine, which is reactive towards nucleophiles such as amino groups by ring opening; (ix) a squaric acid diethyl ester; and (x) an α-haloalkyl ether. Examples of amino-reactive acylating groups include, e.g., (i) an isocyanate and an isothiocyanate; (ii) a sulfonyl chloride; (iii) an acid halide; (iv) an active ester, e.g., a nitrophenylester or N-hydroxysuccinimidyl ester; (v) an acid anhydride, e.g., a mixed, symmetrical, or N-carboxyanhydride; (vi) an acylazide; and (vii) an imidoester. Aldehydes and ketones may be reacted with amines to form Schiff's bases, which may be stabilized through reductive amination.

It will be appreciated that certain functional groups may be converted to other functional groups prior to reaction, for example, to confer additional reactivity or selectivity. Examples of methods useful for this purpose include conversion of amines to carboxyls using reagents such as dicarboxylic anhydrides; conversion of amines to thiols using reagents such as N-acetylhomocysteine thiolactone, S-acetylmercaptosuccinic anhydride, 2-iminothiolane, or thiol-containing succinimidyl derivatives; conversion of thiols to carboxyls using reagents such as α-haloacetates; conversion of thiols to amines using reagents such as ethylenimine or 2-bromoethylamine; conversion of carboxyls to amines using reagents such as carbodiimides followed by diamines; and conversion of alcohols to thiols using reagents such as tosyl chloride followed by transesterification with thioacetate and hydrolysis to the thiol with sodium acetate.

III. Introduction of Binding Agents to Non-Natural Nucleotides in Aptamers

A binding agent may be introduced to a non-natural aptamer that is linked to a solid support (e.g., the surface of a particle) by conjugating to a non-natural nucleotide in the non-natural aptamer. A non-natural aptamer containing one or more non-natural nucleotides having a functional group may be further modified with a binding agent having a compatible functional group. For example, an alkyne-modified non-natural nucleotide (e.g., ((1) in FIG. 1B) can be further conjugated with an azide-modified molecule, such as an azide-modified binding agent (e.g., an azide-modified mannose). As shown in FIG. 1B, azide-modified mannose is conjugated to alkyne-modified non-natural nucleotide (C8-alkyne-deoxyuridine) in the aptamer (step 4) while the products are still double-stranded on the particle surface. This approach was chosen because the alkyne side chain at the 5-position of uracil adopts an outward-pointing conformation in the major groove of the double helix, which prevents steric hindrance caused by single-stranded nucleic acid folding and thus allows for more efficient and uniform modification. The monosaccharide-modified, double-stranded PCR products are subsequently treated with NaOH and ammonium hydroxide to remove the antisense strand and deprotect the monosaccharide moiety, resulting in particle-displayed non-natural aptamers that incorporate monosaccharide-conjugated nucleotides (step 5).

In some embodiments, the binding agent may serve the function of binding to a target molecule to bring the target molecule in proximity to the aptamer during the process of screening the aptamers for binding to the target molecule. Different functional groups that may be used in the non-natural nucleotide and the binding agent such that the binding agent can be conjugated to the non-natural aptamer are discussed in detail above (e.g., compatible functional groups include, but are not limited to, e.g., terminal alkyne and azide, maleimide and cysteine, amine and activated carboxylic acid, thiol and maleimide, activated sulfonic acid and amine, isocyanate and amine, azide and alkyne, and alkene and tetrazine). Exemplary binding agents can include, for example, a sugar (e.g., a monosaccharide or a polysacciarde), amino acid (e.g., a natural or non-natural amino acid; e.g., tyrosine, phenylalanine, or tryptophan), small molecule (e.g., a drug or other molecule, optionally less than 1500, 2500, or 5000 daltons), peptide (e.g., a synthetic peptide), protein (e.g., a synthetic protein), non-biological moiety, or other moieties. Examples of chemical conjugation reactions that may be used to conjugate a binding agent to a non-natural nucleotide in a non-natural aptamer are described further herein.

Cu-Catalyzed Azide-Alkyne Cycloaddition (CuAAC)

In some embodiments of the methods and compositions described herein, a non-natural nucleotide in a non-natural aptamer may contain an alkyne or azide functional group. Two functional groups, a terminal alkyne and an azide, may undergo copper(I)-catalyzed azide-alkyne cycloaddition (CuAAC; also referred to as Cu-catalyzed click chemistry or simply click chemistry) to form the covalent moiety 1,2,3-triazole. In some embodiments, a non-natural aptamer with a non-natural nucleotide having an alkyne functional group may be further modified with a binding agent having an azide functional group. In other embodiments, a non-natural aptamer with a non-natural nucleotide having an azide functional group may be further modified with a binding agent having an alkyne functional group.

While the reaction CuAAC can be performed using commercial sources of copper(I) such as cuprous bromide or iodide, the reaction works much better using a mixture of copper(II) (e.g., copper(II) sulfate) and a reducing agent (e.g., sodium ascorbate) to produce Cu(I) in situ. As Cu(I) is unstable in aqueous solvents, stabilizing ligands (e.g., TBTA (tris-(benzyltriazolylmethyl)amine), THPTA (tris(hydroxypropyltriazlylmethyl) amine), BTTES (bis[(tert-butyltriazoyl)methyl]-[(sulfoxy ethyltriazoyl)methyl]-amine), BTTAA (bis[(tert-butyltriazoyl)methyl]-[2-carboxymethyltriazoyl) methyl]-amine) are effective for improving the reaction outcome. The reaction can be run in a variety of solvents, and mixtures of water and a variety of miscible organic solvents including alcohols, DMSO, DMF, tBuOH, and acetone. In particular embodiments, the reaction condition includes $CuSO_4$, THPTA ligand, and sodium ascorbate in water.

As described herein, in particular embodiments, a polymerase may incorporate a non-natural nucleotide containing a terminal alkyne into an aptamer, thus creating a non-natural aptamer containing a terminal alkyne functional group. The terminal alkyne-containing non-natural aptamer may be further labeled with any molecule containing an azide as the compatible functional group. For example, C8-alkyne-deoxyuridine is well tolerated by commercially-available polymerases, and enables chemical modification of an aptamer through CuAAC without polymerase engineering. As described herein, non-natural aptamers containing C8-alkyne-deoxyuridine may react with azide-containing binding agents in Cu-catalyzed click chemistry directly on the sequencer flow cell. In other embodiments, a polymerase may incorporate a non-natural nucleotide containing an azide into an aptamer, thus creating a non-natural aptamer containing an azide functional group. The azide-containing non-natural aptamer may be further labeled with any molecule containing a terminal alkyne as the compatible functional group.

Cu-Free Azide-Alkyne Cycloaddition

In some embodiments of the methods and compositions described herein, an alkyne and an azide may undergo copper-free azide-alkyne cycloaddition (also referred to as Cu-free click chemistry) to form the covalent moiety 1,2,3-triazole. Copper-free azide-alkyne cycloaddition makes use of alkynes activated by ring strain, such as cyclooctynes, to accelerate the triazole-forming reaction. Such strain-promoted cycloadditions, even without catalysts such as Cu(I), can proceed efficiently. Examples of cyclooctynes are available in the art and include, but are not limited to, monofluorinated cyclooctynes, difluorinated cyclooctynes, and aryl cyclooctynes (e.g., dibenzocyclooctyne and biarylazacyclooctynone). Examples of cyclooctynes that may be used in copper-free azide-alkyne cycloaddition are described in, e.g., Sletten and Bertozzi, *Acc Chem Res.* 44(9):666, 2011, Baskin et al., *Proc Natl Acad Sci USA* 104(43):16793, 2007, Yao et al., *J Am Chem Soc.* 134(8):3720, 2012, and Kuzmin et al., *Bioconjug Chem.* 21(11):2076, 2010.

In some embodiments, a non-natural aptamer with a non-natural nucleotide having a cyclooctyne functional group may be further modified with a binding agent having an azide functional group. In other embodiments, a non-natural aptamer with a non-natural nucleotide having an azide functional group may be further modified with a binding agent having a cyclooctyne functional group.

As described herein, in particular embodiments, a polymerase may incorporate a non-natural nucleotide containing a cyclooctyne into an aptamer, thus creating a non-natural aptamer containing a cyclooctyne functional group. The cyclooctyne-containing non-natural aptamer may be further labeled with any molecule containing an azide as the compatible functional group. As described herein, non-natural aptamers containing one or more cyclooctynes may react with azide-containing binding agents in copper-free azide-alkyne cycloaddition directly on the sequencer flow cell. In other embodiments, a polymerase may incorporate a non-natural nucleotide containing an azide into an aptamer, thus creating a non-natural aptamer containing an azide functional group. The azide-containing non-natural aptamer may be further labeled with any molecule containing a cyclooctyne as the compatible functional group.

IV. Preparation of Oligonucleotides on Particles

A plurality of particles linked to aptamers comprising at least one non-natural nucleotide may be generated. Each particle in the plurality of particles is linked to multiple copies of only one aptamer. Different particles in the plurality of particles are linked to aptamers having different sequences. A variety of suitable particles may be used in the generation of particle displaying aptamers. Such particles may be sized to have at least one dimension, e.g., diameter, of from about 50 nm to about 100 μm. For example, in some embodiments a suitable particle is sized to have at least one dimension of from about 50 nm to about 1 μm, e.g., from about 50 nm to about 500 nm, or from about 50 nm to about 100 nm. In other embodiments, a suitable particle is sized to have at least one dimension of from about 500 nm to about 100 μm, e.g., from about 1 μm to about 100 μm, or from about 50 μm to about 100 μm. Suitable particles may be generally spherical or may have any other suitable shape.

Particles may be made from a variety of suitable materials known in the art. For example, magnetic particles may be utilized in the disclosed methods and compositions. Suitable magnetic particles may include, for example, magnetic beads or other small objects made from a magnetic material such as a ferromagnetic material, a paramagnetic material, or a superparamagnetic material. Magnetic particles may include, e.g., iron oxide ($Fe_2O_3$ and/or $Fe_3O_4$). Additional particles of interest may include polymer based particles, e.g., polymer based beads. For example, polystyrene particles may be utilized. In addition, in some embodiments ceramic particles may be utilized. In some embodiments, the particles may include or be coated with a material which facilitates coupling of the particles to aptamers. Examples of coatings include polymer shells, glasses, ceramics, gels, etc. In some embodiments, the coatings include or are themselves coated with a material that facilitates coupling or physical association of the particles with the aptamers. For example, particles with exposed carboxylic acid groups may be used for attachment to aptamers.

In some embodiments, suitable particles may include one or more functional groups positioned on one or more surfaces of the particles. Suitable functional groups may include, for example, amine groups, carboxyl groups, thiol groups, biotin, $SiO_2$, EDTA, and boronic acid functional groups. In some embodiments, suitable particles may include one or more members of a specific binding pair on one or more surfaces of the particles. For example, avidin, streptavidin, Neutravidin®, Captavidin™, or biotin may be positioned on one or more surfaces of the particles.

Methods of immobilizing aptamers onto particles are known in the art. A variety of methods may be used to attach aptamers to particles. In some embodiments, aptamers may be attached to a particle having exposed carboxylic acid groups using amino group modification. For example, 5'-amino modified oligonucleotides may be used in connection with carbodiimide mediated amide bond formation to attach aptamers to particles. Carbodiimide mediated coupling methods are described in e.g., Nakajima N. and Ikade Y. (1995) *Bioconjugate Chem.*, 6(1):123-130; Gilles et al. (1990) *Anal Biochem.*, 184(2):244-248; Sehgal D. and Vijay I K. (1994) *Anal Biochem.* 218(1):87-91; and Szajani et al. (1991) *Appl Biochem Biotechnol.* 30(2):225-231. In some embodiments, primer based enrichment methods such as PCR, reverse transcriptase PCR, or primer extension are utilized to provide a library of particles displaying aptamers, nucleic acid primers may be attached to particles using carbodiimide mediated coupling to facilitate these methods. Amino group modification may also be beneficial because this coupling is covalent and can keep primers attached to the particles during thermal cycling. Alternatively, biotin labeled primers may be utilized with streptavidin-coated particles to provide primer-coated particles.

Suitable methods for the synthesis of particles displaying immobilized aptamers include, for example, emulsion PCR (see, e.g., US Patent Publication No. 2016/0130575). Generally, emulsion PCR isolates individual template DNA molecules, along with particles, in aqueous droplets within an oil phase. PCR amplification then coats each particle with clonal copies of the DNA molecule. After breaking the emulsion and removing unreacted PCR reagents, hybridized strands may be de-hybridized and the aptamer particles may be collected for subsequent screening. In some embodiments, where the aptamers include non-natural nucleotides, a modified version of the emulsion PCR method may be utilized. For example, in a first step, starting from a non-natural nucleic acid sequence as template, a DNA primer sequence and natural A/T/C/G building blocks may be used to PCR amplify the sequence into an amplified pool of natural DNA sequences (the amplified DNA will have the same sequence as the template, but not the non-natural nucleotides). In order to obtain amplified aptamers having non-natural nucleotides on particles, the natural DNA sequences derived from first step can be used as template in an emulsion reaction. A primer positioned on the particles can be used to pair with the template, and a polymerase capable of incorporating non-natural nucleotides can be used to incorporate non-natural nucleotide building blocks to extend the primer to a full-length complementary sequences. Suitable polymerases are known in the art.

V. Methods of Screening

The disclosure also includes methods of identifying an aptamer that binds a target molecule. A target molecule may be a peptide (e.g., a synthetic peptide), a protein (e.g., a synthetic protein), a sugar (e.g., a monosaccharide or a polysaccharide), a lipid, a small molecule (e.g., less than 1500 daltons), a mixture of cellular membrane fragments, or a microorganism. In some embodiments, a target molecule excludes any nucleotide or polynucleotide molecules. A solution containing the target molecule may be introduced into the solution containing the library of particles displaying aptamers. A target molecule may be attached to a readable label, e.g., a fluorescent label, such that the signal from the aptamer-bound target molecule may be read and recorded using, e.g., FACS. In other embodiments, the target molecule may not contain a readable label. In such scenarios, the aptamers in a library to be screened may have certain scaffolds (e.g., hairpin scaffold and displacement strand) that change their structures upon aptamer binding to the target molecule. The conformational change induced by target molecule binding may in turn generate a readable signal (for example due to FRET interactions) to be recorded.

Conformational aptamer binding can be useful, for example, when labeling a target perturbs the targets shape or ability to be recognized by an aptamer. Label-free generation of aptamers may utilize a scaffold-library that changes its structure upon binding to the target molecule. A variety of library architectures have been presented in the literature (e.g., D. P. Morse, *Biochem. Biophys. Res. Commun.*, vol. 359, pp. 94-101, 2007; S. G. Trevino and M. Levy, *Chembiochem*, vol. 15, no. 13, pp. 1877-81, September 2014; R. Stoltenburg, N. Nikolaus, and B. Strehlitz, *J. Anal. Methods Chem.*, vol. 2012, 2012; F. Pfeiffer and G. Mayer, *Front. Chem.*, vol. 4, no. June, pp. 1-21, 2016) including the "hairpin scaffold" and "displacement strand" libraries. In some embodiments, both formats may be used in parallel to perform selections, allowing for a direct comparison of the two library designs.

In some embodiments the presence or absence of binding is detected. For example, a threshold binding signal can be established such that higher signal than the threshold indicates binding to the aptamer on the surface of at a particular particle. In some embodiments, different concentrations of the target molecule may be probed against the particles and binding curves may be generated, thereby allowing for determination of binding affinity. Alternatively, binding specificity can be determined and selected by identifying aptamers that bind to a target molecule but do not significantly (or have reduced binding) to a non-target molecule (e.g., an isoform of the target or a molecule similar but not identical to the target molecule). In some embodiments, the target and background proteins may be labeled with distinct fluorophores, such that the on- and off-target binding of every aptamer can be characterized individually.

Furthermore, the methods described herein can be used to identify aptamers that bind to a target molecule in a complex mixture. In some embodiments, the target molecule is labeled with a first (e.g., fluorescent) label and one or more non-target molecules in the mixture are labeled with a second label that is distinguishable from the first label. In this configuration, one can select for aptamers that bind to the target molecule but do not bind to the non-target molecules (as determined by lack of signal from the second label). In some embodiments, the mixture is a complex mixture, for example a cell lysate, in which a fraction of the non-target molecules in the mixture have been labeled with the second label. In some embodiments, a non-target molecule in the mixture is similar but not identical to the target, for example is an isoform or a protein differing from the target by a post-translational modification. Alternatively, in some embodiments, one can screen for aptamers that bind to similar molecules, for example more than one members of a receptor family.

To screen for aptamers that can specifically bind to the target molecule in serum, in some embodiments, a screening approach as described in, e.g., Wang et al., *Angew. Chemie Int. Ed*. vol. 94305, pp. 744-747, 2017, may be used. Briefly, the target and serum proteins may be labeled with two different-colored fluorophores. The intensity of both fluorophores at each particle displaying non-natural aptamers may be quantitatively measured. A naïve DNA library for binding to bead-immobilized target may be pre-enriched during positive selection. Several rounds of negative selection against bead-immobilized non-target (for example human serum) may be performed to reduce the number of sequences that bind nonspecifically to non-targets. For example, a control screen against target in buffer, in a titration series with the target protein labeled with a first fluorophore may be first performed. Next, an identical titration series may be performed, except with labeled target diluted into second fluorophore (different from first fluorophore) shotgun-labeled 10% human serum. Labeling may be accomplished, for example, using active ester protein labeling kits. This dual-labeling scheme makes it possible to isolate only the aptamers that specifically bind to target but not to non-target molecules in the negative screen.

Selection in complex backgrounds introduces several challenges. The entire aptamer library might exhibit high levels of non-specific binding to background proteins. To address this, in some embodiments, several rounds of negative selection may be performed in a pre-enrichment step against bead-immobilized non-target complex mixtures, collecting only sequences that do not bind these background non-targets for further screening. The background percentage may also be adjusted to find the maximum that allows for successful screening. This may be accomplished by holding the labeled target concentration constant and titrating in increasing concentrations (e.g., 1, 3, 5, 7, and 10%) of shotgun-labeled background. This may define the maximum working range for complex background target selection.

As described herein, methods of identifying an aptamer that binds a target molecule include contacting the plurality of particles linked to aptamers comprising at least one non-natural nucleotide to the target molecule, enriching the plurality of particles for particles that bind the target molecule; and determining the sequence of aptamers that bind the target molecule. In some embodiments, the contacting further comprises contacting the plurality of particles with a labeled non-target molecule and the enriching comprises enriching for particles that do not bind the labeled non-target molecule. In some embodiments, the labels of the target molecule and the non-target molecule are different.

VI. Compositions

The disclosure includes a plurality of beads linked to aptamers comprising at least one non-natural nucleotide. The sequences of aptamers linked to different beads are different and beads in the plurality are linked to multiple copies of only one aptamer. Further, the base of the non-natural nucleotide in the aptamer may be covalently bonded to a binding agent. The plurality of beads linked to aptamers comprising at least one non-natural nucleotide may be used in screening for aptamers that bind a target molecule. A target molecule may be a peptide (e.g., a synthetic peptide), a protein (e.g., a synthetic protein), a sugar (e.g., a monosaccharide or a polysaccharide), a lipid, a small molecule (e.g., less than 1500 daltons), a mixture of cellular membrane fragments, or a microorganism. In some embodiments, a target molecule excludes any nucleotide or polynucleotide molecules. A solution containing the target molecule may be introduced into the solution containing the library of particles displaying aptamers. As described herein, a target molecule may be attached to a readable label, e.g., a fluorescent label, such that the signal from the aptamer-bound target molecule may be read and recorded using, e.g., FACS.

In the composition of the plurality of beads, the non-natural nucleotide may be covalently bonded to the binding agent via a triazole moiety. For example, the non-natural nucleotide may be C8-alkyne-dUTP, which may react and form a triazole moiety with an azide-modified binding agent in a CuAAC reaction. The aptamers linked to the surface of the beads may also include other non-natural nucleotides having modified bases. Examples of non-natural nucleotides having modified bases are described herein. In particular embodiments, the aptamers linked to the beads comprise at least a first and a second non-natural nucleotides that are structurally different (e.g., (1) and (2) in FIG. 1B). In some embodiments, the first non-natural nucleotide is linked to the binding agent and the second non-natural nucleotide is not linked to a binding agent.

A binding agent may be introduced to a non-natural aptamer linked to the surface of the beads by conjugating to a non-natural nucleotide in the non-natural aptamer. A non-natural aptamer containing one or more non-natural nucleotides having a functional group may be further modified with a binding agent having a compatible functional group. Compatible functional groups include, but are not limited to, e.g., terminal alkyne and azide, maleimide and cysteine, amine and activated carboxylic acid, thiol and maleimide, activated sulfonic acid and amine, isocyanate and amine, azide and alkyne, and alkene and tetrazine A binding agent may be an amino acid (e.g., a natural or non-natural amino acid), a sugar (e.g., a monosaccharide or a polysaccharide; a mannose), a peptide (e.g., a synthetic peptide), or a protein (e.g., a synthetic protein). The binding agent may serve the function of binding to a target molecule to bring the target molecule in proximity to the aptamer during the process of screening the aptamers for binding to the target molecule.

In some embodiments, the aptamers linked to the beads comprise at least two non-natural nucleotides (e.g., two, three, four, five, six, seven, eight, nine, or ten) non-natural nucleotides. Some of the non-natural nucleotides may be linked to the binding agent, while other non-natural nucleotides may not be linked to the binding agent. For example, for aptamers comprising at least two non-natural nucleotides, at least one non-natural nucleotide may be linked to the binding agent. In other examples, for aptamers comprising three non-natural nucleotides, one or two non-natural nucleotides may be linked to the binding agent, while the remaining non-natural nucleotide(s) may not be linked to the binding agent. For aptamers comprising four non-natural nucleotides, one, two, or three non-natural nucleotides may be linked to the binding agent, while the remaining non-natural nucleotide(s) may not be linked to the binding agent. For aptamers comprising five non-natural nucleotides, one, two, three, or four non-natural nucleotides may be linked to the binding agent, while the remaining non-natural nucleotide(s) may not be linked to the binding agent. In some embodiments, the non-natural nucleotides that are linked to the binding agents may be linked to different binding agents. In some embodiments, the non-natural nucleotides that are not linked to the binding agent (e.g., (2) in FIG. 1B) may serve functions such as improving aptamer folding and stability, and/or forming intramolecular and intermolecular interactions.

Particles may be made from a variety of suitable materials known in the art. Suitable magnetic particles may include, for example, magnetic beads or other small objects made from a magnetic material such as a ferromagnetic material, a paramagnetic material, or a superparamagnetic material. Magnetic particles may include, e.g., iron oxide ($Fe_2O_3$ and/or $Fe_3O_4$). Additional particles of interest may include polymer based particles, e.g., polymer based beads. For example, polystyrene particles may be utilized. In addition, in some embodiments ceramic particles may be utilized. Methods of generating aptamers linked to the surface of particles are described herein. In some embodiments of the plurality of beads linked to aptamers comprising at least one non-natural nucleotide described herein, the plurality of beads may comprises at least 100 beads (e.g., at least 100, 120, 140, 160, 180, 200, 220, 240, 260, 280, 300, 320, 340, 360, 380, 400, 420, 440, 460, 480, or 500) each linked to a different aptamer having a different sequence.

EXAMPLES

Example 1—General Methods

All DNA oligonucleotides were purchased from Integrated DNA Technologies. Primers were ordered with standard desalting. PCR templates were ordered with PAGE purification. Other than the exceptions noted below, all commercially available reagents and lab supplies were purchased from Aldrich. 2-azidoethyl 2,3,4,6-tetra-O-acetyl-α-D-mannopyranoside and 2-azidoethyl 2,3,4,6-tetra-O-acetyl-β-D-galactopyranoside were purchased from LC Scientific Inc. KOD-XL DNA polymerase was purchased from Thermo Fisher Scientific. Taq polymerase was purchased from Promega. Pwo DNA polymerase was purchased from Roche. C8-Alkyne-dUTP was purchased from Axxora Inc. 5-formyl dCTP was purchased from Trilink Technologies. Deep Vent DNA polymerase and standard dNTPs were purchased from New England Biolabs. Lectin Array 40 was purchased from RayBiotech, Inc. Human erythrocytes were purchased from BioreclamationIVT. Mini-PROTEAN native and denaturing PAGE gels (10%) were purchased from Bio-Rad. Dynabeads MyOne carboxylic acid and streptavidin C1 beads for particle display and single-stranded PCR product generation, respectively, were purchased from Thermo Fisher Scientific. Recombinant Human DC-SIGNR/CD299 and Recombinant Mouse SIGNR1/CD209b Fc Chimera Proteins were purchased from R&D Systems. Goat anti-Human IgG Fc secondary antibodies conjugated with DyLight 488 and DyLight 650 were purchased from Thermo Fisher Scientific. Human MBL protein was purchased from ACROBiosystems.

ESI-MS characterization was performed by Novatia. Optical microscopy imaging was performed on an Olympus CKX-41 inverted microscope with color digital camera using 40× objectives. The images were processed with ImageJ software. Reverse-phase HPLC analysis was performed on an Agilent 1100 system using a PLRP-S 4.6×150 mm 5 μm column with 300 Å packing material, with a gradient from 95% 0.1 M triethylammonium acetate (TEAA)/5% acetonitrile to 20% 0.1 M TEAA/65% acetonitrile over 30 min. Flow cytometry assays were performed using a BD Accuri C6 flow cytometer. Fluorescence-based sorting of particles was done using a BD FACSAria III. Bio-Layer Interferometry measurements were performed with a ForteBIO Octet RED384 system, and analysis was performed using Octet Data Analysis software. MicroScale Thermophoresis measurements were carried out by 2bind.

Example 2—Polymerase-Mediated Incorporation of Modified Pyrimidine Building Blocks A PCR mixture containing 1× polymerase buffer, 0.2 mM dATP, 0.2 mM dGTP, 0.2 mM 5fdCTP (2), 0.2 mM C8-AkdUTP (1), 0.4 µM T-FP, 0.4 µM T-RP, 0.05 U/µL DNA polymerase, 20 pM PCR template T1, and water for a total volume of 50 µL was used. The cycling conditions were as follows: % ° C., 2 min+[96° C., 15 s+51° C., 30 s+72° C., 30 s]*30+72° C., 2 min+hold at 4° C. To screen KOD-XL, Pwo, and Deep Vent DNA polymerases for the efficiency of modified nucleotide incorporation, 2 µL of each PCR reaction was loaded directly onto a 10% native PAGE gel, which was run at 150 V for 30 min in 1×TBE buffer. Gels were imaged after staining with 1× GelStar Nucleic Acid Stain in TBE buffer.

Example 3—Optimization of Click Conjugation Reaction

10 µL of 100 µM 21-nt oligonucleotide substrate (containing consecutive three 1 nucleotides), 1 µL 100 mM azido-sugar in DMSO (100 eq), and 14 µL 20 mM sodium phosphate buffer, pH 8 (pre-degassed by bubbling N2 through) were combined in a 1.5 mL Eppendorf tube. Click chemistry was initiated by one of the following three conditions:
(1) Addition of premixed 1 µL 20 mM CuSO$_4$, 1 µL 0.1 M tris(3-hydroxypropyltriazolylmethyl)amine (THPTA), and 20 µL water, followed by 1 µL 0.2 M sodium ascorbate.
(2) Addition of premixed 1 µL 20 mM CuSO$_4$ and 1 µL 20 mM tris[(1-benzyl-1H-1,2,3-triazol-4-yl)methyl]amine (TBTA)] in 10 µL of 4:3:1 water:DMSO:t-BuOH, followed by addition of 2 µL 20 mM tris(2-carboxyethyl)phosphine (TCEP).
(3) Addition of 10 µL premixed 1:1 Cu:TBTA (2 mM, prepared from 1 mg CuBr+0.7 mL 10 mM TBTA in 4:3:1 water: DMSO: t-BuOH, then diluted five-fold with the same solvent).

The cap of the tube was then removed, and the de-capped tube was immediately placed in a 20 mL vial equipped with a rubber septum, followed by Ar flushing for 5 min. The sealed vial was incubated in the dark for two hours. The reaction product was purified with a Centri-Spin 10 column (Princeton Separations). 200 µL of concentrated ammonium hydroxide (18 M) was added to the purified product, and the solution was incubated at room temperature for 3 hours. 400 µL n-butanol was then added, vortex mixed, and centrifuged at 16,000×g at 4° C. for 2 min. The top organic layer was removed and discarded. The bottom aqueous layer was purified by an Oligo Clean and Concentrator spin column (Zymo Research), followed by HPLC analysis.

Example 4—PCR Amplification, Click Conjugation of 3, Single Strand Generation, and Acetyl Deprotection for an 81-NT Non-Natural Aptamer (M1)

For PCR incorporation of modified nucleotides, a PCR mixture containing 1×KOD-XL DNA polymerase buffer, 0.2 mM dATP, 0.2 mM dGTP, 0.2 mM 2, 0.2 mM 1, 0.4 µM T-FP, 0.4 µM 5'-doubly biotinylated T-RP-2Bio, 0.05 U/µL KOD-XL DNA polymerase, 20 µM PCR template T1, and water in a total volume of 5 mL was prepared in a 96 well plate. Cycling conditions were as follows: 96° C., 2 min+ [96° C., 15 s+51° C., 30 s+75° C., 30 s]*12+75° C., 2 min+hold at 4° C.

PCR reactions were then transferred into a 50 mL conical tube. 0.5 mL 3 M sodium acetate (pH 5.2) and 13.75 mL of 100% ethanol were added, followed by freezing at −80° C. for 30 min. The frozen stock was then centrifuged for 30 min at 5000 RPM at 4° C. to precipitate the DNA. The pellet was dissolved with 600 µL water, followed by purification using MinElute spin columns. The PCR product was eluted with 180 µL of 10 mM Tris buffer, pH 8.0. To this DNA solution, 40 µL of 3 M sodium acetate (pH 5.2) and 1.2 mL of 100% ethanol were added, followed by freezing at −80° C. for 30 min. The frozen stock was then centrifuged for 30 min at 21,000×g at 4° C. to precipitate the DNA. The material was resuspended in 20 µL 1×PBS buffer.

20 µL 100 mM 3 in DMSO (100 eq) and 40 µL 20 mM sodium phosphate buffer, pH 8 (pre-degassed by bubbling N2 through) were combined with 20 µL of base-modified DNA solution in a 1.5 mL Eppendorf tube. Click chemistry was initiated by the addition in reaction of 20 µL premixed solution of 1:1 Cu:TBTA (10 mM, prepared from 1 mg CuBr+0.7 mL 10 mM TBTA in 4:3:1 water:DMSO:t-BuOH). The cap of the tube was removed, and the de-capped tube was immediately placed in a 20 mL vial equipped with a rubber septum, followed by Ar flushing for 5 min. The sealed vial was incubated in the dark for two hours. To this DNA solution, 10 µL of 3 M sodium acetate (pH 5.2) and 330 µL of 100% ethanol were added, followed by freezing at −80° C. for 30 min. The frozen stock was then centrifuged for 30 min at 21,000×g at 4° C. to precipitate the DNA. The material was suspended in 350 µL 1× bind and wash buffer (B&W; 5 mM Tris, 0.5 mM EDTA, 1 M NaCl, pH 7.5).

350 µL MyOne C1 streptavidin beads was added to a 1.5 mL Eppendorf tube. The beads were captured on the side of the tube with a magnet and the supernatant was removed. The beads were washed three times with 350 s 1× B&W. The click product sample was added to the beads and mixed on a rotator for 30 min. The beads were then captured and the supernatant was discarded. The beads were washed three times with 350 µL 1× B&W, and then treated with 100 µL freshly-prepared 0.25 M NaOH solution to generate single-stranded DNA. The beads were captured by magnet, and the supernatant was collected and desalted using a CENTRI-SEP column (Princeton Separations).

The acetyl groups were deprotected by adding 200 µL concentrated ammonium hydroxide (18 M) to the collected oligos and incubating for 4 hours at room temperature. 450 µL n-butanol was then added to the solution, followed by vortexing, and centrifuging at 21,000×g at 4° C. for 1 min. The top organic layer was removed and discarded. The resulting non-natural aptamer solution was then desalted by a Centri Spin-10 column (Princeton Separations).

Example 5—Optimization of Click-PD

Figure 2:
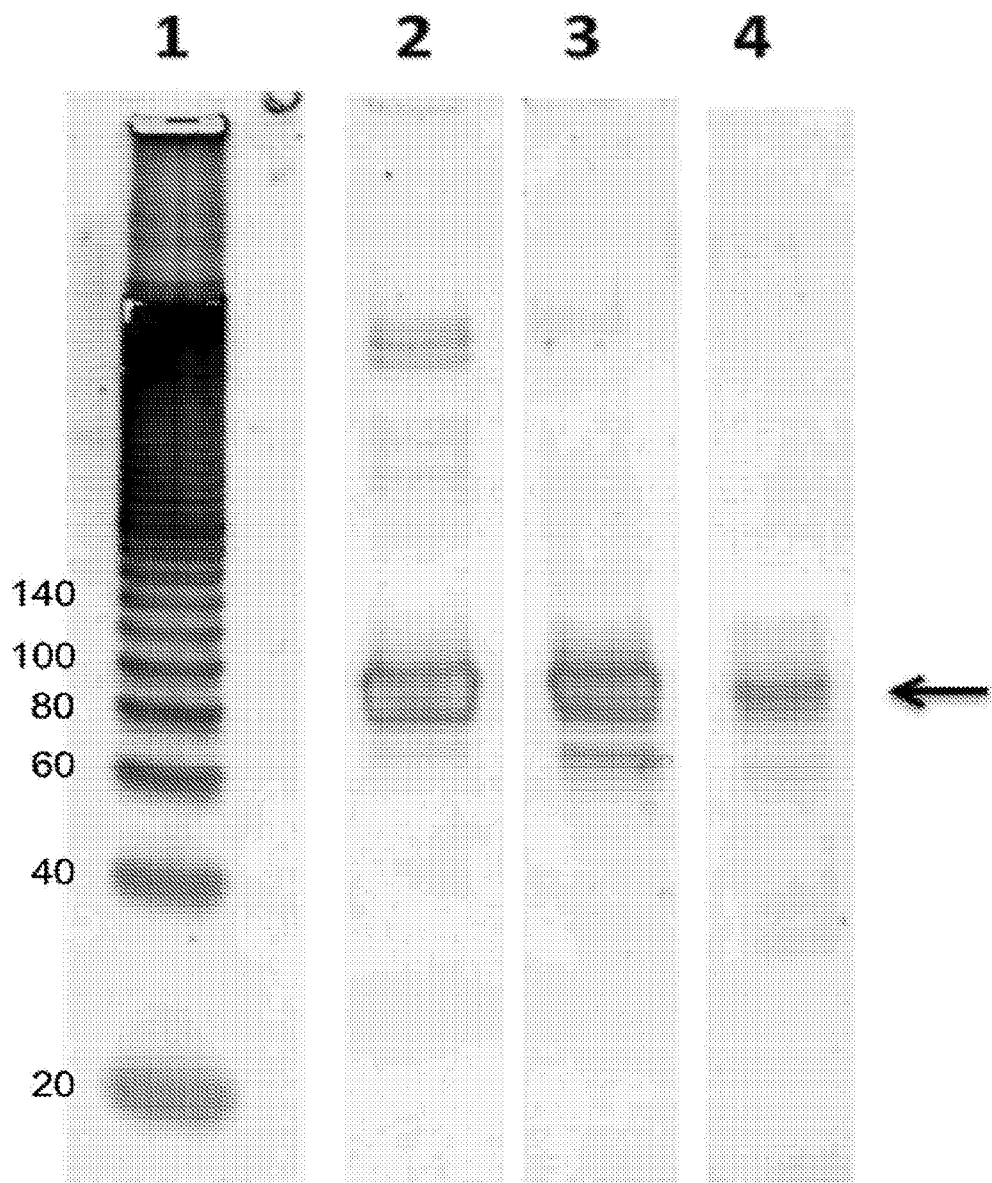
FIG. 2: Screen for polymerase-mediated incorporation of modified pyrimidine deoxyribonucleotides 1 and 2. PCR template: an 81-nt DNA oligonucleotide, T1. Lane 1: DNA ladder; lane 2: KOD-XL; lane 3: Pwo; lane 4: Deep Vent. The arrow indicates the full-length product. KOD-XL DNA polymerase gives the highest yield without a major byproduct.
Figure 3A:
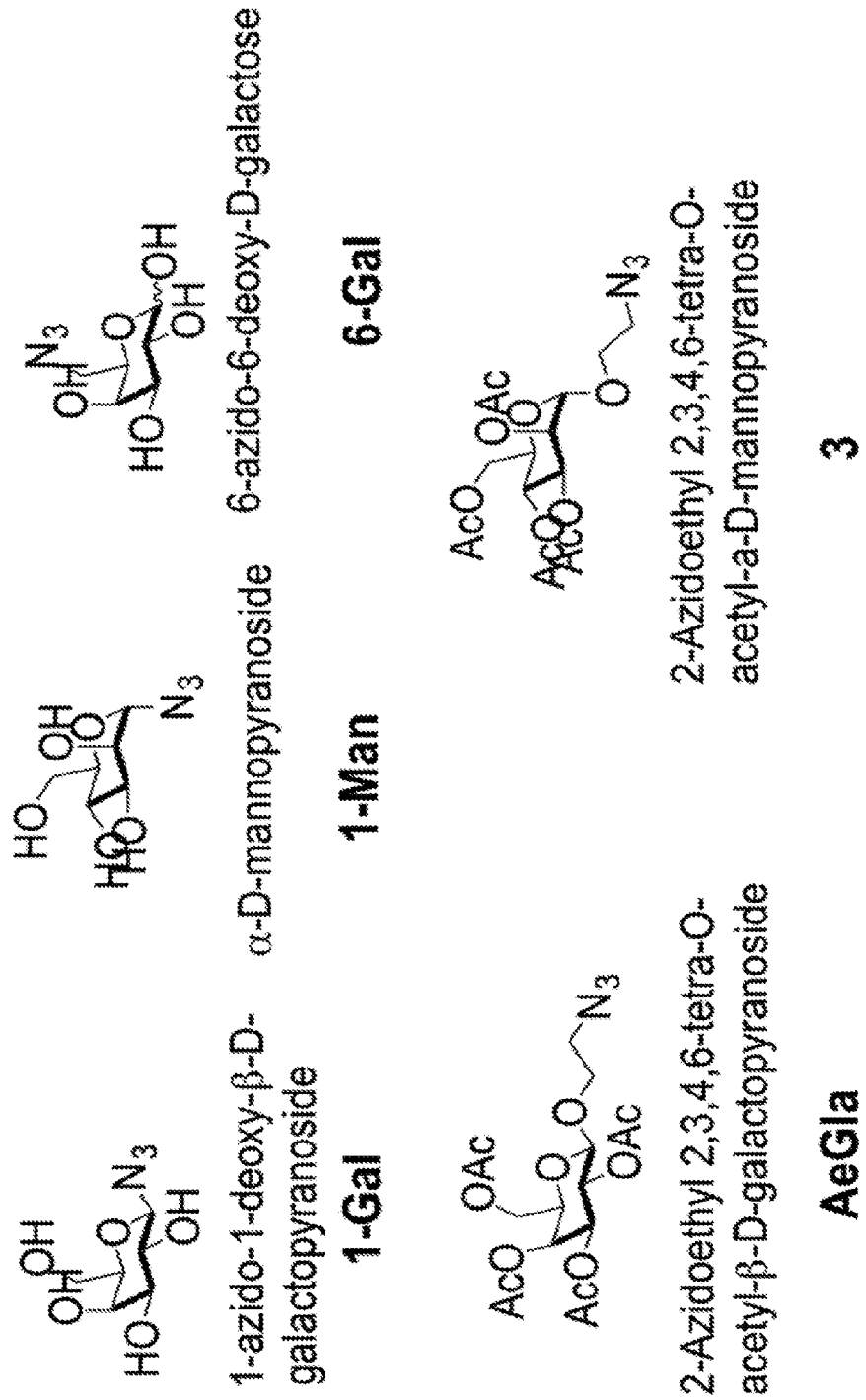
FIGS. 3A-3F: Optimization of click chemistry using a 21-nt oligonucleotide substrate with three consecutive alkyne side chains.
Figures 3B, 3C, 3D, 3E, 3F:
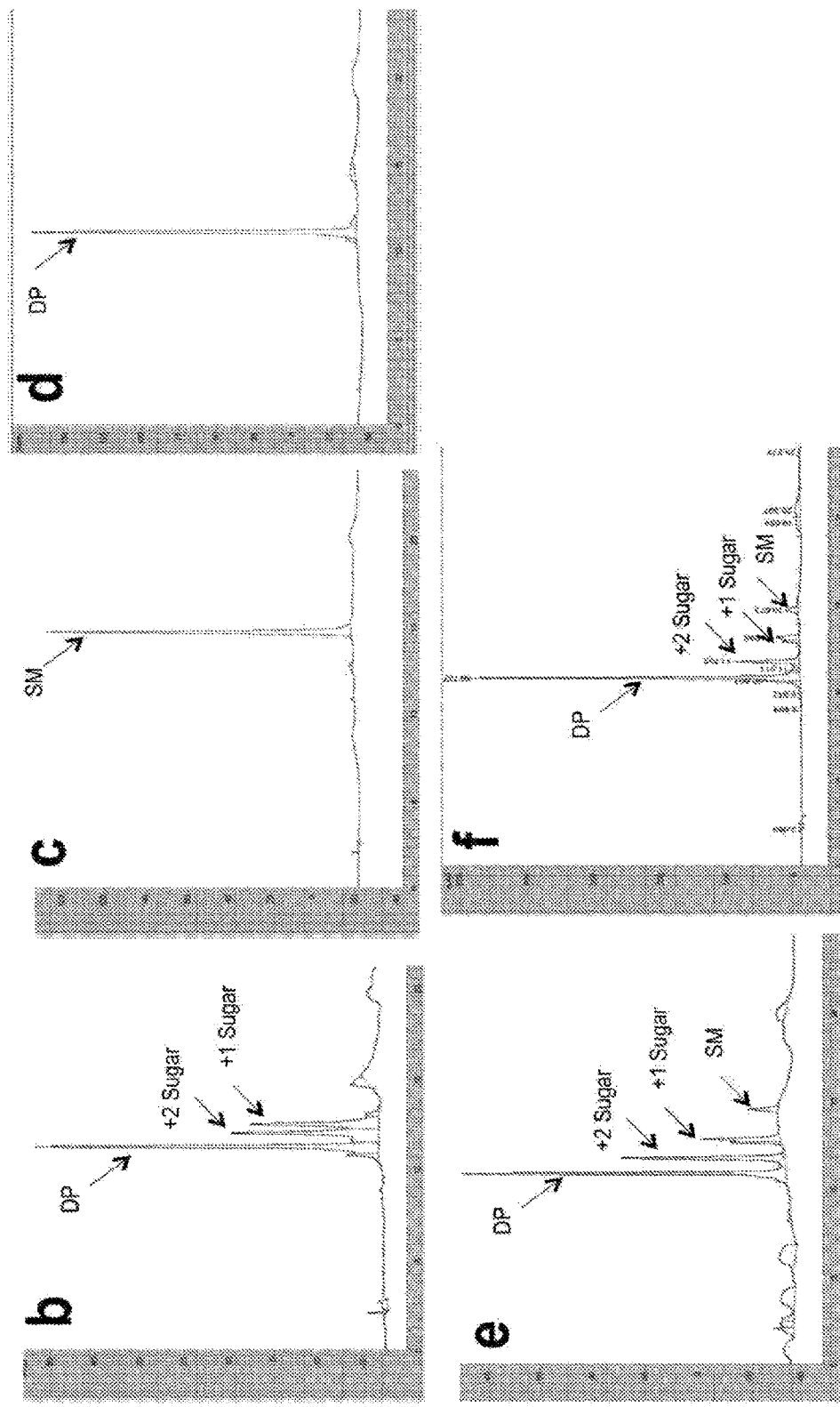
Figure 4A:
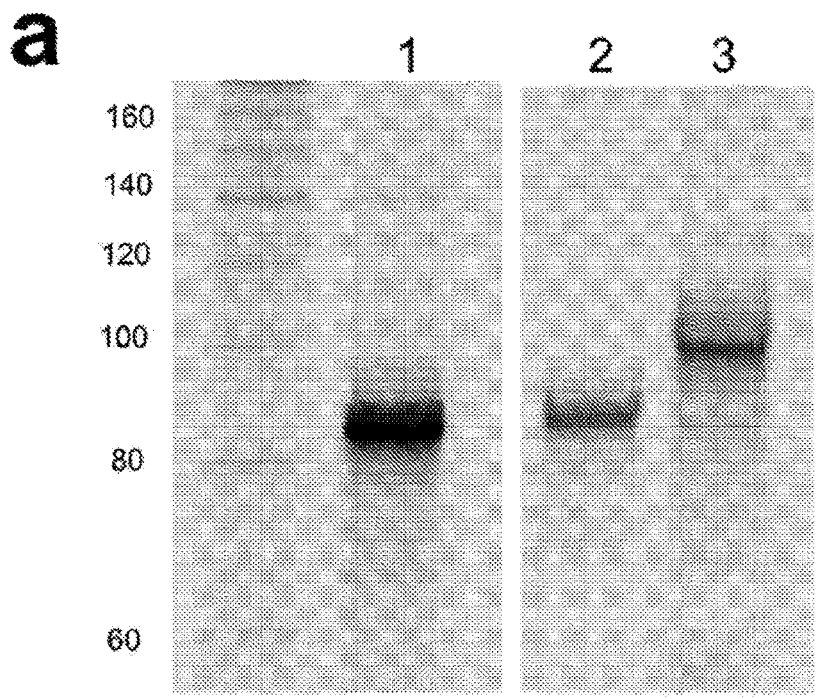
FIGS. 4A and 4B: Optimization of Click Conjugation.
Figure 4B:
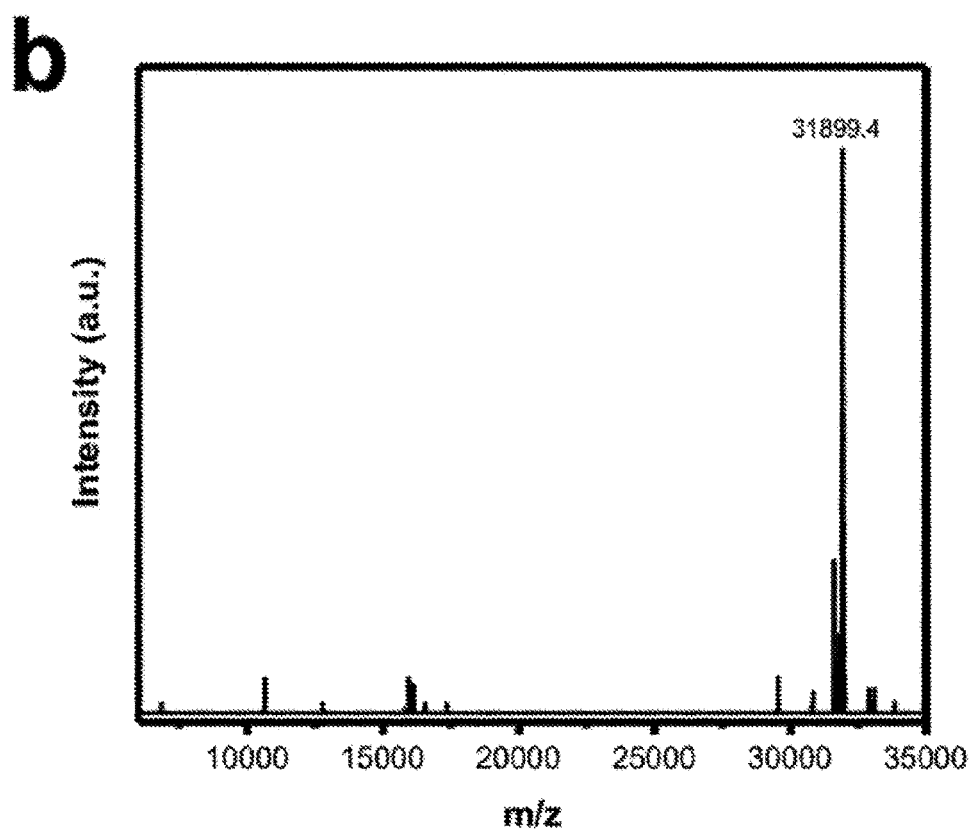
Figure 5:
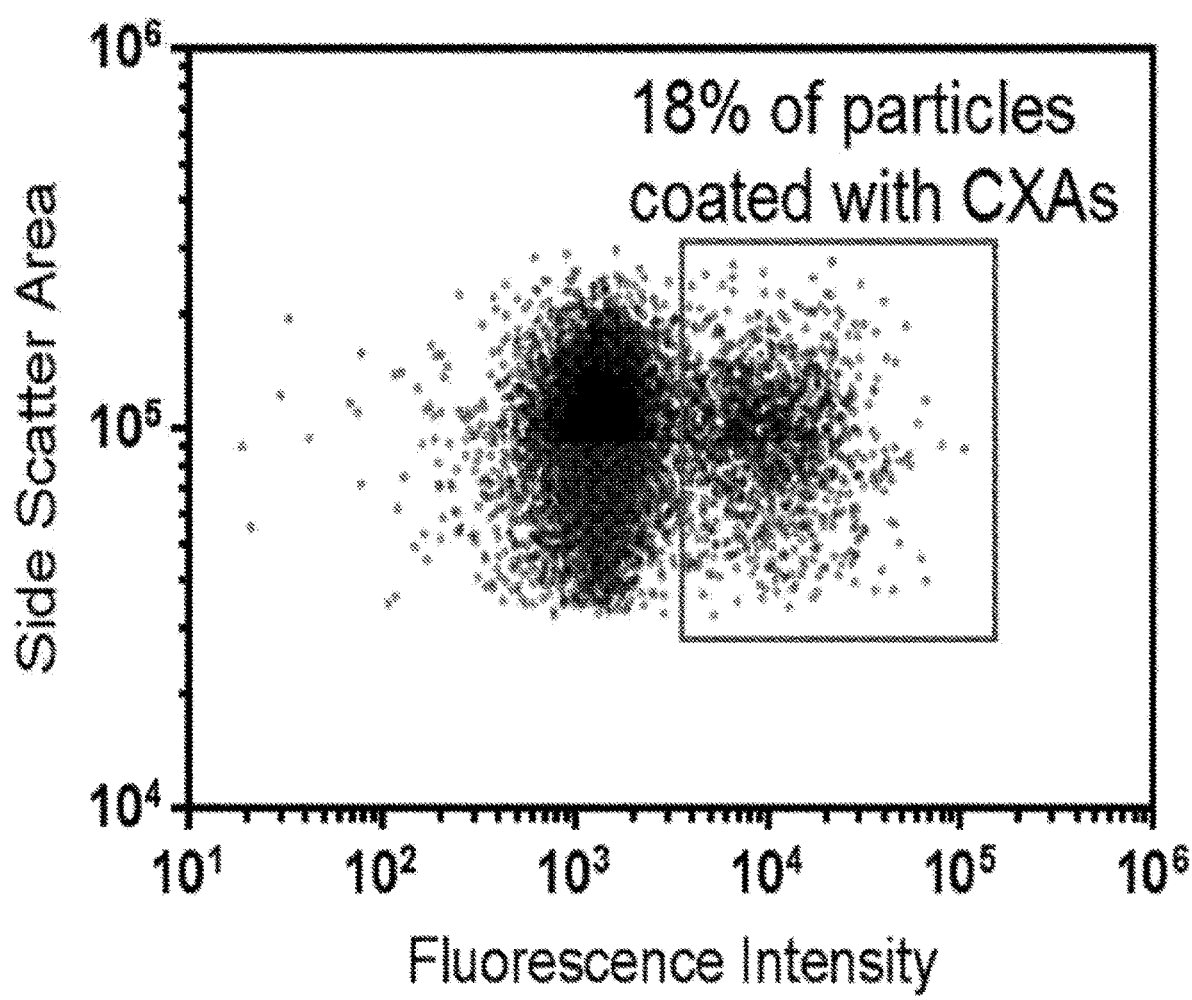
FIG. 5: Characterization of non-natural aptamer particle synthesis using flow cytometry. Fluorescent signal from the Alexa Fluor 647-labeled reverse primer shows two populations: blank particles, and particles coated with non-natural aptamers (red box). In this representative sample, 18% of the particles are coated with non-natural aptamers.
Figure 6:
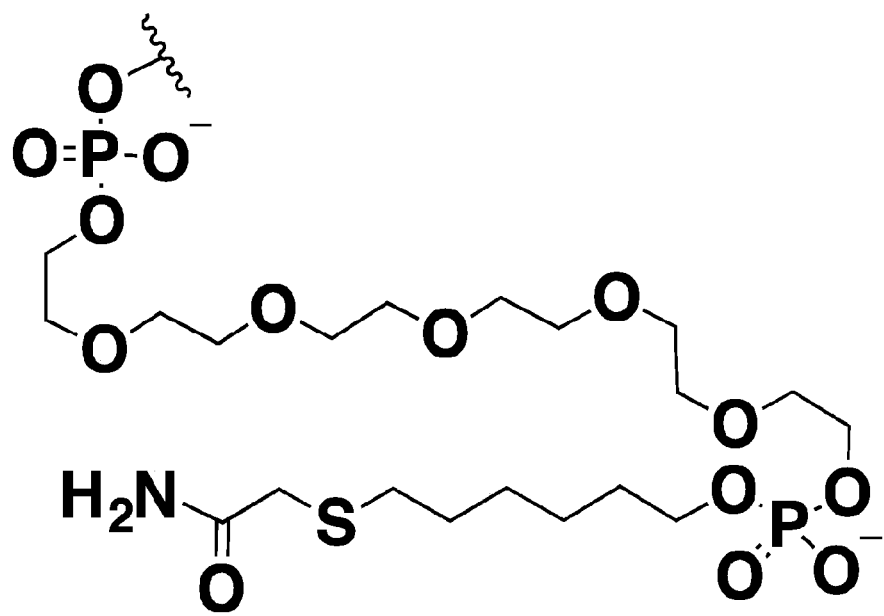
FIG. 6: Confirmation of the generation of particle-displayed non-natural aptamers. Top: structure of the "scar" of the disulfide linker after non-natural aptamer cleavage. The disulfide linker between the forward primer and the particle is cleaved by TCEP treatment followed by alkylation using iodoacetamide. Bottom: the click chemistry reaction conditions efficiently modified particle-coupled non-natural aptamers. Lane 1 contains the reaction product M1 formed in solution (see FIG. 4A), and lane 2 contains non-natural aptamer cleaved from beads after emulsion PCR and on-bead click reaction.
Figure 6:
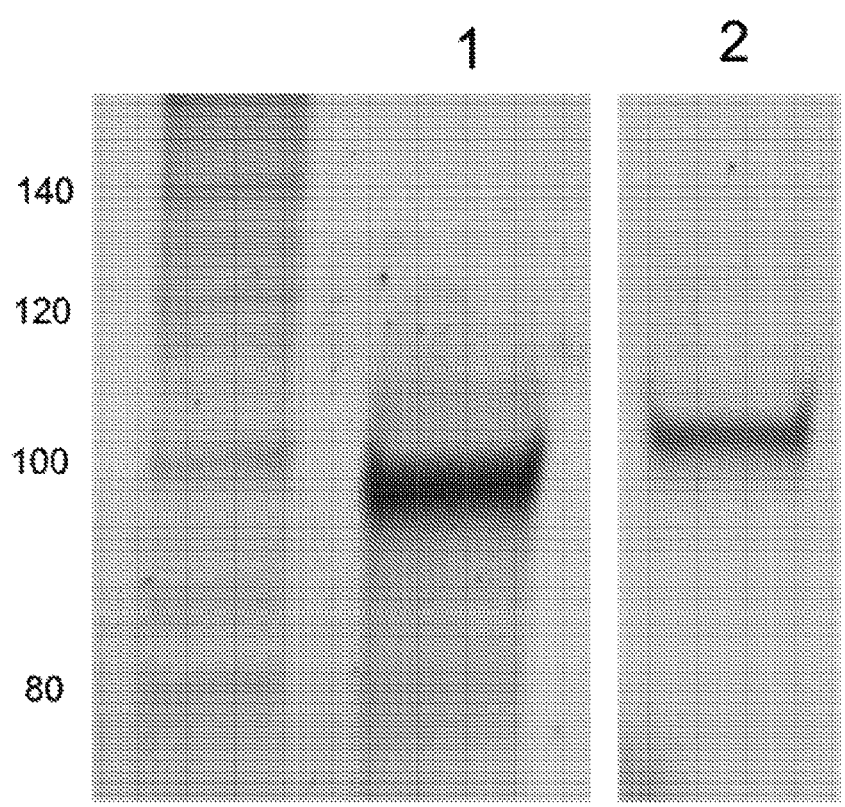
Figure 7A:
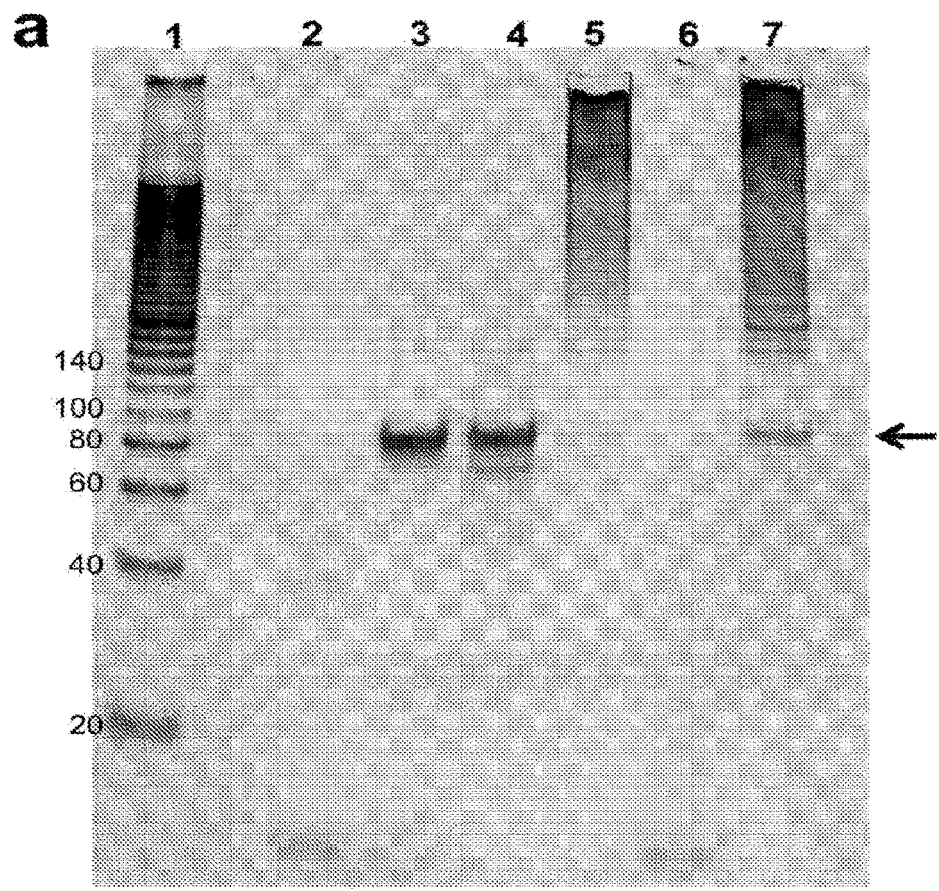
FIGS. 7A and 7B: Taq polymerase efficiently converts non-natural aptamers back to natural DNA via a 'reverse transcription' PCR process.
Figure 7B:
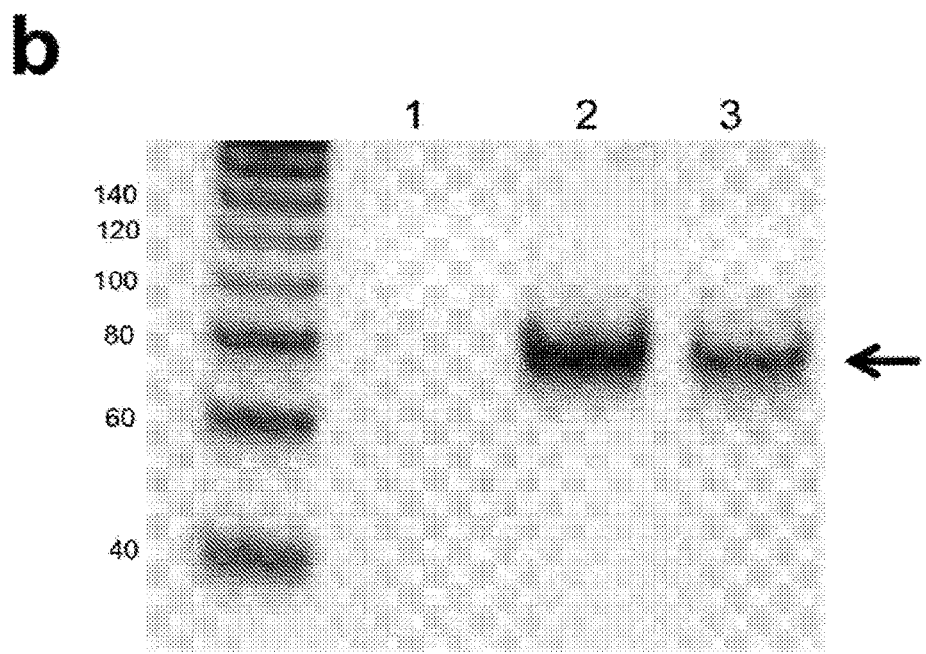
Figure 8:
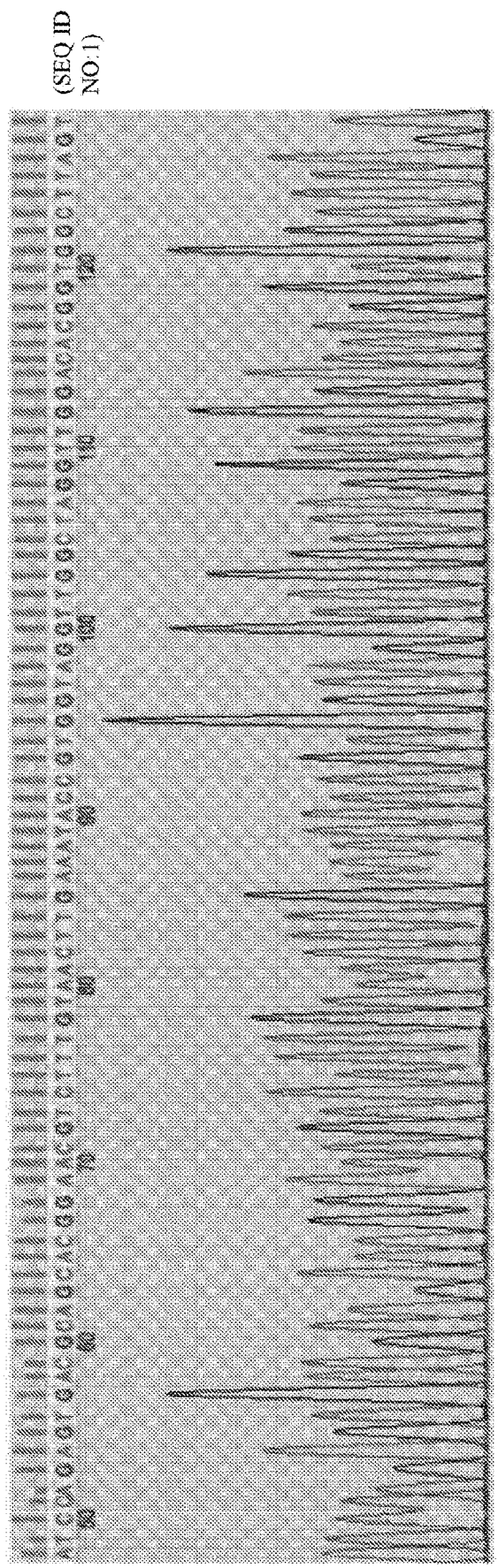
FIG. 8: Sanger sequencing of the product of reverse-transcription. PCR product from reverse-transcription were cloned into a TOPO vector and transfected into TOP10 chemically competent cells. Colonies were harvested and sent for Sanger sequencing. All 20 colonies sequenced were either sequence matched with T1 or the complementary sequence of T1, demonstrating good fidelity for the reverse-transcription reaction.

First, several DNA polymerases were screened to identify a candidate that allows effective replacement of dT and dC with 1 and 2 (FIG. 1B), respectively, during PCR (FIG. 2). A series of test PCR reactions showed that KOD-XL polymerase provided the highest yield and purity. Next, reaction conditions were optimized for coupling mannose to 1 via click chemistry. After screening various reaction conditions for the click conjugation of monosaccharides with azido substitutions at various positions, it was determined that a reaction with 2,3,4,6-tetra-O-acetyl-protected, 2-azidoethyl derivatives, such as 3 (FIG. 1B), performed with copper(I) bromide and tris[(1-benzyl-1H-1,2,3-triazol-4-yl)methyl] amine (TBTA), achieves quantitative yield of the fully-conjugated product (FIGS. 3A-3F). The successful and efficient PCR incorporation of 1 and 2 and subsequent click chemistry modification were confirmed by denaturing polyacrylamide gel electrophoresis (PAGE; FIG. 4A) and electrospray ionization mass spectrometry (ESI-MS, FIG. 4B). It was then confirmed that these non-natural aptamers are efficiently displayed on the particle surface by fluorescently labeling the 3'-end of the non-natural aptamers to allow for FACS characterization after emulsion PCR (FIG. 5). A cleavable disulfide linker was incorporated between the aptamer and the particle to allow cleavage of the modified DNA for electrophoretic analysis (FIG. 6). The slightly lower mobility of the cleaved non-natural aptamer was attributed to the extra mass from the "scar" of the disulfide linker. Finally, the "reverse transcription" process was optimized to convert the carbohydrate-modified DNA back to natural DNA molecules with the same nucleotide sequence. After testing a number of DNA polymerases (FIG. 7A), it was found that Taq efficiently generated DNA of the correct length from the non-natural aptamers (FIG. 7B). This is consistent with previous findings that family B DNA polymerases such as Taq are particularly suited for primer extension along modified nucleic acid templates (Hili et al., 2013; Jager et al., 2005). Sanger sequencing showed that the product generated by Taq polymerase was identical to the starting template, confirming the fidelity of the reverse transcription process (FIG. 8).

Example 6—General Procedure for Generating Particle-Displayed Non-Natural Aptamers Monoclonal, particle-displayed non-natural aptamers were generated by emulsion PCR. The oil phase was made up of 4.5% Span 80, 0.45% Tween 80, and 0.05% Triton X-100 in mineral oil, and all reagents were purchased from Sigma-Aldrich. The aqueous phase consisted of 1×KOD XL DNA polymerase buffer, 50 u KOD XL DNA polymerase, 0.2 mM dATP, 0.2 mM dGTP, 0.2 mM 2, 0.2 mM 1, 10 nM FP, 1 µM fluorescently labeled RP, ~1 µM template DNA, and ~$10^8$ 1 µm FP-conjugated magnetic beads. For each reaction, 1 mL of aqueous phase was added to 7 mL of oil phase and emulsified at 620 rpm for 5 min in an IKA DT-20 tube using the IKA Ultra-Turrax device. The emulsion was pipetted into 100 µL reactions in a 96 well plate. The following PCR conditions were used: 96° C., 2 min+[96° C., 15 s+52° C., 30 s+75° C., 60 s]*39+75° C., 5 min.

After PCR, the emulsions were collected into an emulsion collection tray (Life Technologies) by centrifuging at 300× g for 2 min. The emulsion was broken by adding 10 mL 2-butanol to the tray, and the sample was transferred to a 50 mL tube. The tube was vortexed for 30 s, and the particles were pelleted by centrifugation at 3,000×g for 5 min. The oil phase was carefully removed, and the particles were resuspended in 1 mL of emulsion breaking buffer (100 mM NaCl, 1% Triton X-100, 10 mM Tris-HCl, pH 7.5, and 1 mM EDTA) and transferred to a new 1.5 mL tube. After vortexing for 30 s and 90 s of centrifugation at 15,000×g, the supernatant was removed. The tube was placed on a magnetic separator (MPC-S, Life Technologies), and the remaining supernatant was removed. The particles were washed three times with 1×PBS buffer using magnetic separation, then stored in 200 µL PBST at 4° C.

For the click conjugation of 3, the particles were resuspended in 10 µL PBS. 20 mM sodium phosphate buffer, pH 7.3 was degassed for at least 15 min with N2 before preparing the reaction. The 10 µL bead suspension was combined with 25 µL 20 mM $Na_2HPO_4$ and 5 µL 10% Tween 20 in a 1.5 mL Eppendorf tube. The click reaction was initiated by the addition of 5 µL 2-azidoethyl 2,3,4,6-tetra-O-acetyl-α-D-mannopyranoside (AeMan, 100 mM in methanol) and 2.5 µL premixed solution of Cu:TBTA (10 mM, 1 mg Cu(I)Br+10 mM TBTA in 3:1 DMSO:tBuOH). The reaction was vortexed briefly, placed in a 20 mL vial with a septum, flushed with N2 for 5 min, and incubated in the dark with constant vortexing for 2 hours. The reaction tube was placed on the magnetic separator, and the supernatant was removed. The particles were washed 5 times with 50 µL TE buffer.

To generate single-stranded DNA, the particles were resuspended in 200 µL 0.1 M NaOH solution and incubated for 5 min at room temperature. The supernatant was removed using the magnetic separator, and the particles were resuspended in 200 µL concentrated ammonium hydroxide (18 M) to deprotect the AeMan. The particles were incubated for three hours on a slow rotator. The particles were washed five times with TE buffer and resuspended in 200 µL 10 mM Tris.

Example 7—Optimization of "Reverse-Transcription" of Particle-Displayed Non-Natural Aptamers Non-natural aptamer-displayed particles as templates were subjected to PCR with 1× polymerase buffer, 0.2 mM dATP, 0.2 mM dGTP, 0.2 mM dCTP, 0.2 mM dTTP, 0.4 µM T-FP, 0.4 µM T-RP, 0.05 U/µL DNA polymerase, $10^4$ non-natural aptamer (M1)-displayed particles, and water in a total volume of 50 µL. Cycling conditions were as follows: 96° C., 2 min+[96° C., 15 s+51° C., 30 s+72° C., 30 s]*30+72° C., 2 min+hold at 4° C.

Four DNA polymerases: Taq, KOD-XL, Pwo, and Deep Vent were screened for the efficiency of reverse transcription, 2 µL of each PCR reaction was loaded directly onto a 10% native PAGE gel and run at 150 V for 30 min in 1×TBE buffer. Gels were imaged after staining with 1× GelStar Nucleic Acid Stain in TBE buffer.

Example 8—Click-PD Screening

For ConA: For each round of screening, ~$10^8$ non-natural aptamer particles were incubated with 1 nM biotinylated ConA and 250 nM FTTC-conjugated PSA in selection buffer (SB; 1×PBS, 2.5 mM $MgCl_2$, 1 mM $CaCl_2$, 0.1 mM $MnCl_2$, 0.01% Tween 20) for 1 hour in the dark on a rotator. After incubation, the particles were resuspended in a 500-fold dilution of streptavidin-conjugated Alexa Fluor 647 to fluorescently label biotinylated ConA bound to the non-natural aptamer particles, and incubated for 10 min in the dark on a rotator. The particles were washed once and resuspended in SB. The sample was then analyzed with the BD FACS Aria III, and the sort gate was set to collect non-natural aptamer particles in quadrant IV, the population that exhibits high binding to ConA and low binding to PSA (FIG. 9A). 0.2-1% of the total singlet population was collected in each round. After sorting, the collected non-natural aptamer particles were resuspended in 20 µL PBS and reverse transcribed into canonical DNA by Taq polymerase.

For DC-SIGN: Prior to incubation with non-natural aptamer particles, human DC-SIGNR and mouse SIGNR1 were labeled with goat anti-human IgG Fc antibodies conjugated with DyLight 488 and DyLight 650, respectively. 10 µL of 2 µM human DC-SIGN/mouse SIGNR1 was incubated with 1 µL of 0.5 mg/mL DyLight 488/650 conjugated antibody in SB with a total volume of 100 µL for at least 1 hour in the dark on a rotator at 4° C. The labeled proteins with ~$10^8$ non-natural aptamer particles in SB were incubated for 1 hour in the dark on a rotator. The library, Round 1, and Round 2 non-natural aptamer particles were incubated with 10 nM human DC-SIGNR and 10 nM mouse SIGNR1. For Round 3, the concentration was dropped to 1 nM human DC-SIGNR and 1 nM mouse SIGNR1. After incubation, the particles were washed once and resuspended in SB. As in the ConA screen, the sample was then analyzed with BD FACS Aria III, and the desired non-natural aptamer particles were collected. In the first sort with the library non-natural aptamer particles, all particles with high binding to human DC-SIGNR (quadrants I and IV) were collected. In the subsequent three rounds of screening with Rounds 1, 2, and 3 particles, only particles exhibiting high binding to human DC-SIGNR and low binding to mouse SIGNR1 (quadrant IV) were collected. 0.2-1% of the total singlet population was collected in each round. After sorting, the non-natural aptamer particles were resuspended in 20 μL PBS and reverse transcribed into canonical DNA by Taq polymerase.

Example 9—High-Throughput Sequencing of the Enriched Libraries

Preparation of DNA pools for high-throughput sequencing was done by following the steps described in 16S Metagenomic Sequencing Library Preparation by Illumina. Overhang adaptor sequences for the forward and reverse primers were ordered from IDT. DNA pools from rounds 1, 2, and 3 were indexed using the Nextera XT DNA Library Preparation Kit (Illumina) and then pooled for sequencing. Sequencing was performed using an Illumina MiSeq at the Stanford Functional Genomics Facility. Sequences with low quality were filtered out using the "Filter by quality" Galaxy NGS tool, accepting only sequences with more than 90% of the bases having a quality score of 20 or above. For each round, 23-27% of the sequences were discarded because of low quality. The FASTAptamer toolkit was used to identify sequence clusters (sequences varying by 2 or fewer bases) and calculate the degree enrichment of each sequence from round to round.

Example 10—General Procedure for Particle-Based Binding Assay for Fluorescently Labeled Targets ~$10^6$ particles were incubated with varying concentrations of fluorescently labeled protein in SB for 1 hour on a rotator. After incubation, the particles were washed once and resuspended in SB. The particles were analyzed using the BD Accuri C6 flow cytometer, and the mean fluorescence and/or percentage of bound particles were measured in the relevant fluorescence channel(s).

Example 11—Generation of Solution-Phase Non-Natural Aptamers with 5'-Biotinylation PCR using modified substrates was performed in a PCR mixture containing 1×KOD-XL polymerase buffer, 0.2 mM dATP, 0.2 mM dGTP, 0.2 mM 2, 0.2 mM 1, 0.4 μM 5'-biotinylated C-FP-Bio, 0.4 μM C-RP, 0.05 U/μL KOD-XL DNA polymerase, 20 μM PCR template, and water in a total volume of 5 mL in a 96 well plate. Cycling conditions were as follows: 96° C., 2 min+[96° C., 15 s+52° C., 30 s+75° C., 30 s]*12+75° C., 2 min+hold at 4° C.

PCR reactions were transferred into a 50 mL conical tube. To this PCR mixture, 0.5 mL 3 M sodium acetate (pH 5.2) and 13.75 mL of 100% ethanol were added, followed by freezing at −80° C. for 30 min. The frozen stock was then centrifuged for 30 min at 5000 RPM at 4° C. to precipitate the DNA. The pellet was dissolved with 600 μL water, followed by purification using MinElute spin columns. The PCR product was eluted with 180 μL of 10 mM Tris buffer, pH 8.0. To this DNA solution, 40 μL of 3 M sodium acetate (pH 5.2) and 1.2 mL of 100% ethanol were added, followed by freezing at −80° C. for 30 min. The frozen stock was then centrifuged for 30 min at 21,000×g at 4° C. to precipitate the DNA. The DNA was resuspended in 20 μL 1×PBS buffer.

20 μL of the base-modified DNA solution was combined with 20 μL 100 mM 3 in DMSO (100 eq) and 40 μL 20 mM sodium phosphate buffer, pH 8 (pre-degassed by bubbling N2 through) in a 1.5 mL Eppendorf tube. Click chemistry was initiated by the addition of 20 μL of a premixed solution of 1:1 Cu:TBTA (10 mM, prepared with 1 mg CuBr+0.7 mL 10 mM TBTA in 4:3:1 water:DMSO:t-BuOH). The cap of the tube was removed, and the de-capped tube was immediately placed a 20 mL vial equipped with a rubber septum, followed by Ar flushing for 5 min. The sealed vial was incubated in the dark for two hours. To this DNA solution, 10 μL of 3 M sodium acetate (pH 5.2) and 330 μL of 100% ethanol were added, followed by freezing at −80° C. for 30 min. The frozen stock was then centrifuged for 30 min at 21,000×g at 4° C. to precipitate the DNA. The DNA was suspended in 350 μL 1× B&W.

350 μL MyOne C1 streptavidin beads were added to a 1.5 mL Eppendorf tube. The beads were captured on the side of the tube with a magnet and the supernatant was removed. The beads were washed three times with 350 μL 1× B&W. The click product sample was added to the beads and mixed on a rotator at room temperature for 30 min. The beads were then captured and the supernatant was discarded. The beads were washed three times with 350 μL 1× B&W, then treated twice with 100 μL 0.25 M freshly prepared NaOH solution to generate single-stranded DNA. The supernatant was discarded. Deprotection of the acetyl group on the mannose was effected by the addition of 300 μL of concentrated ammonium hydroxide (18 M) and incubation at room temperature for three hours. This tube was then sealed tightly before heating on a thermal block at 70° C. for 10 min. The sample was cooled in an ice bath before opening the cap. The tube was placed on the magnet, and the supernatant was transferred to a separate tube. 100 μL more ammonium hydroxide (18 M) was added to the beads, and the heating procedure was repeated once more.

The supernatants from the two ammonium hydroxide treatment steps were combined and then combined with 4.5 mL n-butanol before vortexing and centrifuging at 16,000×g at 4° C. for 10 min. The supernatant was removed and discarded. The sample was dried over vacuum centrifugation, and then resuspended in 100 μL water. To this solution, 50 uL of 5 M NH$_4$OAc and 415 μL of cold 100% ethanol were added before freezing at −80° C. for 30 min. The solution was centrifuged for 30 min at 21,000×g at 4° C. to precipitate the non-natural aptamer. The pellet was washed once with 70% cold ethanol in water, then dissolved in 100 μL water.

Figure 10A:
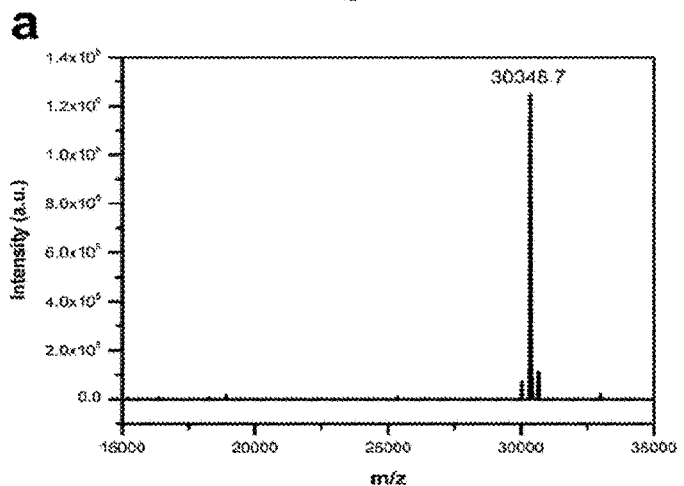
FIGS. 10A-10C: ESI-MS characterization of solution-phase 3-1, 3-1m, and D1 with 5'-biotinylation.
Figure 10B:
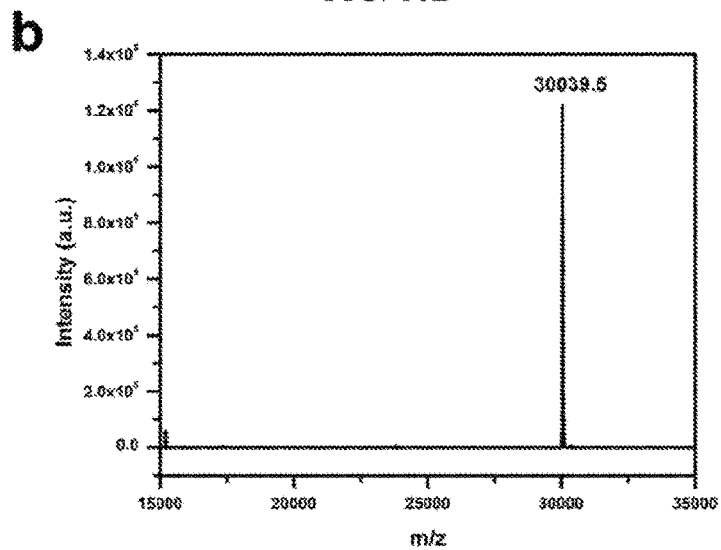
Figure 11A:
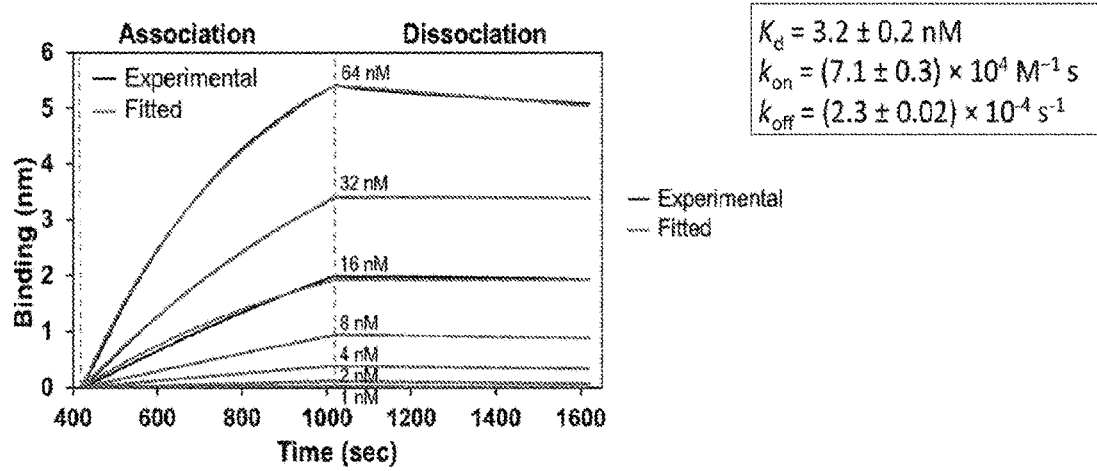
FIGS. 11A and 11B: BLI analysis of 3-1m and 3-1. Bio-layer interferometry (BLI) measurement of ConA interacting with surface-immobilized aptamers. Global fitting of target association and dissociation at each concentration was performed to generate Kd, kon, and koff values.
Figure 11B:
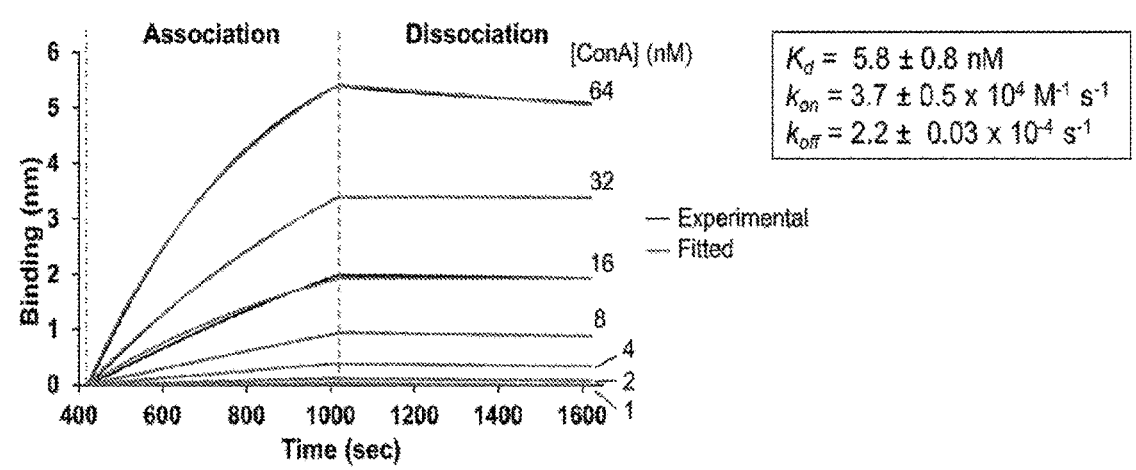

Example 12—Bio-Layer Interferometry Measurement of Selected Non-Natural Aptamers The binding characteristics of 3-1 and 3-1m was further validated using an alternative measurement method, bio-layer interferometry (BLI) (Abdiche et al., 2008). This allowed the confirmation that these binding results are independent of the particles on which the aptamers are immobilized, and to measure association rate (kon) and dissociation rate (koff) constants. Solution-phase non-natural aptamers were prepared using conventional PCR instead of emulsion PCR, with biotinylated FP instead of particle-conjugated FP and with ESI-MS confirmation after click conjugation with 3 (FIGS. 10A and 10B). Biotinylated 3-1 and 3-1m were immobilized onto the streptavidin-coated surface of the biosensor and incubated with ConA at various concentrations, followed by dissociation in blank buffer (FIG. 11A). For 3-1m, the resulting response curves were globally fitted for each concentration to generate rate constants of kon=(7.1±0.3)×104 M-1 s, and koff=(2.3±0.02)× 10-4 s-1, corresponding to a Kd of 3.2±0.2 nM. Notably, the off-rate (koff) of both 3-1 and 3-1m when bound to ConA was comparable to or lower than that of many antibody-antigen interactions (Ernst and Magnani, 2009; Steckbeck et al., 2005). The maximum response measurements were also fitted from each concentration to a cooperative binding model, yielding a $K_d$ of 5.3±0.7 nM for 3-1m. These affinity values are in reasonable agreement with the measurement from the particle-based binding assay. In comparison, the Kd of 3-1 for ConA is 5.8±0.8 nM by BLI (FIG. 11B), confirming that the substitution of dC with 2 does not enhance lectin binding, and indeed slightly reduces affinity in the BLI assay.

Figure 12A:
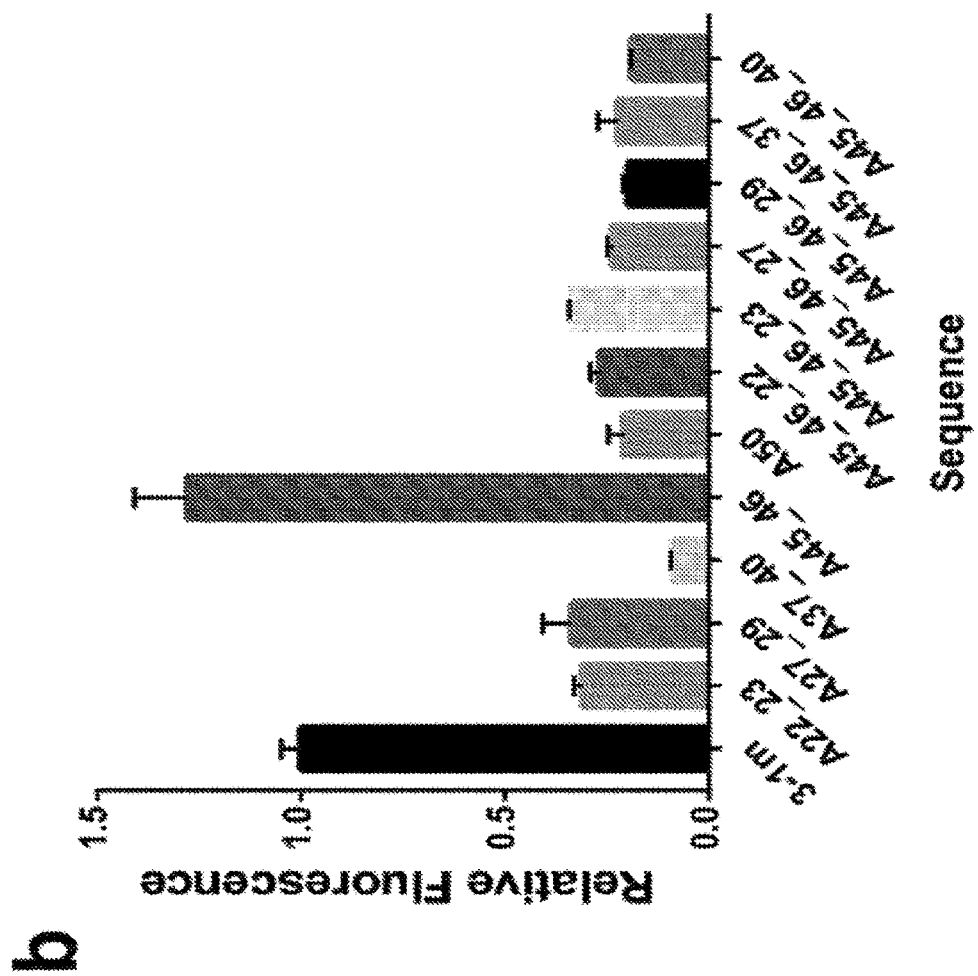
Figure 12B:
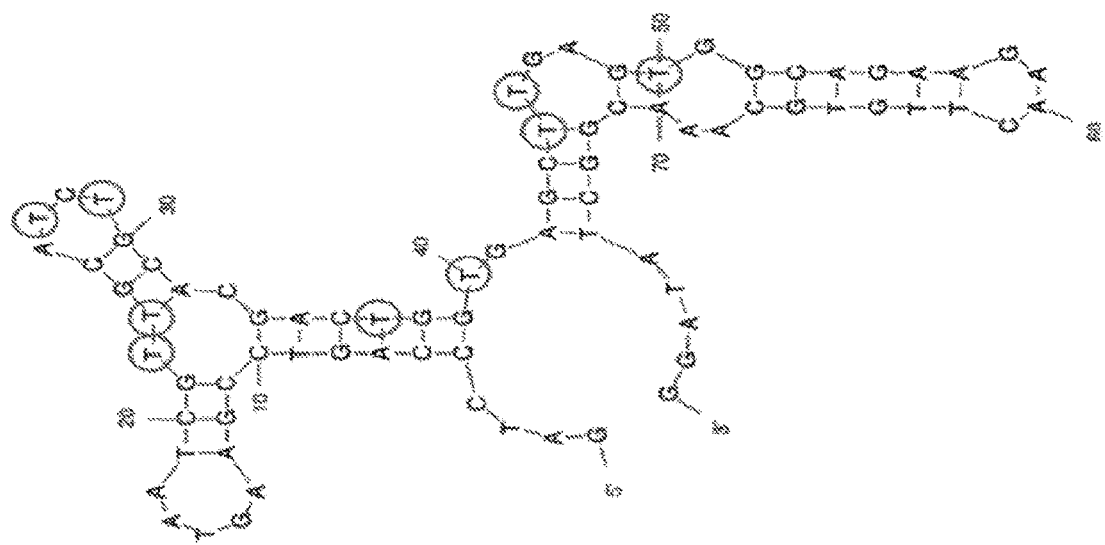
Figure 13:
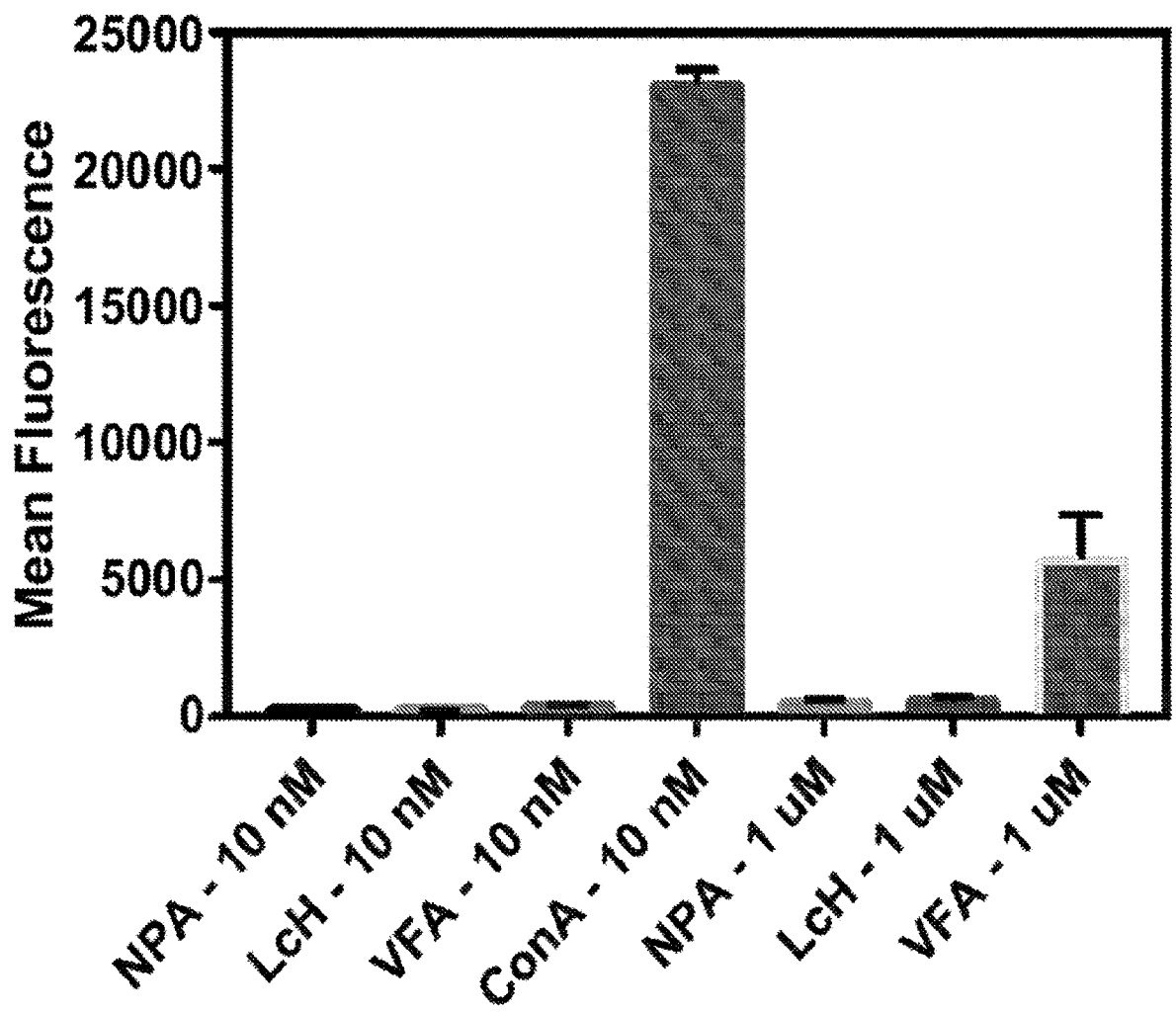
FIG. 13: 3-1m exhibits little binding to NPA, LcH, and VFA lectins. Particles coated with 3-1m were incubated with fluorescently-labeled mannose-binding lectins. These were then washed and analyzed by FACS based on mean fluorescence of the population. Error bars were derived from three experimental replicates.
Figure 14:
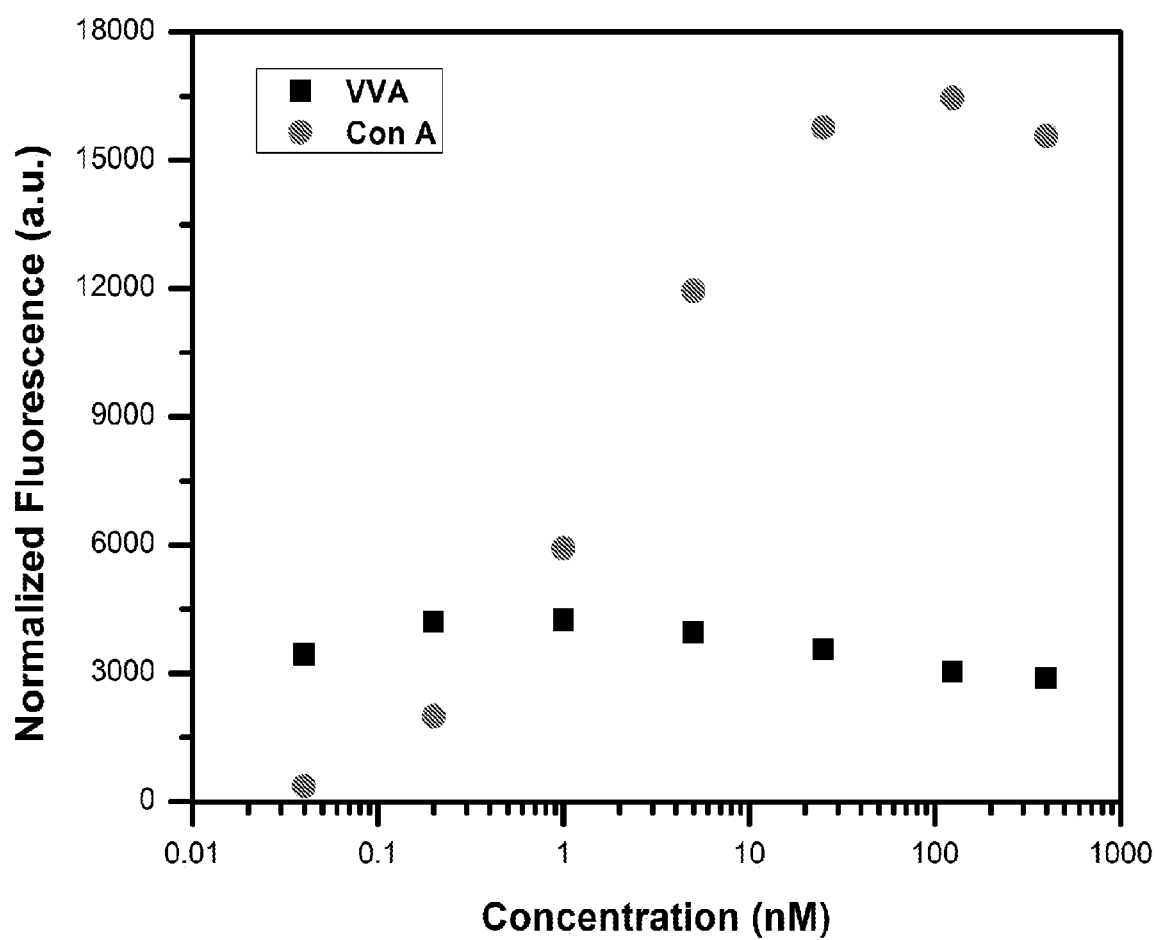
FIG. 14: Fluorescence intensity measurements of VVA and Con A on the lectin array. Even at low concentrations of fluorescently labeled 3-1m, the fluorescence intensity of the VVA spot is fairly high. The signal slightly decreases at higher concentrations of 3-1m. Overall, this change is not significant compared to the signals of Con A, which rises from near zero to ~18,000 a.u. over the concentration range from 40 pM to 400 nM. The VVA spot was therefore ruled a false positive.

To further determine the extent to which each mannose side chain contributes to 3-1m's interaction with ConA, particles displaying mutants of 3-1m in which either individual occurrences or pairs of nucleotide 4 within the sequence (excluding the primer region) were substituted with dA were generated, and screened their affinity for ConA (FIGS. 12A-12C). It was determined that essentially all of the mannose groups, with the exception of those at nucleotide positions 45 and 46, are critical for binding, and that the loss of even one mannose side-chain in the sequence significantly reduced the affinity of the mutant.

The experimental procedures used were described as follows. 3-1 and 3-1m were diluted to 50 nM in SB. Solutions of 0, 1, 2, 4, 8, 16, 32, and 64 nM ConA were prepared in SB. The solutions were loaded into a 384 well plate, with 100 μL of SB, 80 μL of biotinylated aptamer, and 100 μL of ConA solution for each reaction. The following steps were run on the ForteBIO Octet RED384 with Super Streptavidin biosensors: 60 s in buffer for equilibration, 5 min in aptamer solution to load the aptamer onto the biosensors, 60 s in buffer for a baseline measurement, 10 min in ConA solution to measure association, and 10 minutes in buffer to measure dissociation. Analysis was performed using Octet Data Analysis software, including the alignment of the different measurements and global fitting of the experimental data to a binding model to extract $K_d$, $k_{on}$, and $k_{off}$.

Example 13—Lectin Array Assay to Probe Non-Natural Aptamer Specificity

The following procedure was adapted from the vendor's product manual. First, the glass slide was dried. The slide with the pre-printed lectin array was equilibrated to room temperature inside the sealed plastic bag for 20-30 minutes. 30 μL 0.5 μM 3-1m in 1×PBS was annealed by incubating the solution at 95° C. and slowly cooling down to 4° C. at a ramp rate of 0.1° C./second. The solution was incubated at 4° C. for 5 min. 100 μL sample diluent (included in the lectin array package) was added into each well of the array and incubated at room temperature for 30 min to block the slides. The buffer was removed from each well. After diluting 3-1m to the desired concentration with SB, 100 μL of diluted 3-1m was added to each well and the arrays were incubated at room temperature for 3 hours. The samples from each well were removed, and each well was washed five times (5 min each) with 150 μL of 1× wash buffer I (included in the lectin array package, supplemented with 2.5 mM $MgCl_2$, 1 mM $CaCl_2$), and 0.1 mM $MnCl_2$) at room temperature with gentle shaking. The buffer was removed completely between each wash step. The samples were then washed two times (5 min each) with 150 μL of 1× wash buffer 11 (included in the lectin array package, supplemented with 2.5 mM $MgCl_2$, 1 mM $CaCl_2$, and 0.1 mM $MnCl_2$) at room temperature with gentle shaking. The wash buffer was completely removed between each wash step. The Cy3 equivalent dye-conjugated streptavidin tube (included in the lectin array package) was spun down, and 1.4 mL of sample diluent was added to the tube and mixed gently. 80 μL of Cy3 equivalent dye-conjugated streptavidin was added to each well and incubated in the dark at room temperature for 1 hour. The samples from each well were decanted, and washed five times with 150 μL of 1× wash buffer I at room temperature with gentle shaking. The wash buffer was completely removed after each wash step. The slide assembly was dissembled by pushing the clips outward from the slide side and carefully removing the slide from the gasket. The slide was placed in the slide washer/dryer (a four-slide holder/centrifuge tube included in the lectin array package), and enough 1× wash buffer I (about 30 mL) was added to cover the whole slide, and then the slide was gently agitated at room temperature for 15 minutes. After decanting wash buffer I, the slide was washed with 1× wash buffer H (about 30 mL) with gentle shaking at room temperature for 5 minutes. Finally, the slide was dried by centrifugation at 200×g on a microscope slide spinner and the slide was scanned on a microarray scanner, monitoring the Cy3 dye channel at PMT 500.

Example 14—ConA Aptamer Demonstrates Extraordinary Lectin-Specificity

Having shown 3-1m's strong specificity for ConA versus PSA, its ability to discriminate against a wide variety of other closely-related lectins that also preferentially bind mannose was also demonstrated. Plant-derived mannose-binding lectins such as *Lens cilinaris* agglutinin (LcH), *Narcissus pseudonarcissus* lectin (NPA), and *Vicia faba* agglutinin (VFA) all belong to the same carbohydrate specificity group as ConA and PSA and share high structural homology (Hemperly et al., 1979) and are therefore good models for testing specificity. Critically, 3-1m exhibited virtually no binding to LcH, NPA, or VFA at 10 nM. Even at a 100-fold higher concentration (1 μM) 3-1m showed little binding to LcH and NPA, and only modest binding to VFA (FIG. 13). This low level of binding to VFA at high concentrations can be attributed to the especially high degree of homology between ConA and VFA (Hemperly et al., 1979).

Next, the analysis of 3-1m was expanded to an extended group of 40 structurally related and unrelated lectins using a lectin array (FIGS. 9C and 9D). In addition to the lectins studied above, this array also included lectins belonging to different specificity groups with varying degrees of homology to ConA (Table 1). This assay further confirmed the remarkable specificity of 3-1m: across a broad range of concentrations from 0.04-400 nM, ConA was the only lectin that generated a strong signal. It should be noted that although VVA showed slightly higher signal than the other non-target lectins, this was subsequently determined to be a false positive. This array feature produced a significant signal even in the absence of 3-1m, and this signal did not increase at higher 3-1m concentrations (see FIG. 14 for details).

TABLE 1

Additional information on lectins spotted on the lectin array.
(Note: the following information is replicated from Lectin Array 40 product manual)

| Lectin | Abbreviation | Source | Carbohydrate Specificity |
|---|---|---|---|
| AIA | AIA | *Artocarpus integrifolia* (Jackfruit) seeds | αGal |
| *Aleuria aurantia* | AAL | *Aleuria aurantia* mushrooms | Fucα6GlcNAc |
| *Allium sativum* | ASA | *Allium sativum* agglutinin (Garlic) | αMan |
| *Amaranthus caudatus* | ACL, ACA | *Amaranthus caudatus* seeds | Galβ3GalNAc |
| *Anguilla anguilla* | AAA | *Anguilla anguilla* (Fresh Water Eel) | αFuc |
| *Bauhinia purpurea* | BPA, BLP | *Bauhinia purpurea alba* (Camel's Foot Tree) seeds | Galβ3GalNAc |
| Concanavalin A | Con A | *Canavalia ensiformis* (Jack Bean) seeds | αMan, αGlc |
| *Datura stramonium* | DSA, DSL | *Datura stramonium* (Thorn Apple, Jimson Weed) seeds | (GlcNAc)$_{2-4}$ |
| *Dolichos biflorus* | DBA | *Dolichos biflorus* (Horse Gram) seeds | αGalNAc |
| *Erythrina cristagalli* | ECA, ECL | *Erythrina cristagalli* (Coral Tree) seeds | Galβ4GlcNAc |
| *Euonymus europaeus* | EEL | *Euonymus europaeus* (Spindle Tree) seeds | Galα3Gal |
| *Galanthus nivalis* | GNA, GNL | *Galanthus nivalis* (Snowdrop) bulbs | αMan |
| *Griffonia (Bandeiraea) simplicifolia* I | GS-I, GSL-I, BSL-I | *Griffonia (Bandeiraea) simplicifolia* seeds | αGal, αGalNAc |
| *Griffonia (Bandeiraea)* | GS-II, GSL-II, BSL-II | *Griffonia (Bandeiraea) simplicifolia* seeds | α or βGlcNAc |
| *Hippeastrum* hybrid | HHA, HHL, AL | *Hippeastrum* hybrid (Amaryllis) bulbs | αMan |
| Jacalin | Jacalin, AIL | *Artocarpus integrifolia* (Jackfruit) seeds | Galβ3GalNAc |
| *Lens culinaris* | LcH, LCA | *Lens culinaris* (lentil) seeds | αMan, αGlc |
| *Lotus tetragonolobus* | Lotus, LTL | *Lotus tetragonolobus, Tetragonolobus purpurea* (Winged Pea, Asparagus Pea) seeds | αFuc |
| *Lycopersicon esculentum* | LEA, LEL, TL | *Lycopersicon esculentum* (tomato) fruit | (GlcNAc)$_{2-4}$ |
| *Maackia amurensis* I | MAA, MAL, MAL-I | *Maackia amurensis* seeds | Galβ4GlcNAc |
| *Maclura pomifera* | MPL, MPA | *Maclura pomifera* (Osage Orange) seeds | Galβ3GalNAc |
| *Narcissus pseudonarcissus* | NPA, NPL, DL | *Narcissus pseudonarcissus* (Daffodil) bulbs | αMan |
| Peanut | PNA | *Arachis hypogaea* peanuts | Galβ3GalNAc |
| *Phaseolus lunatus* | LBA | *Phaseolus lunatus* (Lima Bean) seeds | GalNAcα(1,3)[Fucα(1,2)]Gal |
| *Phaseolus vulgaris* Erythroagglutinin | PHA-E | *Phaseolus vulgaris* (Red Kidney Bean) seeds | Galβ4GlcNAcβ2Manα6(GlcNAcb4)(GlcNAcβ4Manα3)Manβ4 |
| Leucoagglutinin | PHA-L | *Phaseolus vulgaris* (Red Kidney Bean) seeds | Galβ4GlcNAcβ6(GlcNAcβ2Manα3)Manα3 |
| *Pisum sativum* | PSA, PEA | *Pisum sativum* (Pea) seeds | αMan, αGlc |
| *Psophocarpus* | PTL, PTL-I, WBA-I | *Psophocarpus tetragonolobus* (Winged Bean) seeds | GalNAc, Gal |
| *Sambucus nigra* I | SNA-I | *Sambucus nigra* (Elderberry) bark | NANAα(2,6)GalNAc > GalNAc = Lac > GalNANAα(2,6)Gal |
| *Sambucus nigra* II | SNA-II | *Sambucus nigra* (Elderberry) bark | GalNAc > Gal |
| *Solanum tuberosum* | STL, PL | *Solanum tuberosum*, (potato) tubers | (GlcNAc)$_{2-4}$ |
| *Sophora japonica* | SJA | *Sophora japonica* (Japanese Pagoda Tree) seeds | βGalNAc |
| Soybean | SBA | *Glycine max* (soybean) seeds | a > βGalNAc |
| *Ulex europaeus* I | UEA-I | *Ulex europaeus* (Furze Gorse) seeds | αFuc |
| *Ulex europaeus* II | UEA-II | *Ulex europaeus* (Furze Gorse) seeds | Poly β(1,4)GlcNAc |
| *Urtica dioica* | UDA | *Urtica dioica* (Stinging Nettle) seeds | GlcNAc |
| *Vicia faba* | VFA | *Vicia faba* (Fava Bean) seeds | αMan |
| *Vicia villosa* | WA, WL | *Vicia villosa* (Hairy Vetch) seeds | GalNAc |
| Wheat Germ | WGA | *Triticum vulgaris* (wheat germ) | GlcNAc |
| *Wisteria floribunda* | WFA | *Wisteria floribunda* (Japanese Wisteria) seeds | GalNAc |

Figure 15A:
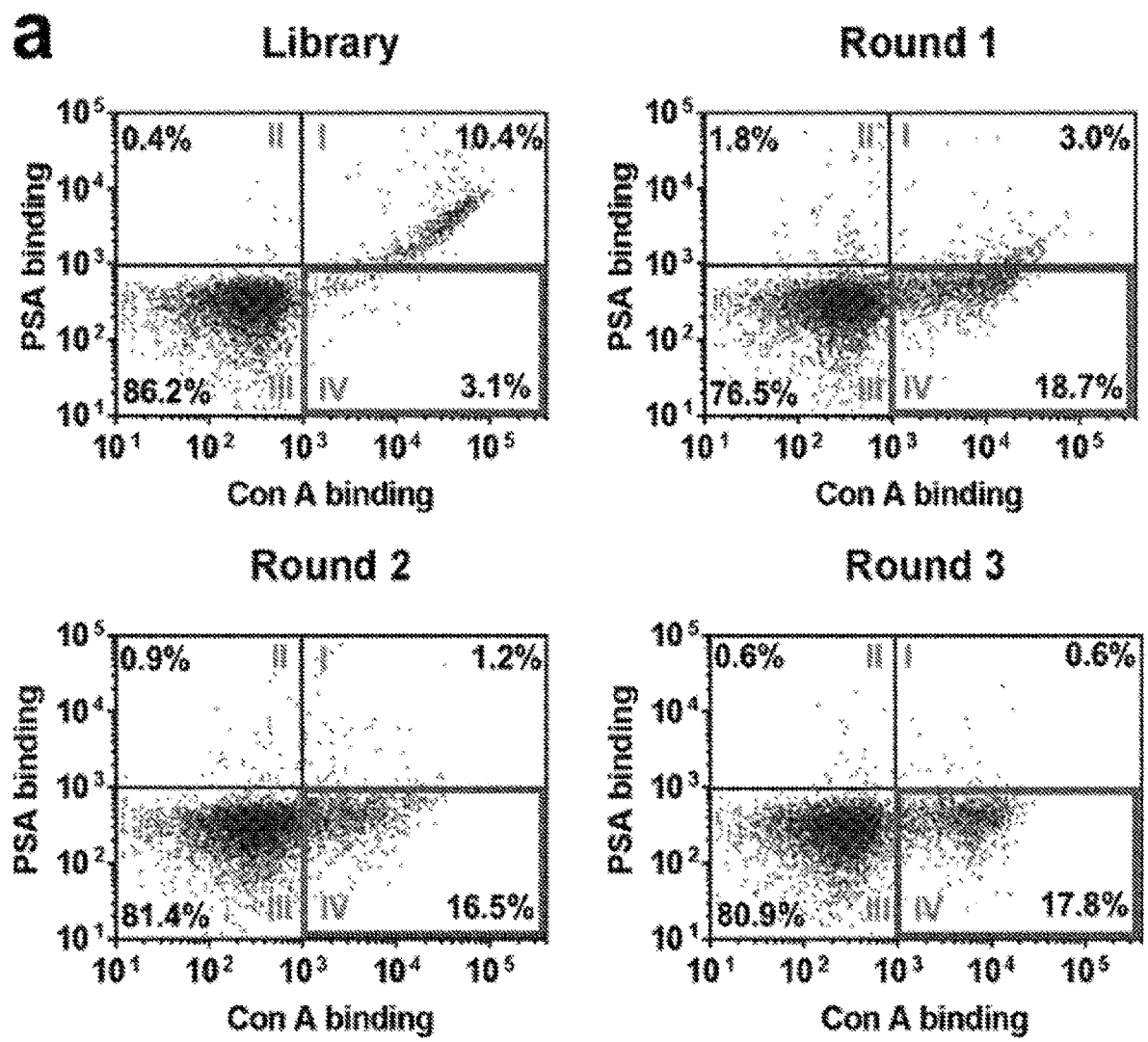
FIGS. 15A and 15B: Click-PD screening generates non-natural aptamers with high affinity and specificity for Con A.

Sugar Abbreviations
Fuc: L-Fucose   Gal: D-Galactose   GalNAc: N-Acetylglactosamine   Glc: D-Glucose
GlcNAc: N-Acetylglucosamine   Lac: Lactose   Man: Mannose Example 15—Click-PD Screening for Highly Specific ConA Non-Natural Aptamers For the ConA screen, ~10$^8$ non-natural aptamer-displaying particles were used. A fraction of this starting population already had strong affinity for ConA at a concentration of 1 nM (FIG. 15A); however, the majority of these initial derivatives were lacking in specificity, as shown by the significant binding to PSA. This lack of specificity was expected, given that both lectins bind strongly to mannose. Three rounds of screening were performed, collecting only the particles that exhibited strong ConA binding without binding PSA (FIG. 15A). A clear increase in the specificity of the selected particles was observed from round to round, and by the end of Round 3, 17.8% of the population bound strongly to 1 nM ConA without binding to PSA, even in the presence of a 250-fold higher concentration of the competitor.

Figure 15B:
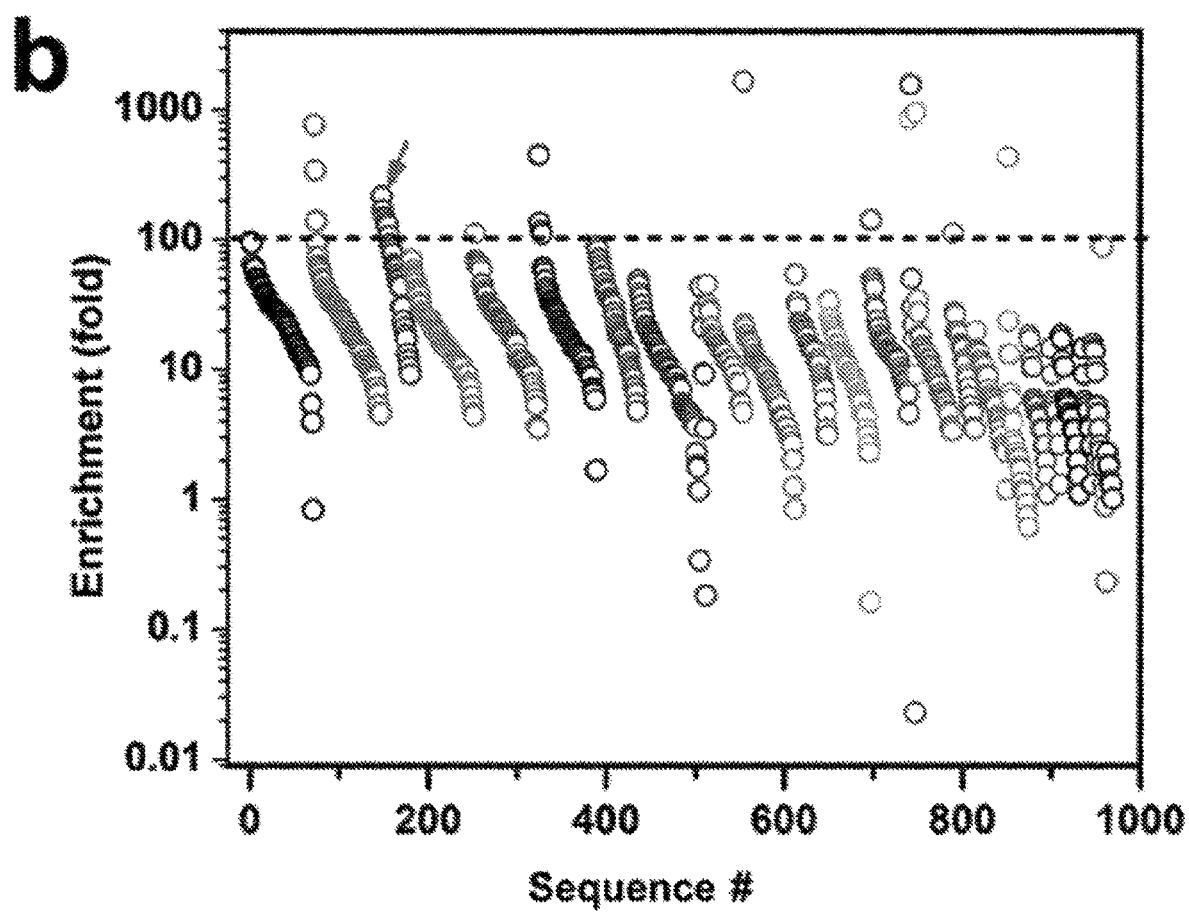
Figure 16:
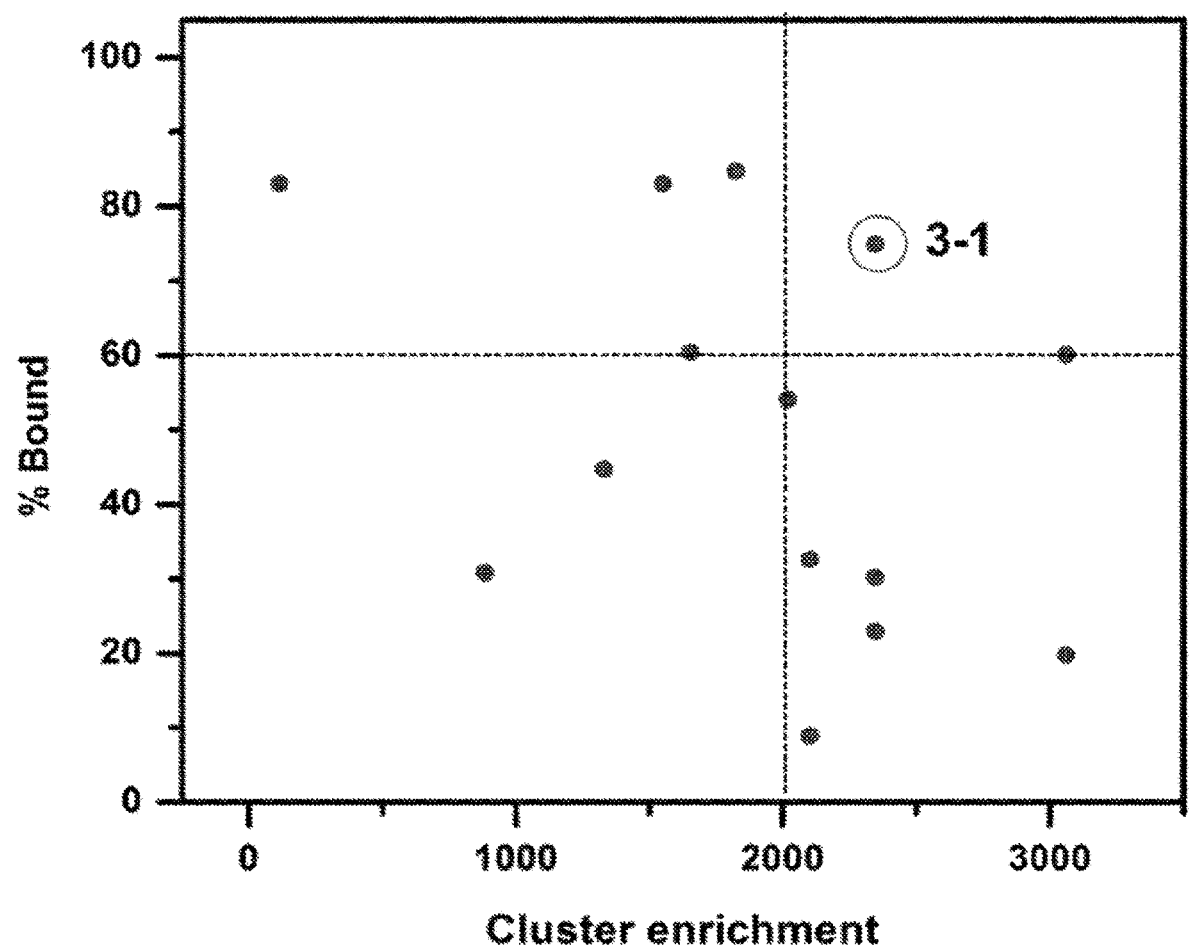
FIG. 16: Binding of selected sequences to fluorescently labeled ConA in a particle-based assay. Two criteria were considered to identify the top-performing non-natural aptamer. First, over 60% of non-natural aptamer-displaying particles bound ConA in a particle-based fluorescent assay. Second, the non-natural aptamer should originate from a cluster that has undergone >2,000 enrichment. 3-1 met both of these criteria.

High-throughput sequencing of the Round 1, 2, and 3 pools was performed to identify sequences that had become highly enriched during the Click-PD process. After filtering out low-quality sequences (where >10% of bases had a quality score ≤20) using Galaxy NGS tools (see Methods), 182,499 unique sequences (684,179 reads) were obtained in the Round 1 pool, 150,680 unique sequences (643,462 reads) were obtained in the Round 2 pool, and 2,867 unique sequences (470,426 reads) were obtained in the Round 3 pool. 132 sequence clusters were identified, defined as groups of closely-related sequences that differ from one another by two or fewer mutations (Alam et al., 2015) in the Round 3 pool. The degree of enrichment from Round 1 to Round 3 varied for the sequences within each cluster, with some of the most enriched clusters containing sequences that had undergone 100-fold to >1000-fold enrichment (FIG. 15B). 14 sequences exhibiting >100-fold enrichment were selected for further testing. Particles displaying each of these sequences were synthesized and their fluorescence intensity was measured after incubating with 1 nM ConA (Table 2). Sequence 3-1 (Table 3) was selected for further characterization due to its strong binding to ConA and the fact that it belonged to a highly enriched (>2,000-fold) sequence cluster (FIG. 16).

TABLE 2

Selected sequences from high-throughput DNA sequencing for binding analysis.

| Sequence | Random region only |
|---|---|
| 1-1 | TATCATGGACTATACGGAGGTAGATCGGATATGCGAACCA (SEQ ID NO: 16) |
| 2-1 | CTCCGCGGATCAATGCAGAGGATTGCAGATCCTCGACATG (SEQ ID NO: 17) |
| 2-2 | CTTCGCGGATCAATGCAGAGGATTGCAGATCCTCAACATG (SEQ ID NO: 18) |
| 3-1 | GTTGCATCTGCACGACTGGTGAGCTTGAGTGGCAGAAGAA (SEQ ID NO: 19) |

TABLE 2 -continued

Selected sequences from high-throughput DNA sequencing for binding analysis.

| Sequence | Random region only |
|---|---|
| 3-2 | GTTGCATCTGCACTACTGGTGAACTTGAGTGGCAGAAGAA (SEQ ID NO: 20) |
| 3-3 | GTTGCATCTGCACGACTGGTGAACTTGAGTGGCAGAAGAA (SEQ ID NO: 21) |
| 4-1 | AGCGATAGGTGCACTGGGGTCCTCTAAGCGCGTTAACGAG (SEQ ID NO: 22) |
| 5-1 | TAGTACGGAGGAACGTGCGAGCGGTAGCATTATAGCGAGA (SEQ ID NO: 23) |
| 6-1 | CACGTACTGCTACGGGGAGGGAGGTATCTGTCGCGGA (SEQ ID NO: 24) |
| 6-2 | CACGTACTGCTACGGGAAGGGAGGTATCTGTCGCGGA (SEQ ID NO: 25) |
| 7-1 | TCTGTGACGGTACGTCGCTGGAAGAAGTTGGGACGTATTA (SEQ ID NO: 26) |
| 9-1 | GAAGCAAGTTGGTCTTTAACGATACAACAGCTTGCGGAAC (SEQ ID NO: 27) |
| 11-1 | GGAGGTGTTACTGGCCGGGGAAGATTGAGGGTGGCGTGG (SEQ ID NO: 28) |
| 17-1 | GTTGAATCTGGATACGATTTCTGAGTTCTTAATGGGAAGA (SEQ ID NO: 29) |

TABLE 3 DNA sequences

| Name | DNA sequence |
|---|---|
| | Oligos used in Click-PD optimization |
| S1 | 5'-GG AAC GTC 111 GTA ACT TGA-3' (SEQ ID NO: 30) |
| T1 | 5'-ATC CAG AGT GAC GCA GCA MG AAC GTC TTT GTA ACT TGA AAT ACC GTG GTA GGT TGG CTA GGT TGG ACA CGG TGG CTT AGT-3' (SEQ ID NO: 31) |
| M1 | 5'-ATC CAG AGT GAC GCA GCA 2GG AA2 G42 444 G4A A24 4GA AA4 A22 G4G GCA GG4 24A GG4 4GG A2A 2GG 4GG 244 AG4-3' (SEQ ID NO: 32) |
| T-FP | 5'-ATC CAG AGT GAC GCA GCA-3' (SEQ ID NO: 33) |
| T-RP | 5'-ACT AAG CCA CCG TGT CCA-3' (SEQ ID NO: 34) |
| T-RP-2Bio | 5'-/52-Bio/ACT AG CCA CCG TGT CCA-3' (SEQ ID NO: 35) |
| | Oligos used in Click-PD screens |
| C-Lib | 5'-GAT CCC AGT CCG AAG TAA TCN NNN NNN NNN NNN NNN NNN NNN NNN NNN NNN NNN NNN CTT GTG CAA ACG GCT ATA GG-3' (SEQ ID NO: 36) |
| C-FP | 5'-GAT CCC AGT CCG AAG TAA TC-3 (SEQ ID NO: 37) |
| C-FP-Bio | 5'-/5BiotinTEG/GAT CCC AGT CCG AAG TAA TC-3' (SEQ ID NO: 38) |
| C-RP | 5'-CCT ATA GCC GTT TGC ACA AG-3' (SEQ ID NO: 39) |
| 3-1 | 5'-GAT CCC AGT CCG AAG TAA TCG 44G 2A4 24G 2A2 GA2 4GG 4GA G24 4GA G4G G2A GAA GAA 244 G4G 2AA A2G G24 A4A GG-3' (SEQ ID NO: 40) |
| 3-1m | 5'-GAT CCC AGT CCG AAG TAA TCG 44G CA4 C4G CAC GAC 4GG 4GA GC4 4GA G4G GCA GAA GAA C44 G4G CAA ACG GC4 A4A GG-3' (SEQ ID NO: 41) |
| 3-1a | 5'-GAT CCC AGT CCG AAG TAA TCG TTG 2AT 2TG 2A2 GA2 TGG TGA G2T TGA GTG G2A GAA GAA 2TT GTG 2AA A2G G2T ATA GG-3' (SEQ ID NO: 42) |
| 3-1nc | 5'-GAT CCC AGT CCG AAG TAA TCG 11G 2A1 21G 2A2 GA2 1GG 1GA G21 1GA G1G G2A GAA GAA 211 G1G 2AA A2G G21 A1A GG-3' (SEQ m NO: 43) |

-continued

TABLE 3 DNA sequences

| Name | DNA sequence |
|---|---|
| 3-1n | 5'-GAT CCC AGT CCG AAG TAA TCG TTG CAT CTG CAC GAC TGG TGA GCT TGA GTG GCA GAA GAA CTT GTG CAA ACG GCT ATA 6G-3' (SEQ ID NO: 44) |
| 3-1mscr | 5'-GAT CCC AGT CCG AAG TAA TCA GCA G44 AA4 G44 AGG A4G CGG AGG CGC A4A CG4 CG4 ACG C44 G4G CAA ACG GC4 A4A GG-3' (SEQ ID NO: 45) |
| CT | 5'-GAT CCC AGT CCG AAG TAA TCC CCC C4C CC4 CCC 4CC C4C CC4 CCC 4CC C4C CC4 CCC 4CC C44 G4G CAA ACG GC4 A4A GG-3' (SEQ ID NO: 46) |
| D1 | 5'-GAT CCC AGT CCG AAG TAA TCC AAG GG4 AA4 4GG GAA A4A AGG A4G GGG 4AA 4A4 GCA ACC C44 64G CAA ACG GC4 A4A GG-3' (SEQ ID NO: 47) |

Figure 9A:
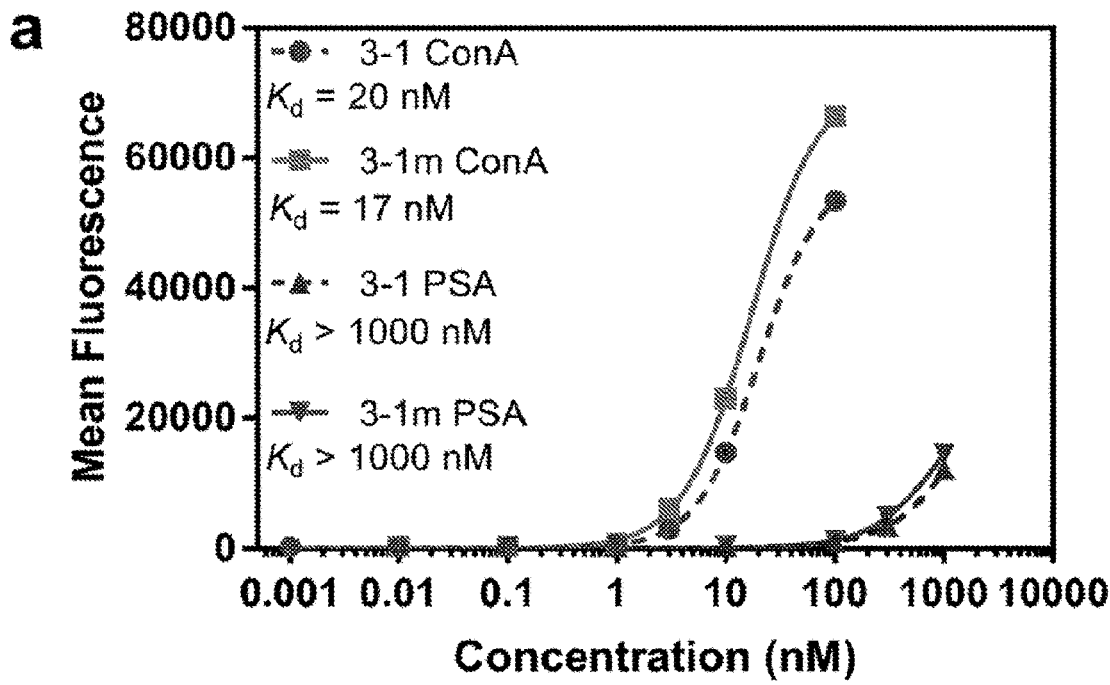
FIGS. 9A-9D: Affinity and specificity of Con A aptamers.

Example 16—Non-Natural Aptamer 3-1 Exhibits High Affinity and Specificity for ConA 3-1 bound strongly to ConA, and also exhibited remarkably high specificity for this particular lectin. Particles displaying 3-1 were incubated with different concentrations of fluorescently-labeled ConA and PSA, and measured the proportion of particles with high fluorescence intensity using FACS. A binding isotherm was established by plotting the percentage of target-bound particles over the total population at each lectin concentration. This revealed strong affinity for ConA ($K_d$=20 nM), with a much weaker affinity for PSA ($K_d$>1000 nM), clearly demonstrating the excellent specificity of this molecule (FIG. 9A).

As 3-1 contains multiple modifications, the next objective was to determine the extent to which these modifications contribute to its strong and specific interaction with ConA. Particles displaying various mutant sequences were synthesized based on 3-1 with different modification profiles (Table 3). 3-1a no longer contained 4, but still had dC substituted with 2, displaying aldehyde groups. On the other hand, 3-1m lacked 2 but still had dT substituted with 4. A construct composed entirely of canonical bases (3-1n) was prepared, as well as a version of 3-1 that was not subjected to subsequent click conjugation of 3 (3-1nc). Finally, to confirm that the affinity of 3-1 is sequence-specific, a 'CT-only' sequence was prepared that was the same length as 3-1 but only contained dC and 4, where the number of 4 nucleotides was equal to that of 3-1 (CT). A sequence with the same nucleotide composition as 3-1m but in a scrambled order (3-1mscr) was also prepared.

Figure 9B:
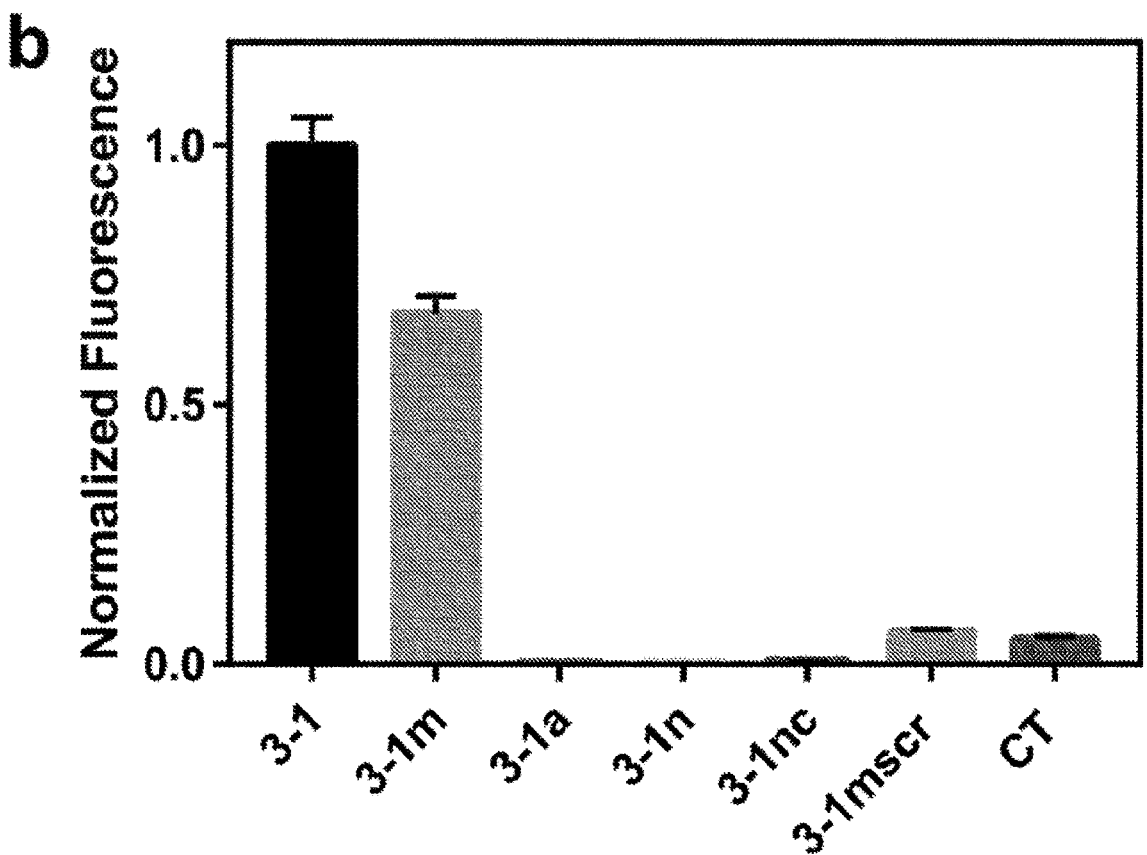
Figure 9C:
Figure 9D:
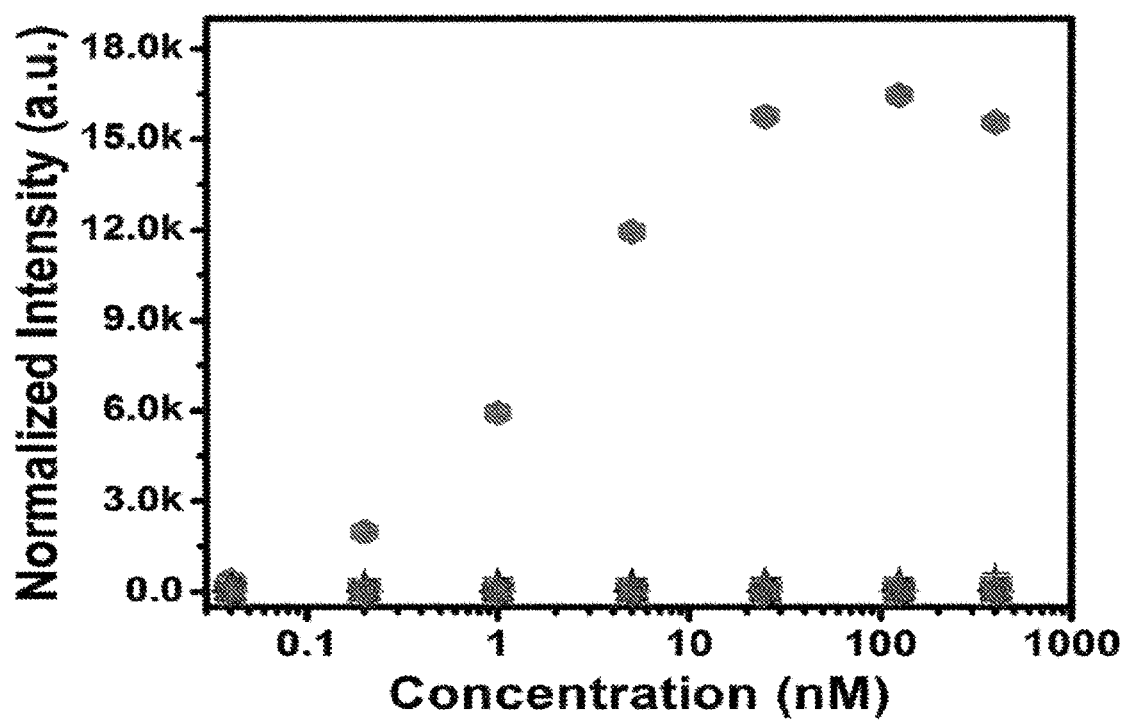

3-1a, 3-1n, and 3-1nc showed essentially no binding to 10 nM ConA (FIG. 9B), indicating that ConA binding was mannose-dependent. Both CT and 3-1mscr showed only low levels of binding to 10 nM ConA, which is most likely attributable to the presence of the mannose functional groups in this polymer. Notably, 3-1m showed only slightly lower levels of binding to 10 nM ConA than 3-1, despite the absence of aldehyde modifications (FIG. 9B). This unexpected finding prompted the further investigation of 3-1m's binding profile. It was determined that the affinity of 3-1m for ConA is in fact slightly superior to 3-1 ($K_d$=17 nM), and that the absence of modified nucleotide 2 did not affect 3-1m's specificity against PSA ($K_d$>1000 nM) (FIG. 9A). This indicates that the aldehyde functional groups do not contribute meaningfully to 3-1's affinity or specificity, and that only the mannose modifications are absolutely required for binding to ConA.

Example 17—Non-Natural Aptamers can Discriminate Human from Mouse DC-SIGN

Having demonstrated the capabilities of Click-PD with ConA, a similar strategy was used to target a mammalian protein with relevance to therapeutic applications. DC-SIGN, a C-type lectin present on the surface of dendritic cells that recognizes highly glycosylated viral envelope proteins, was selected. This binding event allows viruses such as human immunodeficiency virus (HIV) and Ebola to enter and infect dendritic cells (Alvarez et al., 2002; Geijtenbeek et al., 2000; Illescas et al., 2017). The human and mouse DC-SIGN proteins are closely related, with 57% sequence homology, and no previous affinity reagents have shown the capacity to distinguish between the two (Caminschi et al., 2006).

Figure 10C:
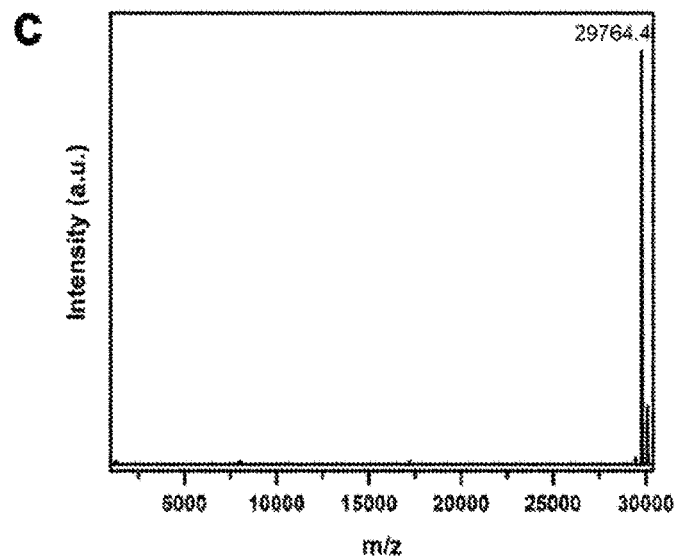
Figure 17A:
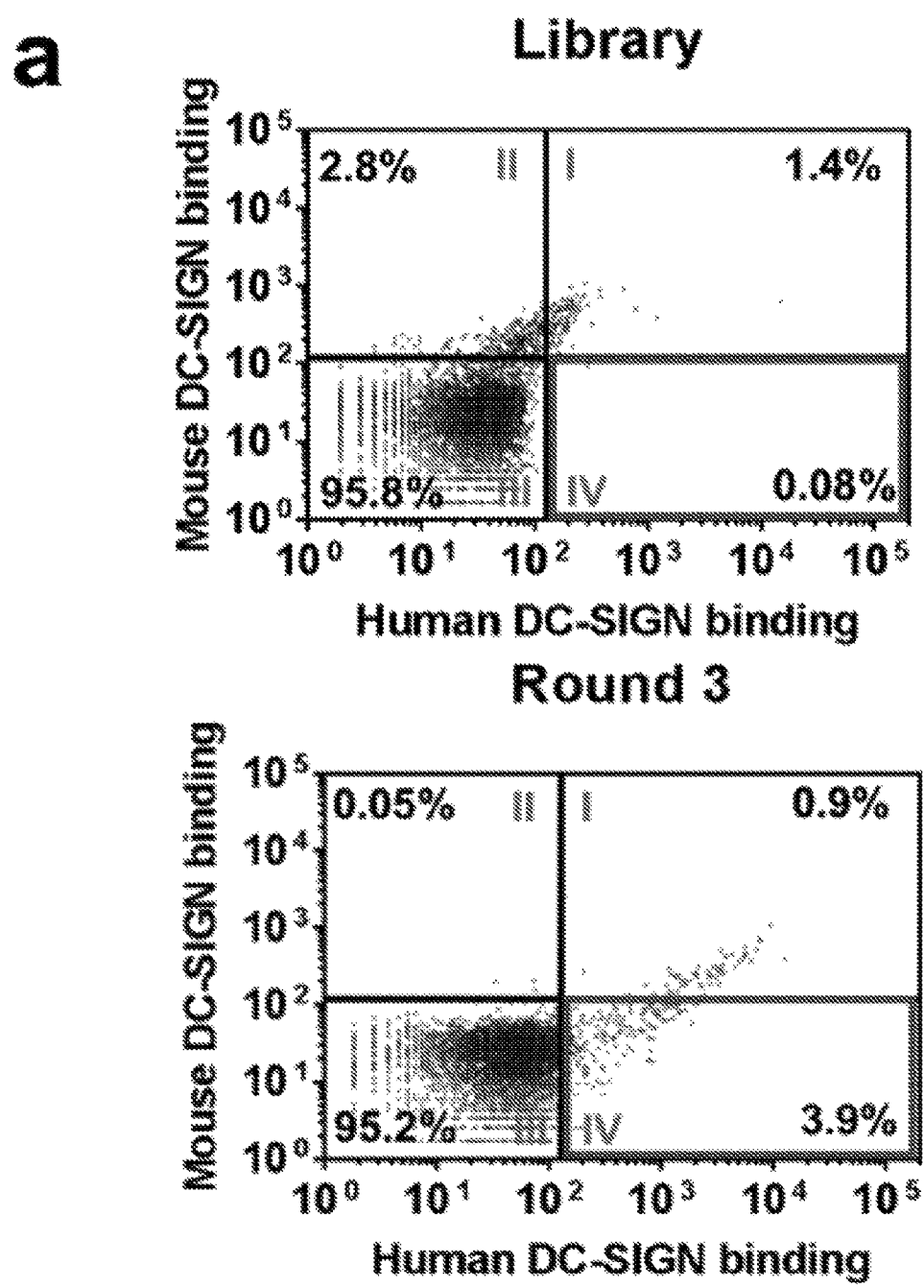
FIGS. 17A and 17B: Affinity and specificity of a DC-SIGN non-natural aptamer, D1.
Figure 17B:
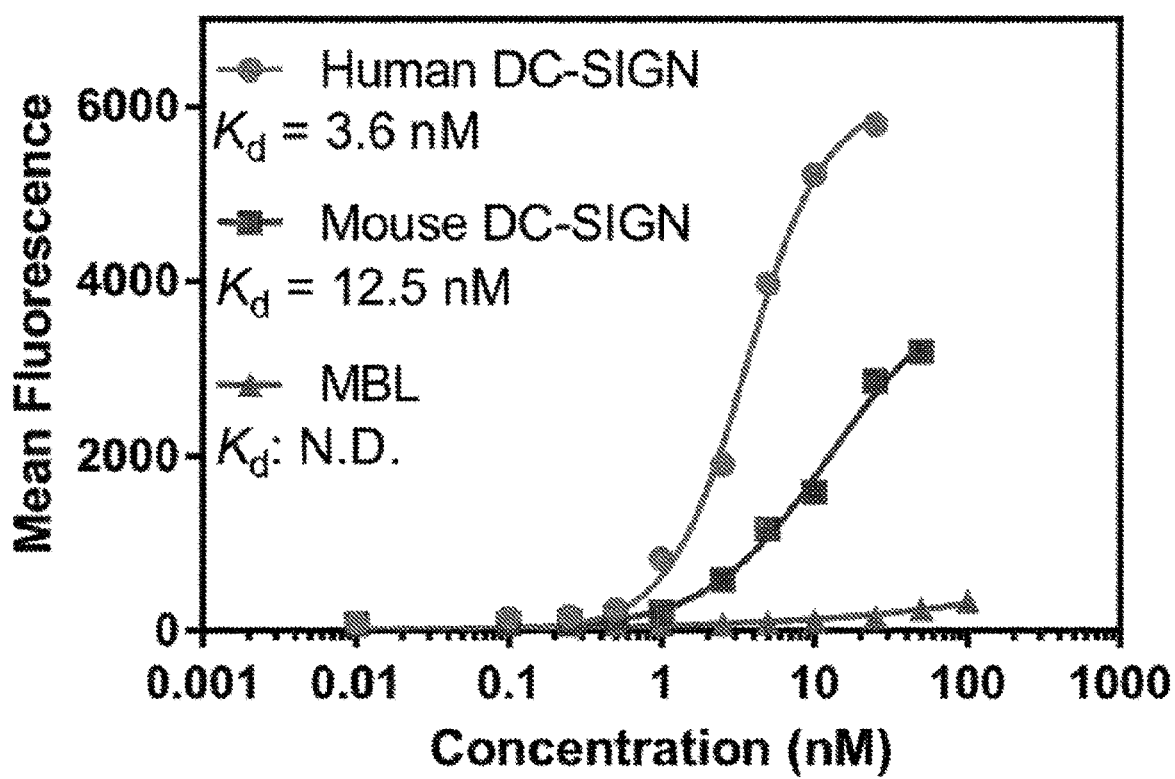
Figure 18:
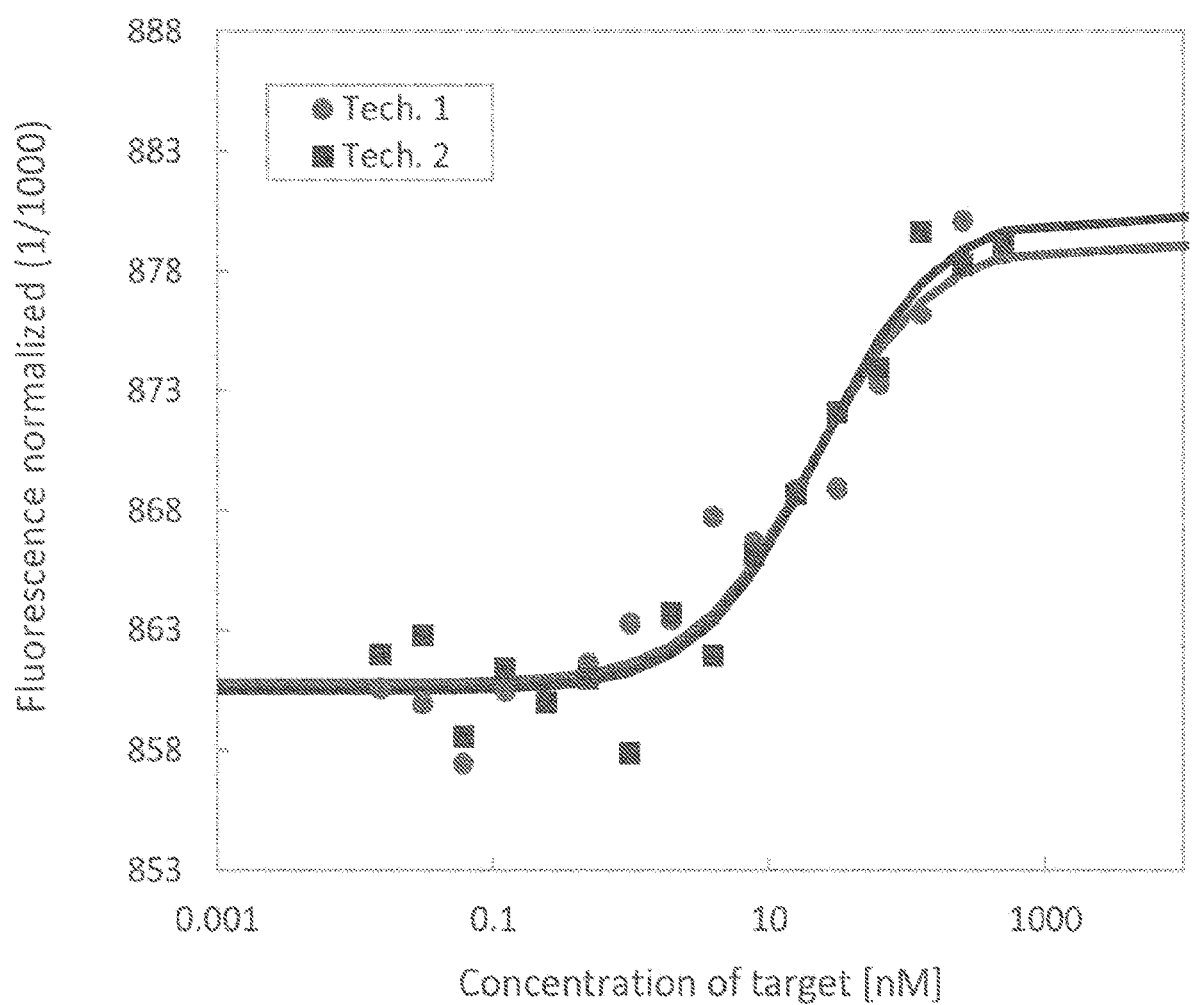
FIG. 18: Microscale thermophoresis (MST) analysis of D1. The experiment was conducted using fluorescently labeled DC-SIGN and free D1 in solution in two independent technical repeats, which yielded measured Kd of 20.4 nM and 22.7 nM. The average value of Kd=21.5 nM was adopted as the final result of the MST assay.

Using Click-PD, non-natural aptamers with remarkable specificity, which proved capable of distinguishing between these two highly similar targets, were produced. Three rounds of Click-PD were performed, enriching non-natural aptamer particles that exhibit higher affinity to human DC-SIGN and purging those binding to mouse DC-SIGN (FIG. 17A). For the initial library of non-natural aptamer particles, only 0.08% bound to human DC-SIGN and 2.8% bound to the mouse analogue. After three rounds of selection, 3.9% of the aptamer particles bound to human DC-SIGN, with only 0.05% of the aptamer particles binding to mouse DC-SIGN. High-throughput sequencing revealed a single sequence that underwent 1,300-fold enrichment over the course of those three rounds, D1. Affinity measurement with particles displaying D1 and fluorescently-labeled human and mouse DC-SIGN indicated a Kd of 3.6 nM for human DC-SIGN and 12.5 nM for mouse DC-SIGN (FIG. 17B). This 3.5-fold difference in binding affinity is striking, given the high degree of homology between the two proteins. Additionally, D1 exhibited essentially no binding to a lower-homology C-type lectin, mannose-binding lectin (MBL, FIG. 17B) at concentrations ranging from 0.1 to 100 nM. Solution-phase D1 (FIG. 10C) was subsequently generated and the binding affinity of D1 to human DC-SIGN was confirmed using microscale thermophoresis (MST), yielding a Kd of 21.5 nM (FIG. 18). The difference in measured Kd values between the particle-based binding assay and the MST method is within the level of variation previously seen across different methods for affinity measurements (Fei et al., 2011; Jing and Bowser, 2011; Sun et al., 2008).

Example 18—Microscale Thermophoresis Measurement of Non-Natural Aptamer

Biotinylated D1 was prepared by PCR amplification, click conjugation, single strand generation, and acetyl deprotection as described above. 25 µL of 3.9 µM D1, 60 µL of 2 µM DC-SIGNR, and 25 mL of SB were sent to 2bind for analysis. At 2bind, the samples were analyzed on a Monolith NT.115 Pico at 25° C., with 40% LED power and 40% laser power. The concentration of fluorescently labeled DC-SIGNR was held constant at 1 nM, and the concentration of D1 ranged from 30.6 µM to 1 µM. Two technical repeats were performed, and the Kd was calculated based on a 1:1 binding model.

Example 19—Determining ConA Concentration to Induce Complete Hemagglutination

Human erythrocytes were washed and resuspended in 1×PBS in a 96-well U-shaped well plate at 1% hematocrit, with ConA concentrations ranging from 250 µg/mL to 2 sg/mL. The plate was let stand at room temperature for 1 hour before visualizing the deposition of erythrocytes at the bottom of the well. The optical densities at 655 nm of the cell suspensions were then measured on a plate reader.

Example 20—Hemagglutination Inhibition Assay

30 µL 0.5 µM 3-1m was annealed in 1×PBS by heating the solution to 95° C. and slowly cooling down to 4° C. at a ramp rate of 0.1° C./second, followed by incubation at 4° C. for 5 min. The annealed non-natural aptamer was incubated at a range of concentrations from 9.6 nM to 300 nM with 150 nM ConA in 1×PBS for 30 min in a 96-well U-shaped well plate. Human erythrocytes were added to produce a cell suspension of 1% hematocrit in a total volume of 50 µL per well. After 1 hour of incubation at room temperature, the hemagglutination status of the samples was visualized, and the optical densities of the cell suspensions at 655 nm were monitored by a plate reader.

Example 21—Microscopic Characterization of Human Erythrocyte Agglutination

2 µL of 4 µM 3-1m was annealed in 1×PBS by incubating the solution at 95° C. and slowly cooling down to 4° C. at a ramp rate of 0.1° C./second, and then incubated at 4° C. for 5 min. To this non-natural aptamer solution, 1 µL of 6.5 µM ConA was added and the solution incubated for 30 min at room temperature. An erythrocyte suspension was prepared to a final hematocrit of 20% in PBS. 7 µL of each erythrocyte suspension was combined either with the ConA-non-natural aptamer complex or 3 µL 1×PBS. 10 µL of this mixture was loaded onto glass slides, covered with coverslips, and immediately visualized using 10× and 40× objective lenses on a microscope.

Figures 19A, 19B:
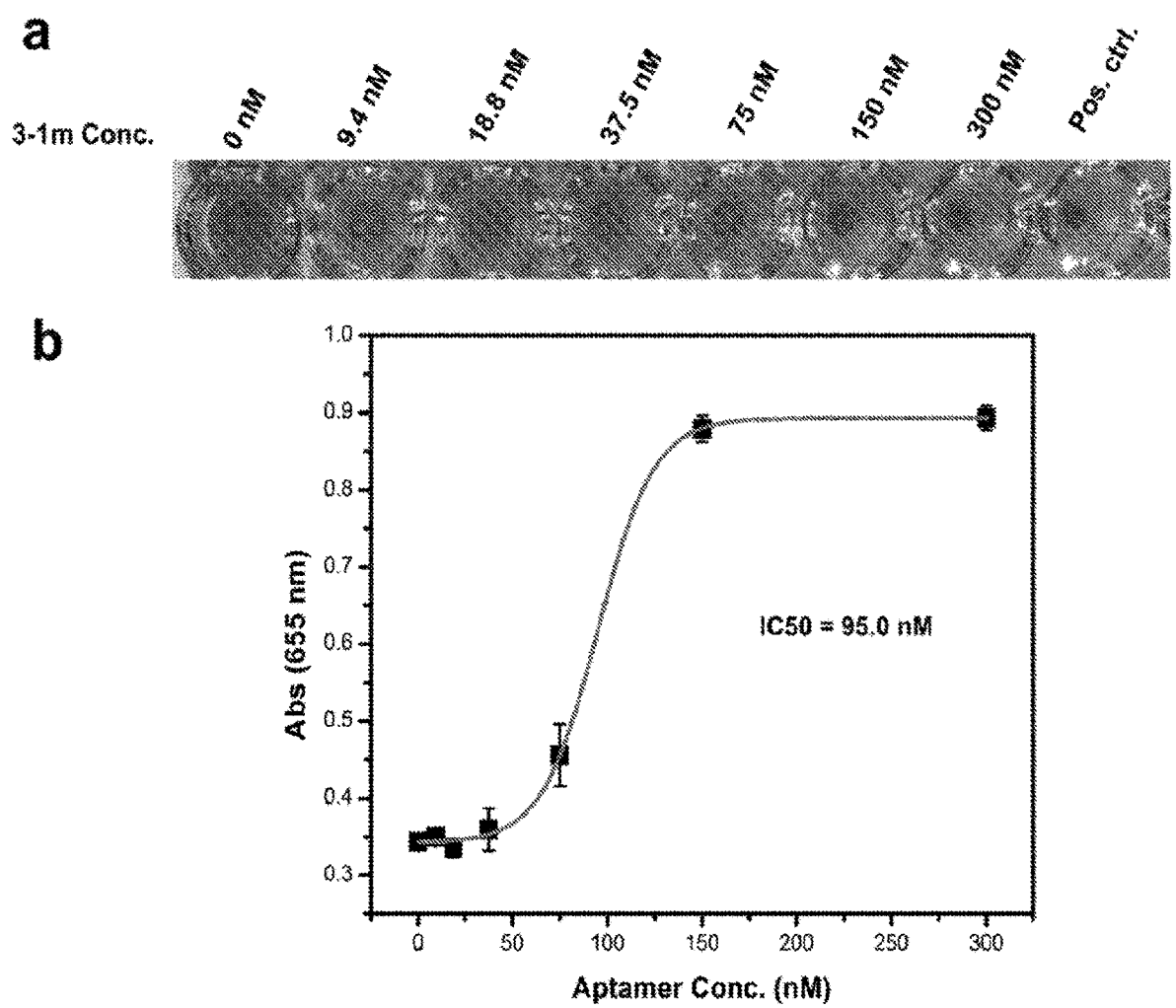
FIGS. 19A-19E: 3-1m is a potent inhibitor of ConA-induced hemagglutination.
Figures 19C, 19D, 19E:
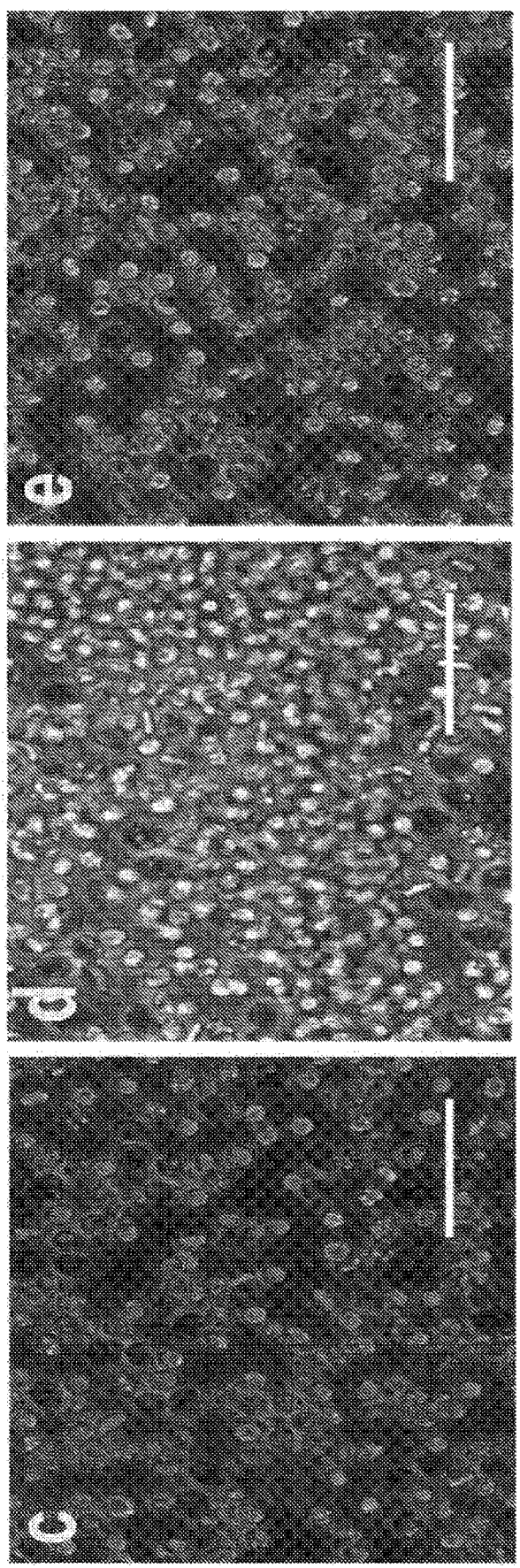

Example 22—ConA Aptamer Inhibits Erythrocyte Agglutination with Remarkable Potency Given the strong affinity and specificity of the glycomimetic reagent for ConA, it was hypothesized that it might act as a highly effective inhibitor of ConA's biological activity. ConA induces clumping of human erythrocytes in a process known as hemagglutination (Glenney et al., 1979), and hemagglutination assays are a standard approach for quantifying activity of this lectin. As a baseline, it was established that complete hemagglutination occurs at 150 nM ConA, based on visual observation of the deposition of erythrocytes in a 96-well plate. This was confirmed by monitoring absorbance of the cell suspension at 655 nm, which correlates to the size of the agglutinated clump (Martins et al., 2014). The extent to which 3-1m can inhibit this process was tested by incubating various concentrations of 3-1m with 150 nM ConA for 30 min at room temperature before adding erythrocytes at 1% hematocrit. Concentration-dependent inhibition of ConA-induced hemagglutination was observed, with complete inhibition at 150 nM and a half-maximal inhibitory concentration (IC50) of 95 nM (FIGS. 19A and 19B). The observation that complete inhibition occurs when both ConA and 3-1m are at the same concentration (150 nM) indicates a stoichiometric relationship, confirming the strong and stable interaction between the binding partners. The inhibition of ConA-induced hemagglutination by 3-1m was also microscopically monitored; the erythrocyte clumps that formed upon the addition of ConA were absent when ConA was incubated with 3-1m beforehand (FIGS. 19C-19E).

Notably, 3-1m inhibits ConA-induced hemagglutination with ~107-fold greater potency than methyl α-D-glucopyranoside, a commonly used inhibitor that achieves maximal effect at 50 mM (Mortell et al., 1994). Furthermore, 3-1m is about three-fold more potent than the best known inhibitor described to date for ConA, a mannose glycopolymer reported by Kiessling et al., which achieves complete inhibition at 500 nM. This is particularly striking given that 3-1m contains 120-fold fewer mannose side chains (14 units) compared with the mannose glycopolymer (~1,700 units), suggesting that its carbohydrate presentation more closely aligns with the active sites of this lectin (Mortell et al., 1996).

REFERENCES

Abdiche, Y., Malashock, D., Pinkerton, A., and Pons, J. (2008). Determining kinetics and affinities of protein interactions using a parallel real-time label-free biosensor, the Octet. Anal. Biochem. 377, 209-217.

Alvarez, C. P., Lasala, F., Carrillo, J., Muñiz, O., Corbi, A. L., and Delgado, R. (2002). C-Type Lectins DC-SIGN and L-SIGN Mediate Cellular Entry by Ebola Virus in cis and in trans. J. Virol. 76, 6841-6844.

Arnaud, J., Audfray, A., and Imberty, A. (2013). Binding sugars: from natural lectins to synthetic receptors and engineered neolectins. Chem. Soc. Rev. 42, 4798-4813.

Bittker, J. A., Phillips, K. J., and Liu, D. R. (2002). Recent advances in the in vitro evolution of nucleic acids. Curr. Opin. Chem. Biol. 6, 367-374.

Boukerb, A. M., Rousset, A., Galanos, N., Mear, J. B., Thepaut, M., Grandjean, T., Gillon, E., Cecioni, S., Abderrahmen, C., Faure, K., et al. (2014). Antiadhesive properties of glycoclusters against *Pseudomonas aeruginosa* lung infection. J. Med. Chem. 57, 10275-10289.

Caminschi, I., Corbett, A. J., Zahra, C., Lahoud, M., Lucas, K. M., Curtis, J., Sofi, M., Vremec, D., Gramberg, T., Po, S., et al. (2006). Functional comparison of mouse CIRE/ mouse. 18, 741-753.

Cecioni, S., Imberty, A., and Vidal, S. (2015). Glycomimetics versus multivalent glycoconjugates for the design of high affinity lectin ligands. Chem. Rev. 115, 525-561.

Committee on Assessing the Importance and Impact of Glycomic and Glycoscience—National Research Council (2012). Transforming Glycoscience: A Roadmap for the Future (Washington, D.C.: The National Academies Press).

Egger, J., Weckerle, C., Cutting, B., Schwardt, O., Rabbani, S., Lemme, K., and Ernst, B. (2013). Nanomolar e-selectin antagonists with prolonged half-lives by a fragment-based approach. J. Am. Chem. Soc. 135, 9820-9828.

Ernst, B., and Magnani, J. L. (2009). From carbohydrate leads to glycomimetic drugs. Nat. Rev. Drug Discov. 8, 661-677.

Fei, Y., Sun, Y.-S., Li, Y., Lau, K., Yu, H., Chokhawala, H. A., Huang, S., Landry, J. P., Chen, X., and Zhu, X. (2011). Fluorescent labeling agents change binding profiles of glycan-binding proteins. Mol. Biosyst. 7, 3343.

Fischler, M., Simon, U., Nir, H., Eichen, Y., Burley, G. a., Gierlich, J., Gramlich, P. M. E., and Carell, T. (2007). Formation of bimetallic Ag—Au nanowires by metallization of artificial DNA duplexes. Small 3, 1049-1055.

Gabius, H.-J., Andre, S., Jiménez-Barbero, J., Romero, A., and Solís, D. (2011). From lectin structure to functional glycomics: principles of the sugar code. Trends Biochem. Sci. 36, 298-313.

Geijtenbeek, T. B. H., Kwon, D. S., Torensma, R., Vliet, S. J. Van, Duijnhoven, G. C. F. Van, Middel, J., Cornelissen, I. L. M. H. A., Nottet, H. S. L. M., Kewalramani, V. N., Littman, D. R., et al. (2000). DC-SIGN, a dendritic cell-specific HIV-1-binding protein that enhances trans-infection of T cells. Cell. 100, 587-597.

Gierlich, J., Burley, G., Gramlich, P. M. E., Hammond, D. M., and Carell, T. (2006). Click chemistry as a reliable method for the high-density postsynthetic functionalization of alkyne-modified DNA. Org. Lett. 8, 3639-3642.

Gierlich, J., Gutsmiedl, K., Gramlich, P. M. E., Schmidt, A., Burley, G., and Carell, T. (2007). Synthesis of highly modified DNA by a combination of PCR with alkyne-bearing triphosphates and click chemistry. Chem. Eur. J. 13, 9486-9494.

Glenney, J. R., Hixson, D. C., and Walborg, E. F. (1979). Inhibition of Concanavalin A-induced agglutination of Novikoff tumor cells by cytochalasins and metabolic inhibitors. Exp. Cell. Res. 118, 353-364.

Gramlich, P. M. E., Wirges, C. T., Gierlich, J., and Carell, T. (2008a). Synthesis of modified DNA by PCR with alkyne-bearing purines followed by a click reaction. Org. Lett. 10, 249-251.

Gramlich, P. M. E., Wirges, C. T., Manetto, A., and Carell, T. (2008b). Postsynthetic DNA modification through the copper-catalyzed azide-alkyne cycloaddition reaction. Angew. Chemie—Int. Ed. 47, 8350-8358.

Hemperly, J. J., Hopp, P., Becker, J. W., and Cunningham, B. A. (1979). The chemical characterization of Favin, a Lectin Isolated from *Vicia faba*. J. Biol. Chem. 254, 6803-6810.

Hili, R, Niu, J., and Liu, D. R. (2013). DNA ligase-mediated translation of DNA into densely functionalized nucleic acid polymers. J. Am. Chem. Soc. 135, 98-101.

Horiya, S., Bailey, J. K., Temme, J. S., Guillen Schlippe, Y. V., and Krauss, I. J. (2014). Directed evolution of multivalent glycopeptides tightly recognized by HIV antibody 2G12. J. Am. Chem. Soc. 136, 5407-5415.

Illescas, B. M., Rojo, J., Delgado, R., and Mart, N. (2017). Multivalent glycosylated nanostructures to inhibit Ebola virus infection. J. Am. Chem. Soc. 139, 6018¬-6025.

Jager, S., Rasched, G., Kornreich-Leshem, H., Engeser, M., Thum, O., and Famulok, M. (2005). A versatile toolbox for variable DNA functionalization at high density. J. Am. Chem. Soc. 127, 15071-15082.

Jin, S., Cheng, Y., Reid, S., Li, M., and Wang, B. (2009). Carbohydrate recognition by boronolectins, small molecules, and lectins. Med. Res. Rev. 30, 171-257.

Jing, M., and Bowser, M. T. (2011). A Review of Methods for Measuring Aptamer-ProteinEquilibria. Anal. Chim. Acta 686, 9-18.

Kelm, S., Madge, P., Islam, T., Bennett, R., Koliwer-Brandl, H., Waespy, M., Von Itzstein, M., and Haselhorst, T. (2013). C-4 modified sialosides enhance binding to Siglec-2 (CD22): Towards potent Siglec inhibitors for immunoglycotherapy. Angew. Chem. Int. Ed. 52, 3616-3620.

Alam, K. K., Chang, J. L., and Burke, D. H. (2015). FASTAptamer: A bioinformatic toolkit for high-throughput sequence analysis of combinatorial selections. Mol. Ther. Nucleic Acids 4, e230.

Macauley, M. S., Crocker, P. R., and Paulson, J. C. (2014). Siglec-mediated regulation of immune cell function in disease. Nat. Rev. Immunol. 14, 653-666.

Macpherson, I. S., Temme, J. S., Habeshian, S., Felczak, K., Pankiewicz, K., Hedstrom, L., and Krauss, I. J. (2011). Multivalent glycocluster design through directed evolution. Angew. Chem. Int. Ed. 50, 11238-11242.

Martins, V. P., Morais, S. B., Pinheiro, C. S., Assis, N. R. G., Figueiredo, B. C. P., Ricci, N. D., Alves-Silva, J., Caliari, M. V., and Oliveira, S. C. (2014). Sm10.3, a member of the micro-exon gene 4 (MEG-4) family, induces erythrocyte agglutination in vitro and partially protects vaccinated mice against *Schistosoma mansoni* infection. PLoS Negl. Trop. Dis. 8, e2750.

Mortell, K. H., Gingras, M., and Kiessling, L. L. (1994). Synthesis of cell agglutination inhibitors by aqueous ring-opening metathesis polymerization. J. Am. Chem. Soc. 116, 12053-12054.

Mortell, K. H., Weatherman, R. V., and Kiessling, L. L. (1996). Recognition specificity of neoglycopolymers prepared by ring-opening metathesis polymerization. J. Am. Chem. Soc. 118, 2297-2298.

Ng, S., Lin, E., Kitov, P. I., Tjhung, K. F., Gerlits, O. O., Deng, L., Kasper, B., Sood, A., Paschal, B. M., Zhang, P., et al. (2015). Genetically-encoded fragment-based discovery of glycopeptide ligands for carbohydrate-binding proteins. J. Am. Chem. Soc. 137, 5248-5251.

Obata, F., Sakai, R, and Shiokawa, H. (1981). Carbohydrate-binding activity of concanavalin A containing various numbers of calcium and manganese ions. J. Biochem. 89, 1475-1482.

Prescher, H., Schweizer, A., Kuhfeldt, E., Nitschke, L., and Brossmer, R. (2014). Discovery of multifold modified sialosides as human CD22/Siglec-2 ligands with nanomolar activity on B-cells. ACS Chem. Biol. 9, 1444-1450.

Richardson, C., Behnke, W. D., Freisheim, J. H., and Blumenthal, K. M. (1986). The complete amino acid sequence of the a-subunit of pea lectin, *Pisum Sativum*. Biochim. Biophys. Acta 537, 310-319.

Schwarz, F. P., Puri, K. D., Bhat, R. G., and Surolia, A. (1993). Thermodynamics of monosaccharide binding to concanavalin A, pea (*Pisum sativum*) lectin lentil (*Lens culinaris*) lectin. J. Biol. Chem. 268, 7668-7677.

Sears, P., and Wong, C. H. (1999). Carbohydrate mimetics: a new strategy for tackling the problem of carbohydrate-mediated biological recognition. Angew. Chem. Int. Ed. 38, 2300-2324.

Shelke, S. V., Cutting, B., Jiang, X., Koliwer-Brandl, H., Strasser, D. S., Schwardt, O., Kelm, S., and Ernst, B. (2010). A fragment-based in situ combinatorial approach to identify high-affinity ligands for unknown binding sites. Angew. Chem. Int. Ed. 49, 5721-5725.

Solís, D., Bovin, N. V., Davis, A. P., Jiménez-Barbero, J., Romero, A., Roy, R., Smetana, K., and Gabius, H.-J. (2015). A guide into glycosciences: How chemistry, biochemistry and biology cooperate to crack the sugar code. Biochim. Biophys. Acta. 1850, 186-235.

Steckbeck, J. D., Orlov, I., Chow, A., Miller, K., Bruno, J., Robinson, J. E., Montelaro, R. C., Cole, K. S., and Grieser, H. (2005). Kinetic rates of antibody binding correlate with neutralization sensitivity of variant simian immunodeficiency virus strains kinetic rates of antibody binding correlate with neutralization sensitivity of variant simian immunodeficiency virus strains. J. Virol. 79, 12311-12320.

Sun, Y. S., Landry, J. P., Fei, Y. Y., Zhu, X. D., Luo, J. T., Wang, X. B., and Lam, K. S. (2008). Effect of fluorescently labeling protein probes on kinetics of protein-ligand reactions. Langmuir 24, 13399-13405.

Temme, J. S., MacPherson, I. S., Decourcey, J. F., and Krauss, I. J. (2014). High temperature SELMA: Evolution of DNA-supported oligomannose clusters which are tightly recognized by HIV bnAb 2G12. J. Am. Chem. Soc. 136, 1726-1729.

Tolle, F., Brändle, G. M., Matzner, D., and Mayer, G. (2015). A versatile approach towards nucleobase-modified aptamers. Angew. Chemie Int. Ed. 54, 10971-10974.

Wang, J., Gong, Q., Maheshwari, N., Eisenstein, M., Arcila, M. L., Kosik, K. S., and Soh, H. T. (2014). Particle display: A quantitative screening method for generating high-affinity aptamers. Angew. Chem. Int. Ed. 126, 4896-4901.

Wang, J., Yu, J., Yang, Q., McDermott, J., Scott, A., Vukovich, M., Lagrois, R, Gong, Q., Greenleaf, W., Eisenstein, M., Ferguson, B. S., Soh, H. T. (2017). Multiparameter particle display (MPPD): A quantitative screening method for the discovery of highly specific aptamers. Angew. Chem. Int. Ed. Engl. 56, 744-747.

Yang, X., Cheng, Y., and Wang, B. (2011). Synthetic lectin mimics artificial carbohydrate receptors. In Carbohydrate Recognition: Biological Problems, Methods, and Applications, B. Wang, and G.-J. Boons, eds. (New York, NY: John Wiley & Sons), pp. 301-321.

Zand, R., Agrawal, B. B., and Goldstein, I. J. (1971). pH-dependent conformational changes of concanavalin A. Proc. Natl. Acad. Sci. U.S.A 68, 2173-2176.

Zeng, Y., Rademacher, C., Nycholat, C. M., Futakawa, S., Lemme, K., Ernst, B., and Paulson, J. C. (2011). High affinity sialoside ligands of myelin associated glycoprotein. Bioorg. Med. Chem. Lett. 21, 5045-5049.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A plurality of beads linked to aptamers comprising at least one non-natural nucleotide, wherein the sequences of aptamers linked to different beads are different, wherein each bead in the plurality are linked to multiple copies of only one aptamer, and wherein the base of the non-natural nucleotide is covalently bonded to a binding agent.

2. The plurality of beads of claim 1, wherein the non-natural nucleotide is covalently bonded to the binding agent via a triazole moiety.

3. The plurality of beads of claim 1, wherein the non-natural nucleotide is C8-alkyne-dUTP.

4. The plurality of beads of claim 1, wherein aptamers linked to the beads comprise at least first and a second non-natural nucleotides that are structurally-different.

5. The plurality of beads of claim 4, wherein the first non-natural nucleotide is linked to the binding agent and the second non-natural nucleotide is not linked to a binding agent.

6. The plurality of beads of claim 5, wherein the second non-natural nucleotide comprises an aldehyde.

7. The plurality of beads of claim 4, wherein the first non-natural nucleotide is linked to the binding agent and the second non-natural nucleotide is linked to a second binding agent.

8. The plurality of beads of claim 1, wherein the binding agent is an amino acid, a sugar, a peptide, or a protein.

9. The plurality of beads of claim 8, wherein the binding agent is an azide-modified tyrosine.

10. The plurality of beads of claim 8, wherein the binding agent is an azide-modified tryptophan.

11. The plurality of beads of claim 8, wherein the binding agent is an azide-modified boronic acid.

12. The plurality of beads of claim 1, wherein the plurality of beads comprises at least 100 beads each linked to a different aptamer having a different sequence.

13. A method of making the plurality of beads linked to aptamers of claim 1, the method comprising,
providing a plurality of aqueous droplets wherein a majority of the droplets comprise only one bead linked to a forward primer and only one aptamer template polynucleotide, wherein the droplets in the majority each comprise an aptamer template polynucleotide having a different sequence;
performing amplification within the droplets, wherein the droplets contain nucleotide triphosphates (NTPs) and a non-natural nucleotide triphosphate having a nucleotide base linked to a functional group, wherein the forward primer hybridizes to the aptamer template polynucleotide and is extended by a polymerase using the aptamer template polynucleotide as a template to generate an extension product linked to the bead and comprising an aptamer sequence and wherein the non-natural nucleotide is incorporated into the aptamer sequence, thereby forming a plurality of beads linked to aptamers comprising at least one non-natural nucleotide; and
reacting the functional group with a reactive species comprising a binding agent such that the non-natural nucleotide is covalently bonded to the binding agent.

14. The methods of claim 13, wherein the functional group is an alkyne or an azide.

15. The method of claim 13, wherein the droplets contain at least a first and a second non-natural nucleotide triphosphate that are structurally-different and wherein the first and the second non-natural nucleotide are incorporated into the aptamer sequence.

16. The method of claim 15, wherein the first non-natural nucleotide comprises an alkyne or an azide functional group and the second non-natural nucleotide comprises an aldehyde.

17. The method of claim 13, further comprising combining contents of the droplets after the performing of the amplification and before the reacting.

18. The method of claim 13, wherein the non-natural nucleotide is C8-alkyne-dUTP.

19. The method of claim 13, wherein a first non-natural nucleotide comprises an alkyne and the reactive species comprises an azide and during the reacting the azide undergoes Cu-catalyzed azide-alkyne cycloaddition (CuAAC) with the alkyne in the non-natural nucleotide to form a covalent bond.

20. A method of identifying an aptamer that binds a target molecule, the method comprising
contacting the plurality of beads of claim 1 to the target molecule;
enriching the plurality of beads for beads that bind the target molecule; and
determining the sequence of aptamers that bind the target molecule.

* * * * *

UNITED STATES PATENT AND TRADEMARK OFFICE
CERTIFICATE OF CORRECTION

PATENT NO. : 12,060,559 B2  
APPLICATION NO. : 15/734522  
DATED : August 13, 2024  
INVENTOR(S) : Jia Niu, Chelsea Lyons Gordon and Hyongsok Tom Soh Page 1 of 1

It is certified that error appears in the above-identified patent and that said Letters Patent is hereby corrected as shown below:

On the Title Page

In Column 1, (72) Inventors:  
Delete "Hyongsok Tom Soh, San Francisco, CA (US)" and  
Insert -- Hyongsok Tom Soh, Palo Alto, CA (US) --.

In Column 1, (22) PCT Filed:  
Delete "Jun. 19, 2019" and  
Insert -- Jun., 04, 2019 --.

In the Claims

In Column 58, Line 14 In Claim 18, Line 1:  
Delete "methods" and  
Insert -- method --.

Signed and Sealed this  
Eighth Day of October, 2024

Katherine Kelly Vidal  
*Director of the United States Patent and Trademark Office*

SEQUENCE LISTING

```
<160> NUMBER OF SEQ ID NOS: 47

<210> SEQ ID NO 1
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
atccagagtg acgcagcacg gaacgtctttt gtaacttgaa ataccgtggt aggttggcta      60
ggttggacac ggtggcttag t                                                81

<210> SEQ ID NO 2
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
atccagagtg acgcagcacg gaacgtctttt gtaacttgaa ataccgtggt aggttggcta      60
ggttggacac ggtggcttag t                                                81

<210> SEQ ID NO 3
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
gatcccagtc cgaagtaatc gttgcatctg cacgactggt gagcttgagt ggcagaagaa      60
cttgtgcaaa cggctatagg                                                  80
```

<210> SEQ ID NO 4
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
gatcccagtc cgaagtaatc gaagcatctg cacgactggt gagcttgagt ggcagaagaa    60
cttgtgcaaa cggctatagg                                                80

<210> SEQ ID NO 5
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
gatcccagtc cgaagtaatc gttgcaacag cacgactggt gagcttgagt ggcagaagaa    60
cttgtgcaaa cggctatagg                                                80

<210> SEQ ID NO 6
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
gatcccagtc cgaagtaatc gttgcatctg cacgacagga gagcttgagt ggcagaagaa    60
cttgtgcaaa cggctatagg                                                80

<210> SEQ ID NO 7
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
gatcccagtc cgaagtaatc gttgcatctg cacgactggt gagcaagagt ggcagaagaa    60
cttgtgcaaa cggctatagg                                                80

<210> SEQ ID NO 8
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
gatcccagtc cgaagtaatc gttgcatctg cacgactggt gagcttgaga ggcagaagaa    60
cttgtgcaaa cggctatagg                                                80

<210> SEQ ID NO 9
<211> LENGTH: 80

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
gatcccagtc cgaagtaatc gatgcatctg cacgactggt gagcaagagt ggcagaagaa    60
cttgtgcaaa cggctatagg                                                80

<210> SEQ ID NO 10
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
gatcccagtc cgaagtaatc gtagcatctg cacgactggt gagcaagagt ggcagaagaa    60
cttgtgcaaa cggctatagg                                                80

<210> SEQ ID NO 11
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
gatcccagtc cgaagtaatc gttgcaactg cacgactggt gagcaagagt ggcagaagaa    60
cttgtgcaaa cggctatagg                                                80

<210> SEQ ID NO 12
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
gatcccagtc cgaagtaatc gttgcatcag cacgactggt gagcaagagt ggcagaagaa    60
cttgtgcaaa cggctatagg                                                80

<210> SEQ ID NO 13
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
gatcccagtc cgaagtaatc gttgcatctg cacgacaggt gagcaagagt ggcagaagaa    60
cttgtgcaaa cggctatagg                                                80

<210> SEQ ID NO 14
<211> LENGTH: 80
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 14
gatcccagtc cgaagtaatc gttgcatctg cacgactgga gagcaagagt ggcagaagaa      60
cttgtgcaaa cggctatagg                                                 80

<210> SEQ ID NO 15
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
gatcccagtc cgaagtaatc gttgcatctg cacgactggt gagcttgagt ggcagaagaa      60
cttgtgcaaa cggctatagg                                                 80

<210> SEQ ID NO 16
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
tatcatggac tatacggagg tagatcggat atgcgaacca                            40

<210> SEQ ID NO 17
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
ctccgcggat caatgcagag gattgcagat cctcgacatg                            40

<210> SEQ ID NO 18
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
cttcgcggat caatgcagag gattgcagat cctcaacatg                            40

<210> SEQ ID NO 19
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
gttgcatctg cacgactggt gagcttgagt ggcagaagaa                            40

<210> SEQ ID NO 20
<211> LENGTH: 40
<212> TYPE: DNA

<213> ORGANISM: Artificial Sequence
<220> FEATURE:
<223> OTHER INFORMATION: Description of Artificial Sequence: Synthetic
    oligonucleotide

<400> SEQUENCE: 20
gttgcatctg cactactggt gaacttgagt ggcagaagaa           40

<210> SEQ ID NO 21
<211> LENGTH: 40
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 21
gttgcatctg cacgactggt gaacttgagt ggcagaagaa           40

<210> SEQ ID NO 22
<211> LENGTH: 40
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 22
agcgataggt gcactggggt cctctaagcg cgttaacgag           40

<210> SEQ ID NO 23
<211> LENGTH: 40
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 23
tagtacggag gaacgtgcga gcggtagcat tatagcgaga           40

<210> SEQ ID NO 24
<211> LENGTH: 38
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 24
cacgtactgc tacgggggag ggaggtatct gtcgcgga             38

<210> SEQ ID NO 25
<211> LENGTH: 37
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 25
cacgtactgc tacgggaagg gaggtatctg tcgcgga              37

<210> SEQ ID NO 26
<211> LENGTH: 40
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 26
tctgtgacgg tacgtcgctg aagaagttg ggacgtatta                              40

<210> SEQ ID NO 27
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
gaagcaagtt ggtctttaac gatacaacag cttgcggaac                             40

<210> SEQ ID NO 28
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
ggaggtgtta ctggccgggg aagattgagg gtggcgtgg                              39

<210> SEQ ID NO 29
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
gttgaatctg gatacgattt ctgagttctt aatgggaaga                             40

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
cggaacgtct ttgtaacttg a                                                 21

<210> SEQ ID NO 31
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
atccagagtg acgcagcacg gaacgtcttt gtaacttgaa ataccgtggt aggttggcta       60
ggttggacac ggtggcttag t                                                 81

<210> SEQ ID NO 32
<211> LENGTH: 81
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 32
atccagagtg acgcagcacg gaacgtcttt gtaacttgaa ataccgtggt aggttggcta    60
ggttggacac ggtggcttag t                                              81

<210> SEQ ID NO 33
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
atccagagtg acgcagca                                                  18

<210> SEQ ID NO 34
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
actaagccac cgtgtcca                                                  18

<210> SEQ ID NO 35
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
actaagccac cgtgtcca                                                  18

<210> SEQ ID NO 36
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(60)
<223> OTHER INFORMATION: a, c, t, g, unknown or other

<400> SEQUENCE: 36
gatcccagtc cgaagtaatc nnnnnnnnnn nnnnnnnnnn nnnnnnnnnn nnnnnnnnnn    60
cttgtgcaaa cggctatagg                                                80

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37

```
gatcccagtc cgaagtaatc                                                20
```

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38

```
gatcccagtc cgaagtaatc                                                20
```

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39

```
cctatagccg tttgcacaag                                                20
```

<210> SEQ ID NO 40
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40

```
gatcccagtc cgaagtaatc gttgcatctg cacgactggt gagcttgagt ggcagaagaa    60
cttgtgcaaa cggctatagg                                                80
```

<210> SEQ ID NO 41
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41

```
gatcccagtc cgaagtaatc gttgcatctg cacgactggt gagcttgagt ggcagaagaa    60
cttgtgcaaa cggctatagg                                                80
```

<210> SEQ ID NO 42
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42

```
gatcccagtc cgaagtaatc gttgcatctg cacgactggt gagcttgagt ggcagaagaa    60
cttgtgcaaa cggctatagg                                                80
```

<210> SEQ ID NO 43
<211> LENGTH: 80
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 43
gatcccagtc cgaagtaatc gttgcatctg cacgactggt gagcttgagt ggcagaagaa      60
cttgtgcaaa cggctatagg                                                 80

<210> SEQ ID NO 44
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
gatcccagtc cgaagtaatc gttgcatctg cacgactggt gagcttgagt ggcagaagaa      60
cttgtgcaaa cggctatagg                                                 80

<210> SEQ ID NO 45
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
gatcccagtc cgaagtaatc agcagttaat gttaggatgc ggaggcgcat acgtcgtacg      60
cttgtgcaaa cggctatagg                                                 80

<210> SEQ ID NO 46
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
gatcccagtc cgaagtaatc cccctccct cctccctcc ctccctccct cctccctcc        60 cttgtgcaaa cggctatagg                                                 80

<210> SEQ ID NO 47
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
gatcccagtc cgaagtaatc caagggtaat tgggaaataa ggatggggta atatgcaacc      60
cttgtgcaaa cggctatagg                                                 80
```